(12) United States Patent  (10) Patent No.: US 8,236,935 B2
Quirion et al.  (45) Date of Patent: Aug. 7, 2012

(54) GEM-DIFLUORINATED C-GLYCOSIDE COMPOUNDS DERIVED FROM PODOPHYLLOTOXIN, THEIR PREPARATION AND THEIR APPLICATIONS

(75) Inventors: Jean-Charles Quirion, Bourg-Achard (FR); Geraldine Castle Deliencourt-Godefroy, Rouen (FR); Christophe Audouard, Grand Quevilly (FR)

(73) Assignee: Institut National des Sciences Appliquees de Rouen (INSA), Mont Saint Aignan Cedex (FR)

( * ) Notice: Subject to any disclaimer, the term of this patent is extended or adjusted under 35 U.S.C. 154(b) by 563 days.

(21) Appl. No.: 12/298,642

(22) PCT Filed: Apr. 24, 2007

(86) PCT No.: PCT/FR2007/000697
§ 371 (c)(1),
(2), (4) Date: Feb. 25, 2009

(87) PCT Pub. No.: WO2007/125194
PCT Pub. Date: Nov. 8, 2007

(65) Prior Publication Data
US 2009/0318675 A1 Dec. 24, 2009

(30) Foreign Application Priority Data
Apr. 25, 2006 (FR) .................................. 06 03766

(51) Int. Cl.
*C07H 5/04* (2006.01)
*C07H 5/06* (2006.01)
*C08B 37/00* (2006.01)
*A01N 43/04* (2006.01)
*A61K 31/70* (2006.01)
(52) U.S. Cl. .................. 536/18.7; 536/55.3; 514/23
(58) Field of Classification Search .................. None
See application file for complete search history.

(56) References Cited
OTHER PUBLICATIONS
Vippagunta et al. Advanced Drug Delivery Reviews 48 (2001) 3-26.*
Henwood et al. Drugs. Mar. 1990; 30(3): 438-90, abstract only.*
* cited by examiner

*Primary Examiner* — Layla Bland
(74) *Attorney, Agent, or Firm* — Browdy and Neimark, PLLC

(57) ABSTRACT

The invention relates to a gem-difluoride glycoconjugated compound with formula (I): where R represents H or a benzyl, acetyl, benzoyl alkyl group, $R^1$ and $R^2$ may be identical or different and represent H or an alkyl, benzyl, benzoyl, acetyl, pivaloyl, trialkylsilyl, tertiobutyldiphenylsilyl protective group or an acetal group of the CR'R' type, where R' and R' may be identical or different and represent H or an alkyl, aryl, benzyl or thiophene group, $R^3$ represents H or an alkyl, benzyl, benzoyl, acetyl, pivaloyl, trialkylsilyl or tertiobutyl-diphenylsilyl protective group, $R^4$ represents OR", NGR'GR', $N_3$, or a phthalimide, where R" represents H or an alkyl, benzyl, benzoyl, acetyl, pivaloyl, trialkylsilyl or tertiobutyl-diphenylsilyl protective group, GR' and GR' may be identical or different and represent H or an alkyl, benzyl, benzoyl, acetyl, alkyloxycarbonyl, allyloxycarbonyl or benzyloxycar-bonyl group, $R^5$ represents a free or protected hydroxyl group or a halogen, $R^6$ represents H or an alkyl, acetyl, benzyl, $PO_3H$ or $PO_3Na$ group. It is applicable to the preparation of compounds that can be used particularly for the treatment of cancer.

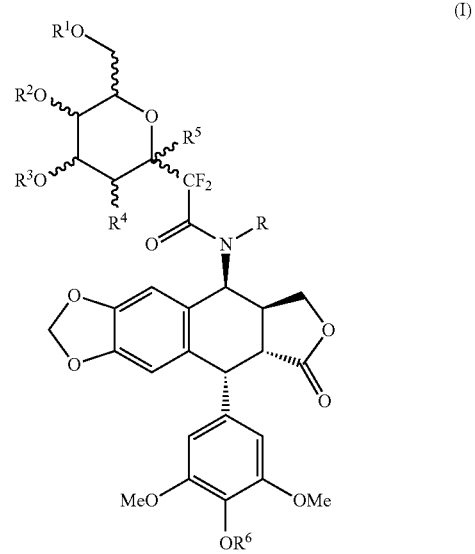

17 Claims, 18 Drawing Sheets

5eq NaN$_3$, CHCl$_3$, 2h
rt, 1.4eq CF$_3$COOH

H$_2$, Pd/C, AcOEt, rt, overnight

R=H  26a/b
R=Me 27a/b dimethoxyethane
APTS, MeNO₂, rt, 2h
→

R=H  28a/b
R=Me 29a/b

GEM-DIFLUORINATED C-GLYCOSIDE COMPOUNDS DERIVED FROM PODOPHYLLOTOXIN, THEIR PREPARATION AND THEIR APPLICATIONS

BACKGROUND OF THE INVENTION

1. Field of the Invention

The invention relates to a method for the synthesis of gem-difluorinated C-glycoside compounds derived from podophyllotoxin. It more particularly, but not exclusively, applies to the preparation of compounds which may be notably used in oncology for treating cancer.

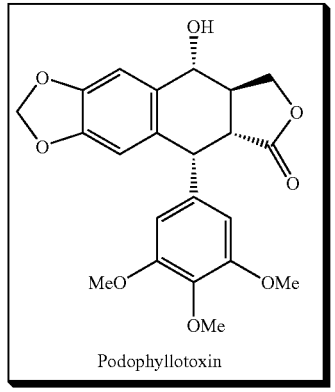

Podophyllotoxin

2. Description of the Prior Art

Podophyllotoxin 1 is a lignan isolated from the roots of two plants *Podophyllum peltatum* (North America) and *Podophyllum emodi* (Asia). It has strong antimitotic activity by inhibiting polymerization of tubulin. Too toxic to be used in chemotherapy, it has given rise to many antitumoral compounds after structural modifications. Among them, glycosylated derivatives, compounds which are usually less toxic and more water-soluble, have emerged.

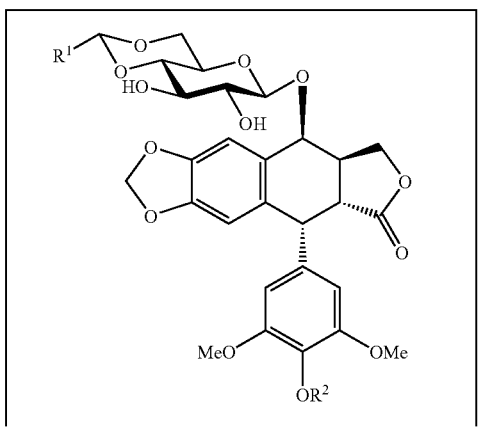

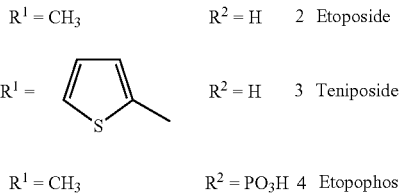

This the case of etoposide 2 (or VP-16) notably used in the treatment of small cell lung cancer, cancer of the bladder, of the testicles, of lymphomas, acute leukemias, Kaposi sarcomas.

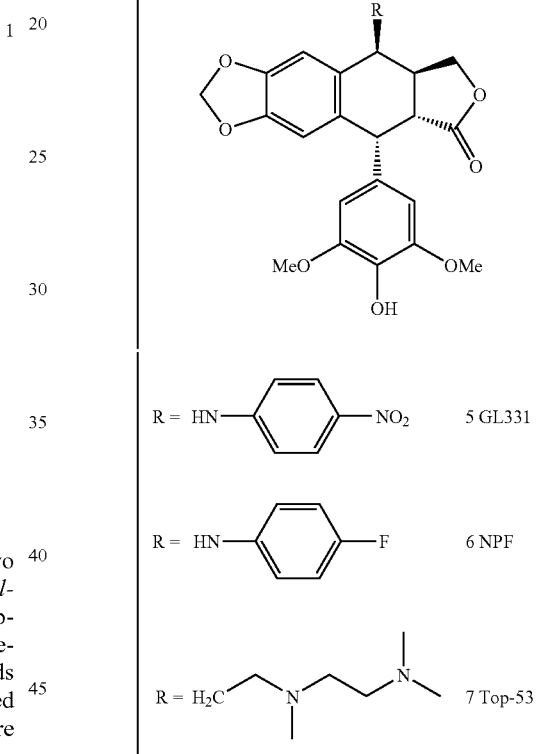

Nitrogen-containing derivatives of podophyllotoxin such as GL-331 5, NPF 6 or TOP-53 7 also show very interesting activities.

All these molecules derived from the demethylepipodophyllotoxin structure are inhibitors of topoisomerase II, an enzyme which catalyses nicking and then reformation of the 2 DNA strands.

We have developed the synthesis of nitrogen-containing compounds of podophyllotoxin, with an amide function substituted with a gem-difluorinated glycoside.

The importance of the $CF_2$ group is in addition to its resistance against biochemical degradation processes, the fact that it forms an excellent mimic of oxygen. It thereby allows synthesis of non-hydrolyzable structures.

Such compounds would be able to be used as chemotherapy agents in the treatment of different types of cancer, either alone or associated with other chemotherapies within the scope of a multitherapy.

The developed molecules belong to the series of nitrogen-containing analogs of podophyllotoxin, a family having significant cytotoxicity.

Further the presence of a glycoside is known for improving solubility in aqueous solvents, and for reducing toxicity.

The use of difluorinated analogs in the anomeric position of the glycoside further reinforces their stability against acido-basic and especially enzymatic hydrolyses.

SUMMARY OF THE INVENTION

For this purpose, the invention proposes a gem-difluorinated glycoconjugated compound with general formula I:

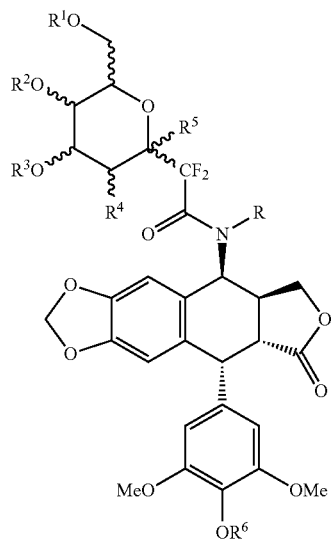

wherein R represents a hydrogen atom or a linear or branched alkyl, benzyl, acetyl, benzoyl group,
  $R^1$ and $R^2$, either identical or different,
  represent a hydrogen atom
    or a protective linear or branched alkyl, benzyl, benzoyl, acetyl, pivaloyl, trialkylsilyl, terbutyldiphenylsilyl group
    or an acetal group, of the CR'R" type,
      with R' and R", either identical or different, representing a hydrogen atom or a linear or branched alkyl, aryl, benzyl, thiophene group,
  $R^3$ represents a hydrogen atom
    or a linear or branched alkyl, benzyl, benzoyl, acetyl, pivaloyl, trialkylsilyl, tertiobutyldiphenylsilyl protective group,
  $R^4$ represents OR''', NGR'GR", $N_3$, or a phthalimide
    with R''' representing a hydrogen atom or a protective linear or branched alkyl, benzyl, benzoyl, acetyl, pivaloyl, trialkylsilyl, tertiobutyldiphenylsilyl group,
      GR' and GR", either identical or different, representing a hydrogen atom or a linear or branched alkyl, benzyl, benzyl, acetyl, alkyloxycarbonyl, allyloxycarbonyl, benzyloxycarbonyl group,
  $R^5$ represents a free or protective hydroxyl group or a halogen,
  $R^6$ represents a hydrogen atom or a linear or branched alkyl, acetyl, benzyl, $PO_3H$, $PO_3Na$ group,
as well as its derivatives in the state of a base, of a mineral or organic acid addition salt or a hydrate or a possibly pharmaceutically acceptable solvate.

More specifically, a compound according to the invention may have a general formula II:

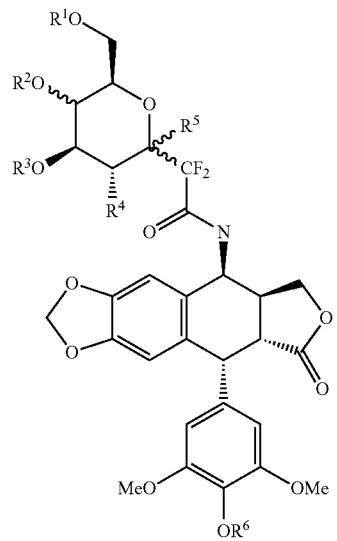

wherein R, $R^1$, $R^2$, $R^3$, $R^4$, $R^5$ and $R^6$ are such as defined in formula I,
as well as its derivatives in the state of a base, of a mineral or organic acid addition salt, of a hydrate or of a possibly pharmaceutically acceptable solvate.

The compounds of formula I and II may be used for example by a reaction for reducing the amide function, for the synthesis of compounds of formula III:

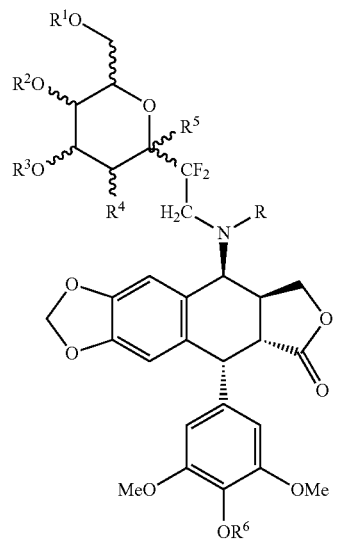

wherein R represents a hydrogen atom or a linear or branched alkyl, benzyl, acetyl, benzoyl group,
  $R^1$ and $R^2$, either identical or different,
  represent a hydrogen atom
    or a protective linear or branched alkyl, benzyl, benzoyl, acetyl, pivaloyl, trialkylsilyl, tertiobutyldiphenylsilyl group
    or an acetal group of the CR'R" type,
      with R' and R", either identical or different, representing a hydrogen atom or a linear or branched alkyl, aryl, benzyl, thiophene group, $R^3$ represents a hydrogen atom or a protective linear or branched alkyl, benzyl, benzoyl, acetyl, pivaloyl, trialkylsilyl, tertiobutyldiphenylsilyl group, $R^4$ represents OR''', NGR'GR'', $N_3$, or a phthalimide with R''' representing a hydrogen atom or a protective linear or branched alkyl, benzyl, benzoyl, acetyl, pivaloyl, trialkylsilyl, tertiobutyldiphenylsilyl group, GR' and GR'', either identical or different, representing a hydrogen atom of a linear or branched alkyl, benzyl, benzoyl, acetyl, alkyloxycarbonyl, allyloxycarbonyl, benzyloxycarbonyl group, $R^5$ represents a free or protective hydroxyl group or a halogen, $R^6$ represents a hydrogen atom or a linear or branched alkyl, acetyl, benzyl, $PO_3H$, $PO_3Na$ group, as well as its derivatives in the state of a base, of a mineral or organic acid addition salt, of a hydrate or of a possibly pharmaceutically acceptable solvate.

In formulae I to III, the linear or branched alkyl groups may be groups having 1 to 10 carbon atoms.

The compounds of general formulae I to III as defined earlier, i.e. comprising their derivatives in the state of a base, of a mineral or organic acid addition salt, of a hydrate or of a possibly pharmaceutically acceptable solvate may appear as different galenic forms adapted to their use, for example injectable solutions or suspensions.

A method for preparing compounds of formula I comprises a coupling step between a compound of formula IV:

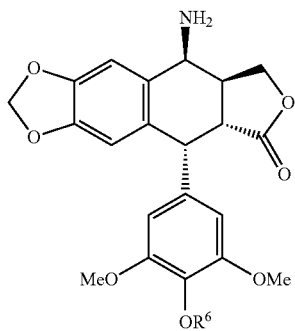

wherein $R^6$ is as defined in formula I
and a compound of formula V:

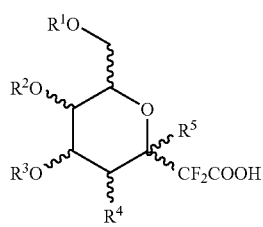

wherein $R^1$, $R^2$, $R^3$, $R^4$, $R^5$ are as defined in formula I.

Said compound of formula IV is obtained by epimerization and then by substituting the alcohol function in position 4 by an azido group subsequently reduced into an amine group.

The compound of formula V is obtained via an intermediate compound of formula VI:

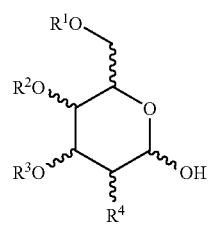

wherein $R^1$, $R^2$, $R^3$, $R^4$ are as defined in formula I.

When in the compound of formula V, $R^5$ represents a hydroxyl group, the preparation of said compound of formula V further comprises oxidation of the compound of formula VI into a lactone, followed by a Reformatsky reaction.

The object of the invention is also a drug containing as an active ingredient, at least one compound of formula I to III as defined earlier.

According to another of its aspects, the present invention relates to the use of at least one compound of general formula I to III as defined earlier for preparing drugs/compositions for treating cancers such as for example small cell lung cancer, cancer of the bladder, of testicles, lymphomas, acute leukemias, Kaposi sarcomas.

Another object of the invention relates to a composition comprising at least one compound of formula I to III as defined earlier.

Of course, the composition according to the invention may comprise compounds of formula I to III as defined earlier, alone or in a mixture and in any proportions.

The composition according to the invention may be intended for pharmaceutical use.

In pharmaceutical compositions according to the present invention for administration via an oral, sublingual, inhalation, subcutaneous, intramuscular, intravenous, transdermal, local or rectal route, the active ingredients may be administered as unit administration forms, in a mixture with standard pharmaceutically acceptable supports/carriers.

The suitable unit administration forms comprise oral forms such as tablets, gelatin capsules, powders, granules and oral solutions or suspensions, topical administration forms, implants, subcutaneous, intramuscular, intravenous, intranasal or intraocular administration forms and rectal administration forms.

In addition to the inert, non-toxic and pharmaceutically acceptable excipients, such as distilled water, glucose, starch lactose, talc, vegetable oils, ethylene glycol . . . , the thereby obtained compositions may also contain preservatives.

Other active ingredients may be added into the compositions.

The amount of compound according to the invention and of other possible active ingredients in such compositions may vary depending on the applications, the age, and the weight of the patient, if necessary.

BRIEF DISCRIPTION OF THE DRAWINGS

Examples for preparing compounds according to the invention will be described hereafter, as non-limiting examples, with reference to the appended drawings wherein.

Figure 8:
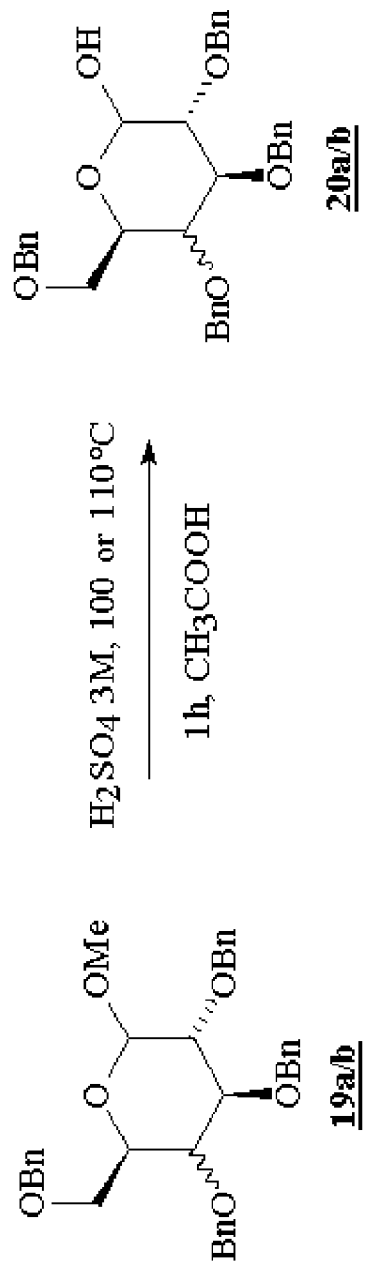
Figure 9:
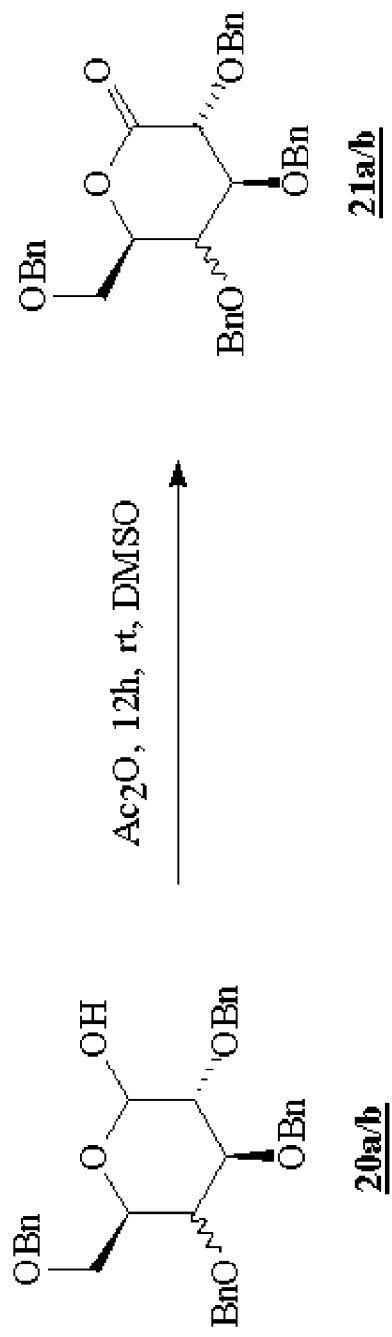
Figure 10:
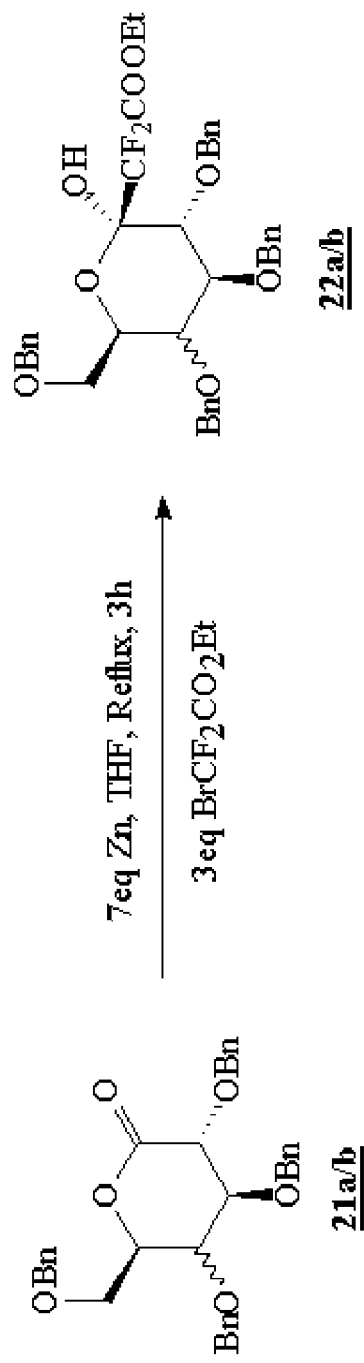
Figure 11:
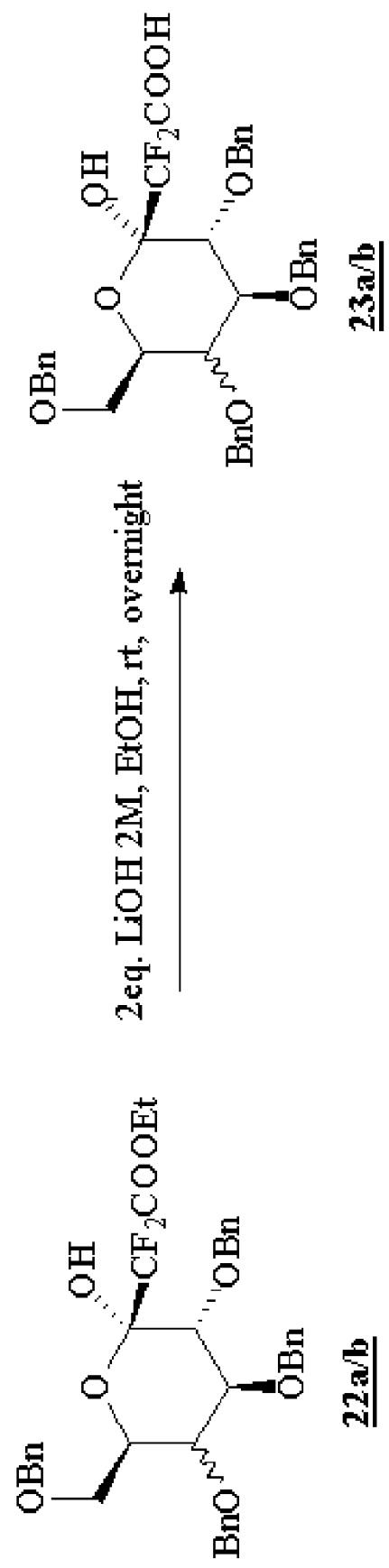
Figure 12:
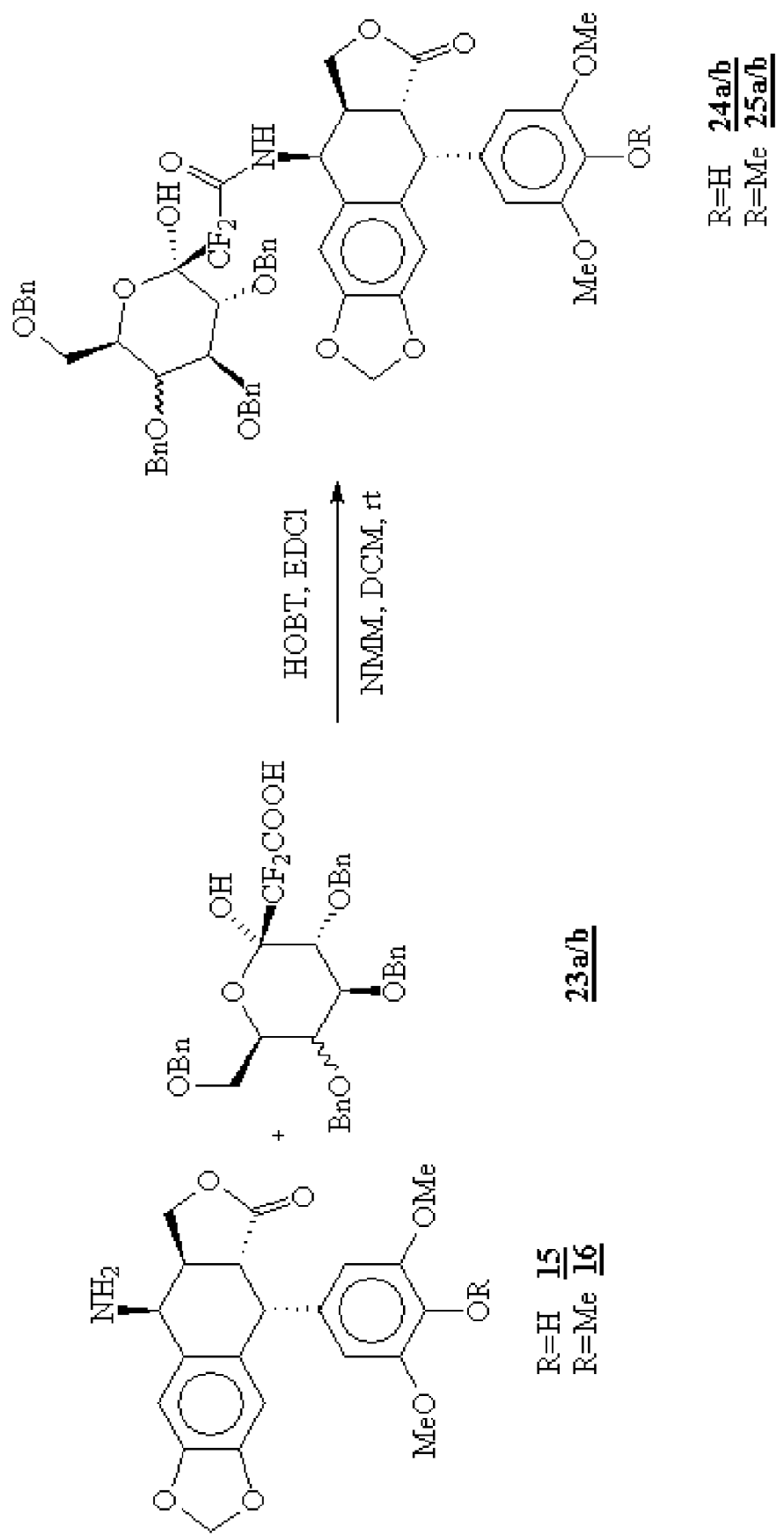
Figure 13:
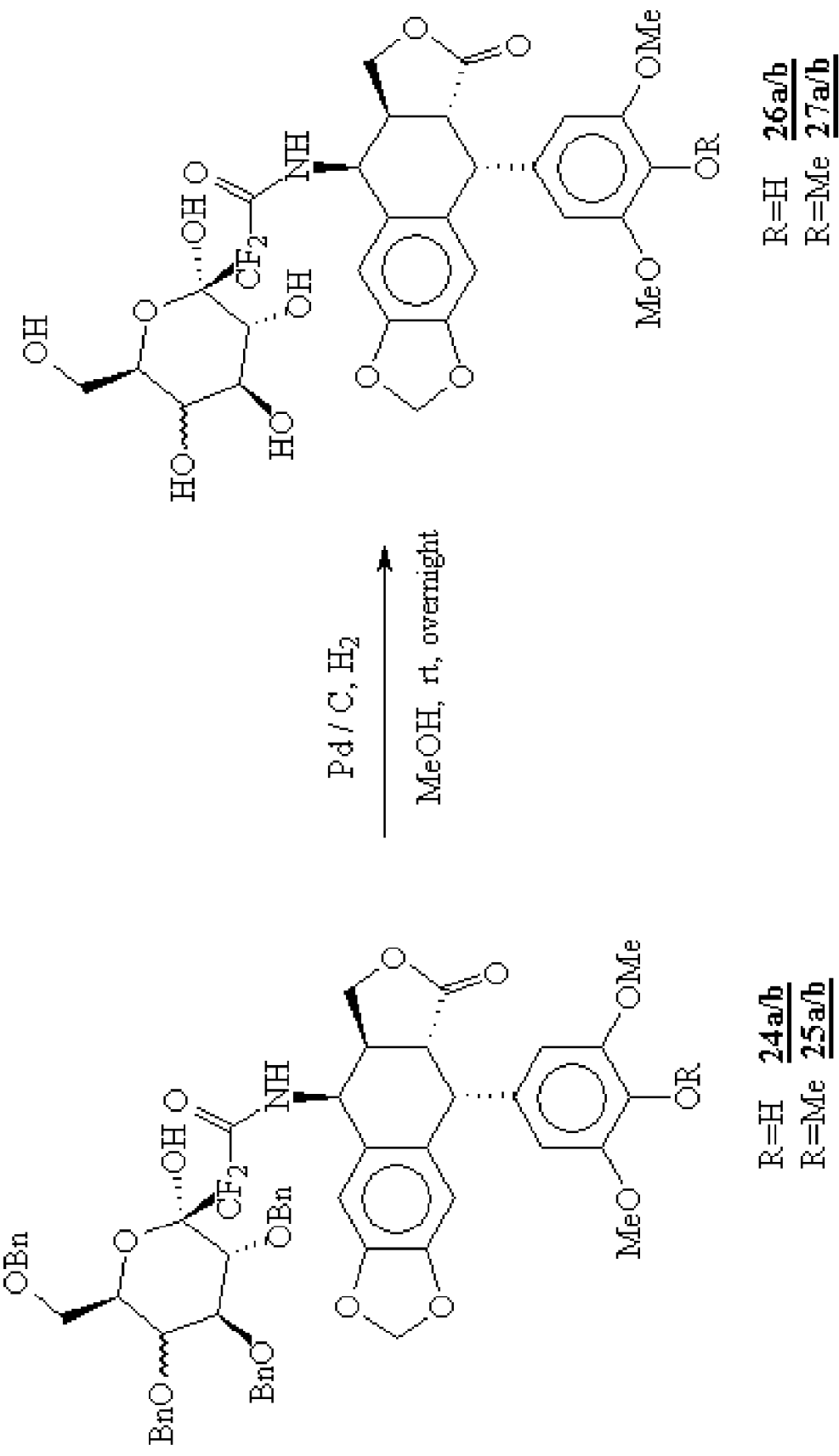
Figure 14:
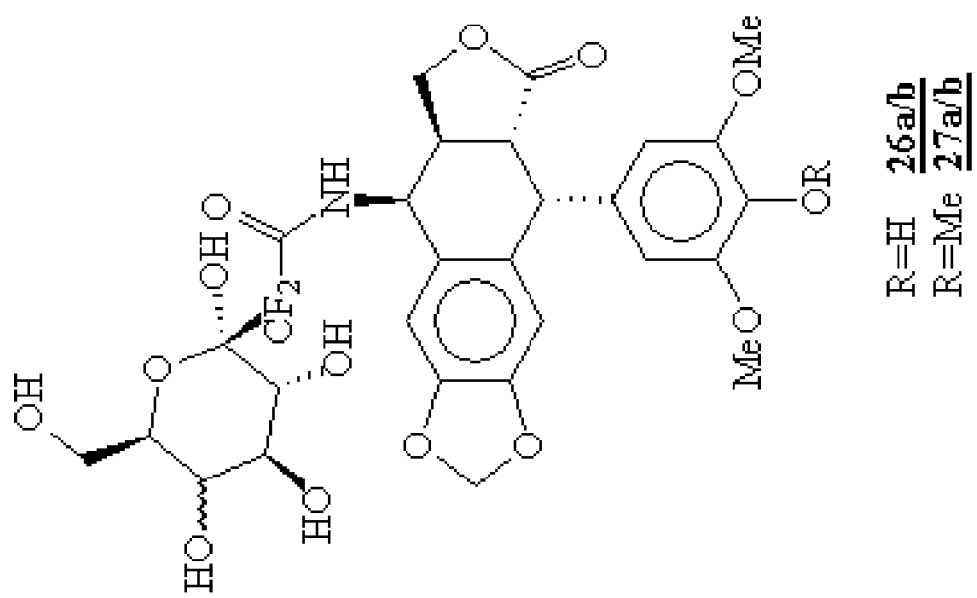
Figure 14:
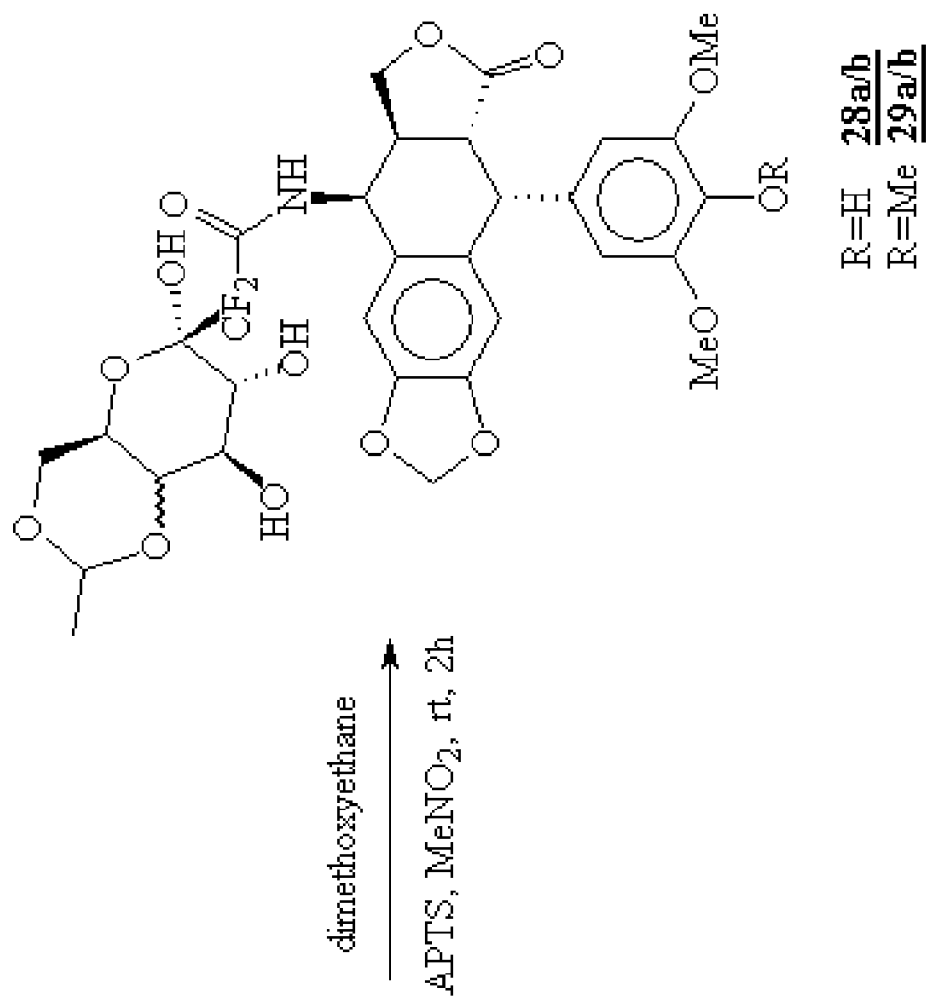
Figure 15:
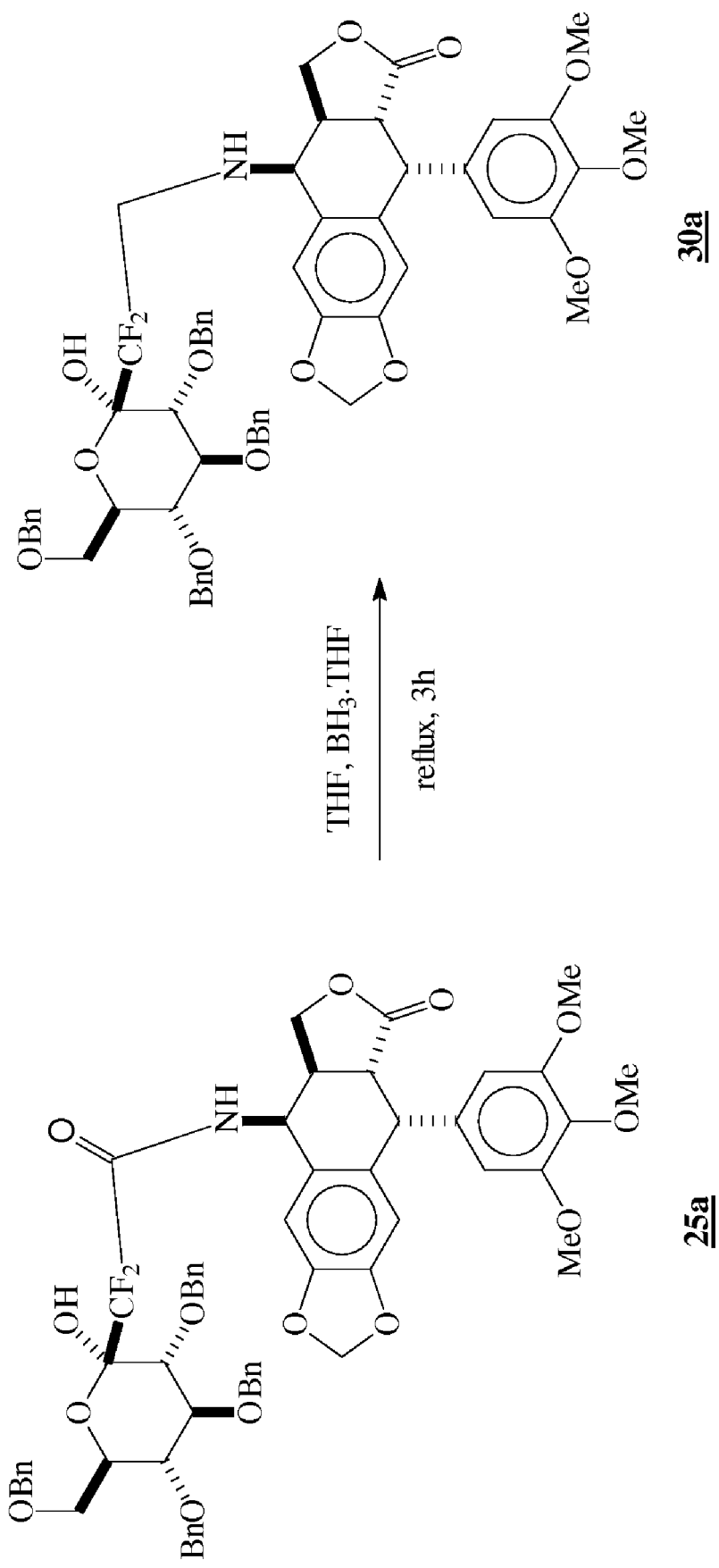
Figure 16:
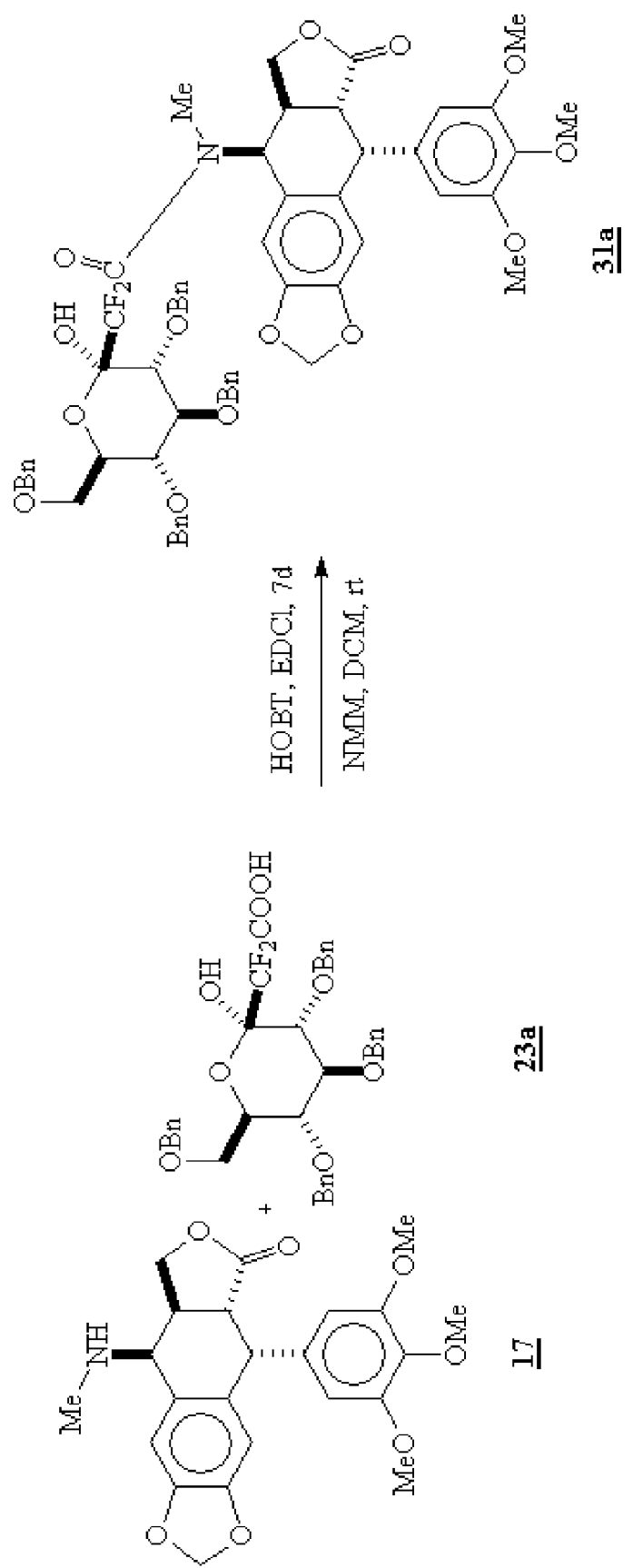
Figure 17:
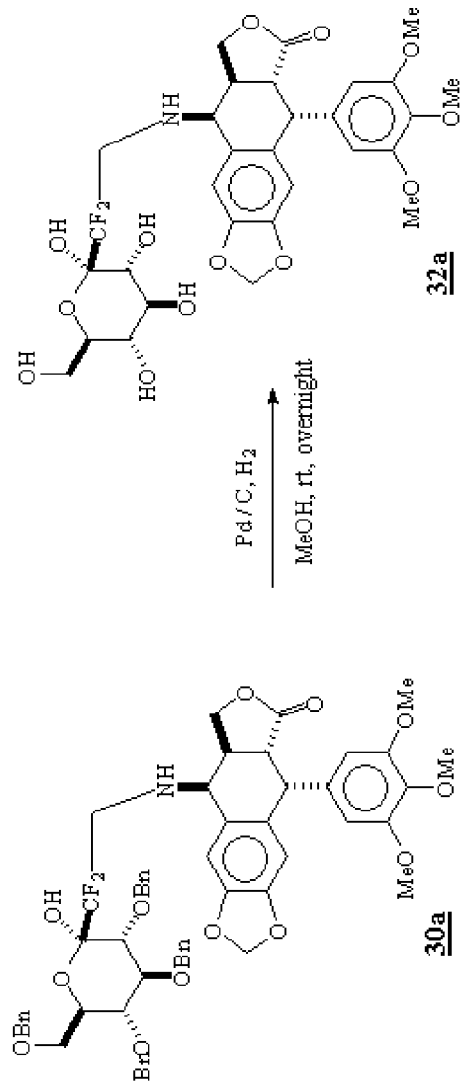
Figure 18:
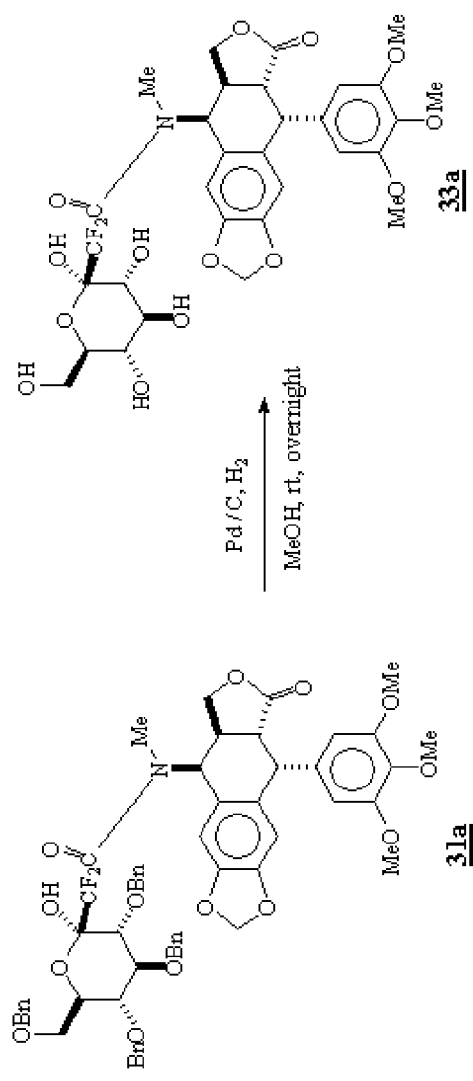
Figure 19:
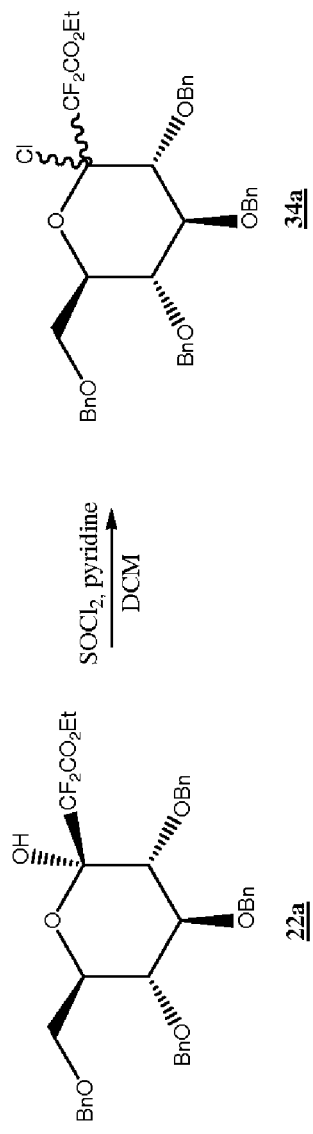
Figure 20:
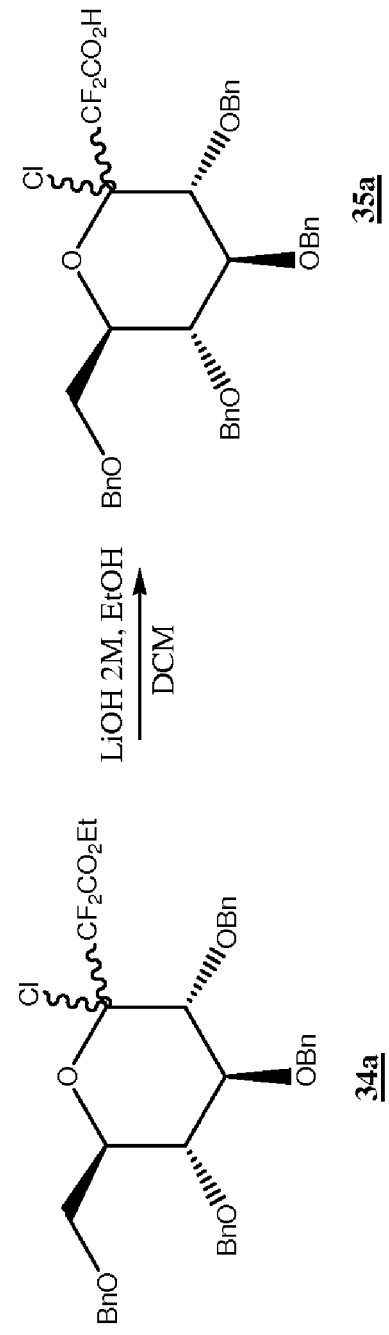
Figure 21:
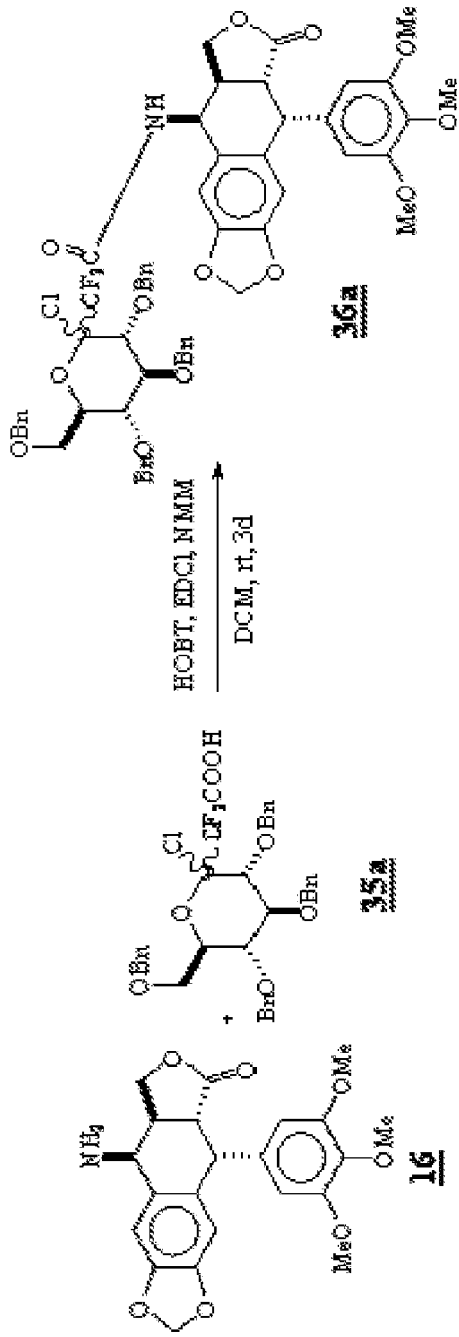
Figure 22:
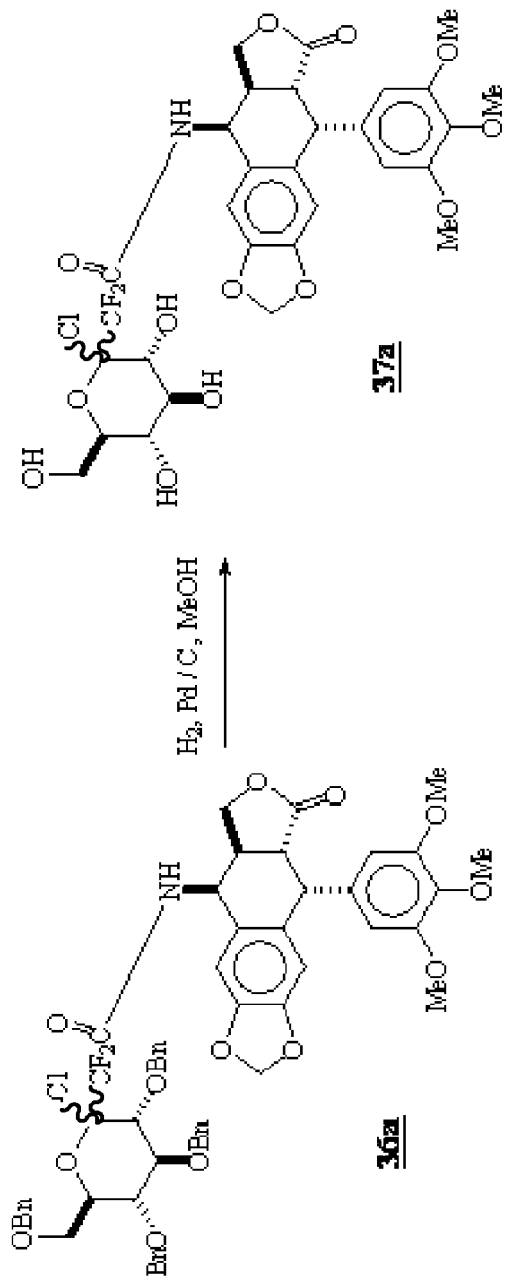
Figure 23:
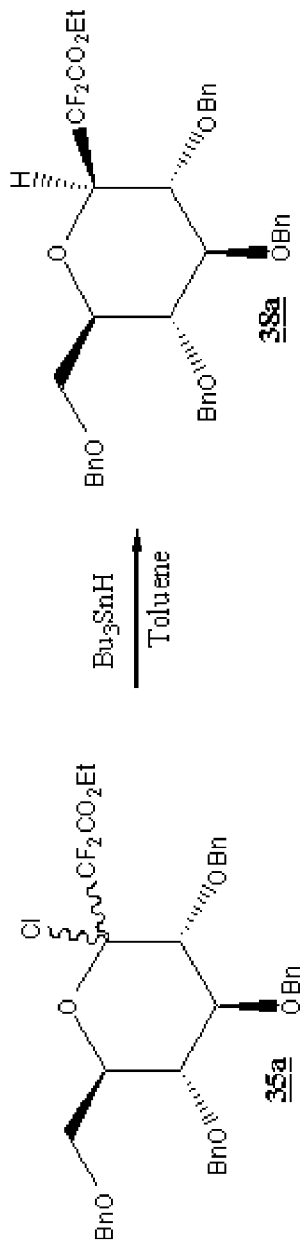
Figure 24:
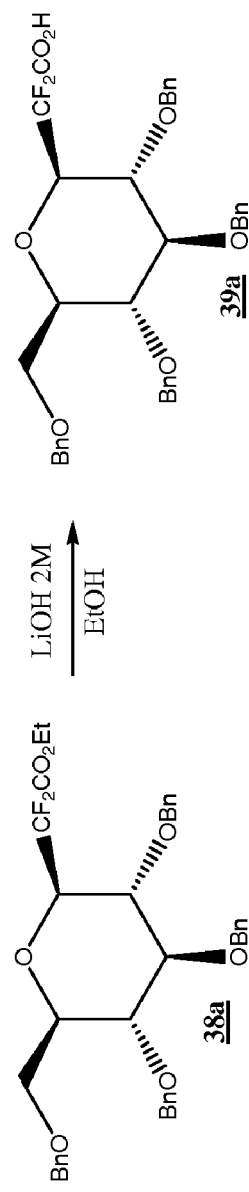
Figure 25:
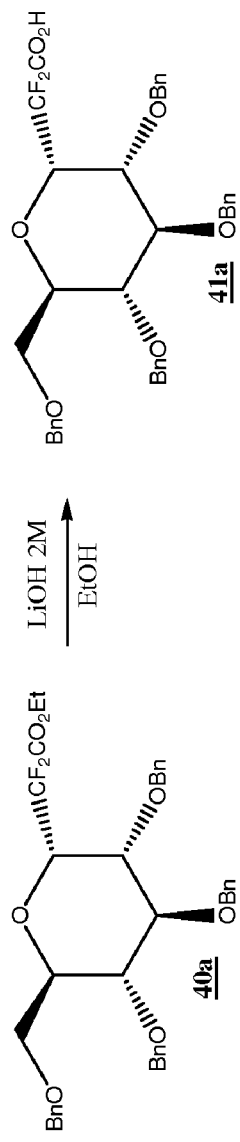
Figure 26:
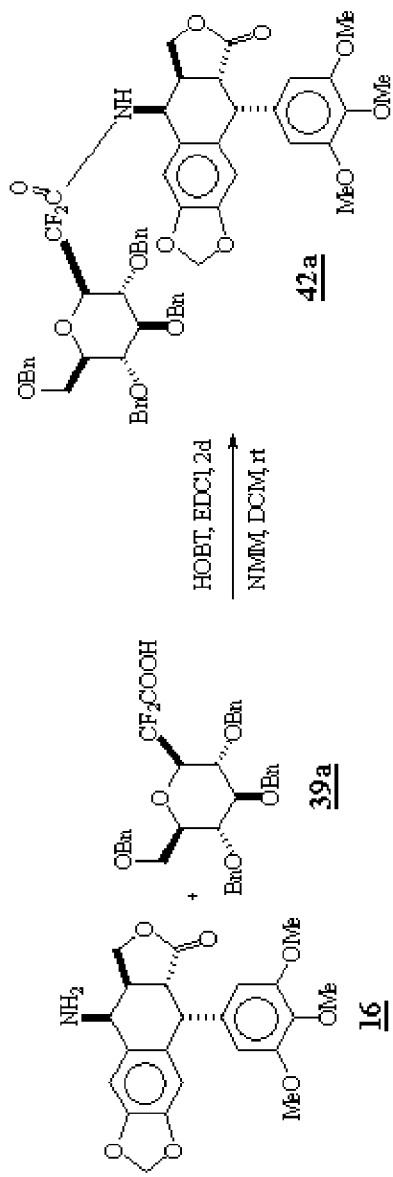
Figure 27:
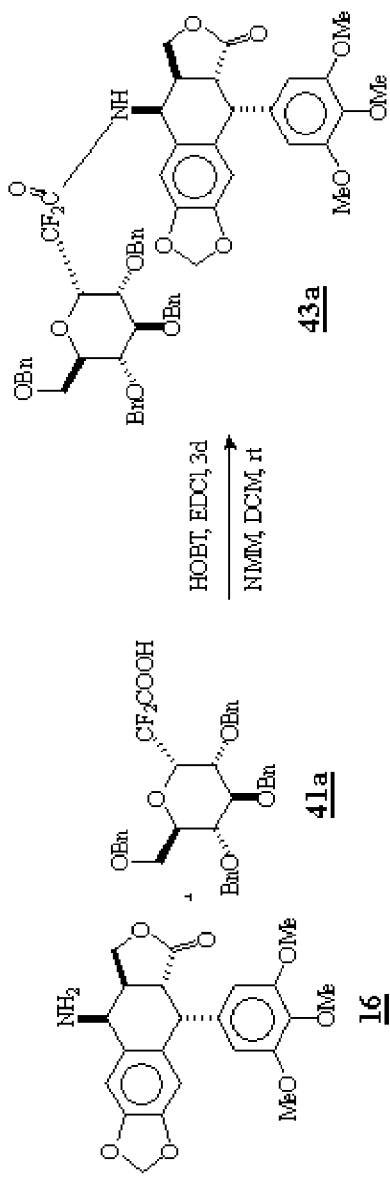
Figure 28:
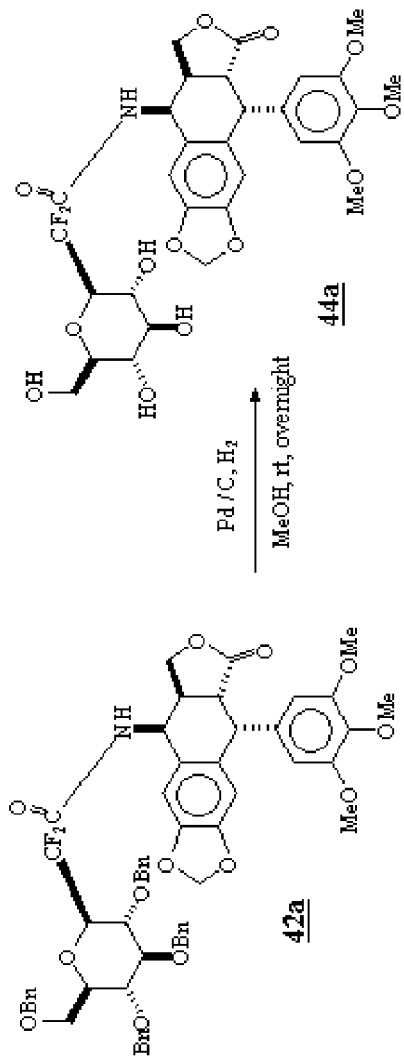
Figure 29:
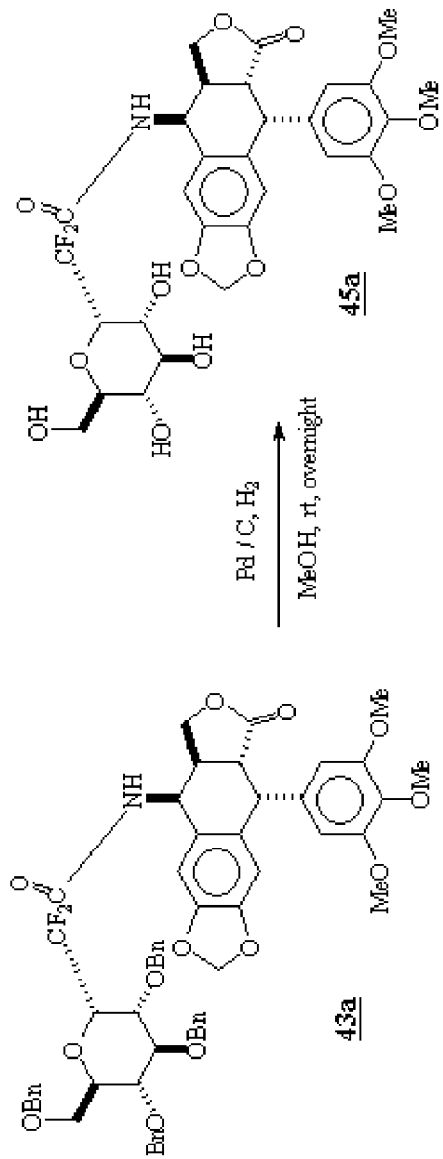
Figure 30:
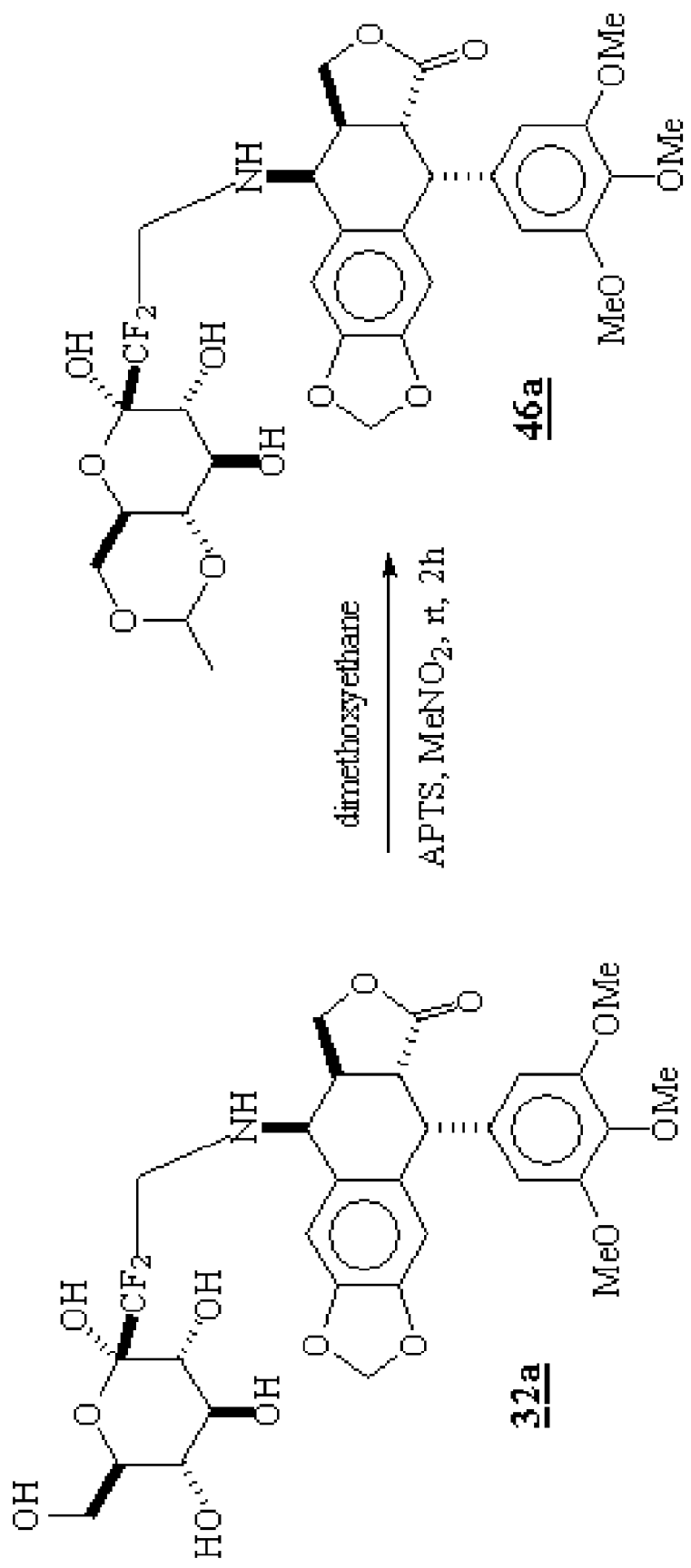

FIG. 8 is a reaction equation for obtaining compound 20a or 20b;
FIG. 9 is a reaction equation for obtaining compound 21a or 21b;
FIG. 10 is a reaction equation for obtaining compound 22a or 22b;
FIG. 11 is a reaction equation for obtaining compound 23a or 23b;
FIG. 12 is a reaction equation for obtaining compound 24a or 24b or else 25a or 25b;
FIG. 13 is a reaction equation for obtaining compound 26a or 26b or else 27a or 27b;
FIG. 14 is a reaction equation for obtaining compound 28a or 28b or else 29a or 29b;
FIG. 15 is a reaction equation for obtaining compound 30a;
FIG. 16 is a reaction equation for obtaining compound 31a.
FIG. 17 is a reaction equation for obtaining compound 32a.
FIG. 18 is a reaction equation for obtaining compound 33a.
FIG. 19 is a reaction equation for obtaining compound 34a.
FIG. 20 is a reaction equation for obtaining compound 35a.
FIG. 21 is a reaction equation for obtaining compound 36a.
FIG. 22 is a reaction equation for obtaining compound 37a.
FIG. 23 is a reaction equation for obtaining compound 38a.
FIG. 24 is a reaction equation for obtaining compound 39a.
FIG. 25 is a reaction equation for obtaining compound 41a.
FIG. 26 is a reaction equation for obtaining compound 42a.
FIG. 27 is a reaction equation for obtaining compound 43a.
FIG. 28 is a reaction equation for obtaining compound 44a.
FIG. 29 is a reaction equation for obtaining compound 45a.
FIG. 30 is a reaction equation for obtaining compound 46a.

DESCRIPTION OF THE PREFERRED EMBODIMENTS

The encountered abbreviations are thus defined as:

| eq.: equivalent | g: gram | Hz: Hertz |
|---|---|---|
| mg: milligram | MHz: megahertz | min: minute |
| mL: milliliter | mmol: millimole | µmol: micromole |
| nmol: nanomole | app: apparent | |

The characteristics of the apparatuses used for carrying out analyses of all the compounds described in the present application are indicated below:

The $^1$H, $^{13}$C, $^{19}$F NMR spectra were recorded on BRUKER DPX 300 and DPX 600 spectrometers. In $^1$H and $^{13}$C NMR, tetramethylsilane is used as an internal reference. In $^{19}$F NMR, the external reference is fluorotrichloromethane $CFCl_3$. The chemical displacements are expressed in parts per million (ppm), the coupling constants J in Hertz (Hz).

The following abbreviations were used:
for singlet, bs for broad singlet, d for doublet, t for triplet, q for quartet, m for multiplet or massive, dd for doublet of doublet . . . .

The mass spectra were obtained with a spectrophotometer of the type Micromass TOF-SPEC, E 20 kV, α-cyano. for Maldi ionization and of the type JEOL AX500, 3 kV, Canon FAB JEOL, Xe, 4 kV, limiting current 10 µA, Gly-NBA 50:50 for FAB ionization.

Separations by column chromatography are carried out under low pressure by following the techniques of chromatography on Kieselgel 60 silica (230-400 mesh, Merck).

Follow-up is ensured by thin layer chromatography (TLC) with Kieselgel 60F-254-0.25 mm plates. The ratio of the migration distance of a compound on a given medium over the distance of migration of an eluent is called the retention factor (Rf).

The figures hereafter describe the preparation of gem-difluorinated glycoconjugated compounds of formula 8 and reactions involving them for obtaining other active compounds:

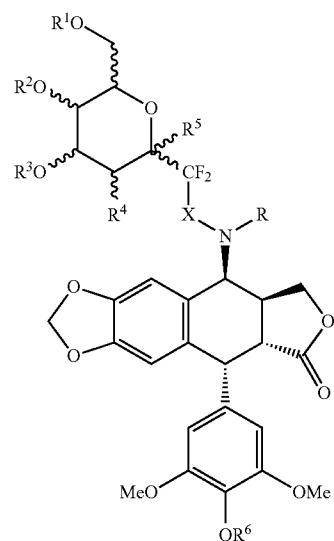

8 wherein R represents a hydrogen atom or a methyl group,
X represents a carbonyl —C═O group or a —CH$_2$ group,
$R^1$ and $R^2$, either identical or different, represent a hydrogen atom or a benzyl group,
$R^3$ represents a hydrogen atom or a benzyl group,
$R^4$ represents OR''', with R''' representing a hydrogen atom or a benzyl group,
$R^5$ represents a free hydroxyl group, a hydrogen or halogen atom such as the chlorine atom,
$R^6$ represents a hydrogen atom or a methyl group.

The target molecules 8 are obtained by a coupling reaction between two synthons: the glycoside unit 10 and the aminoepipodophyllotoxin unit 9:

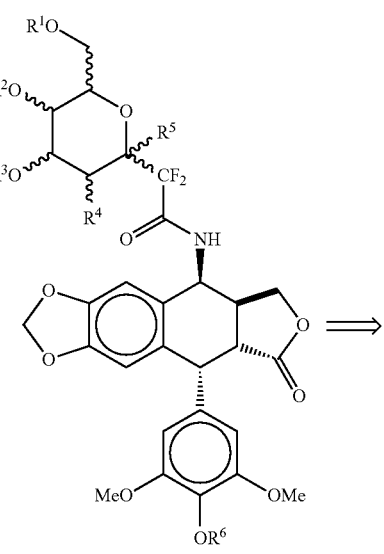

8

-continued

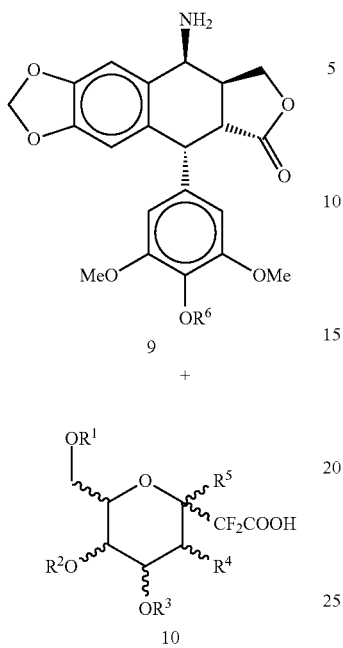

9

+

10

The layout of these functional units is accomplished in the following way.

Figure 1:
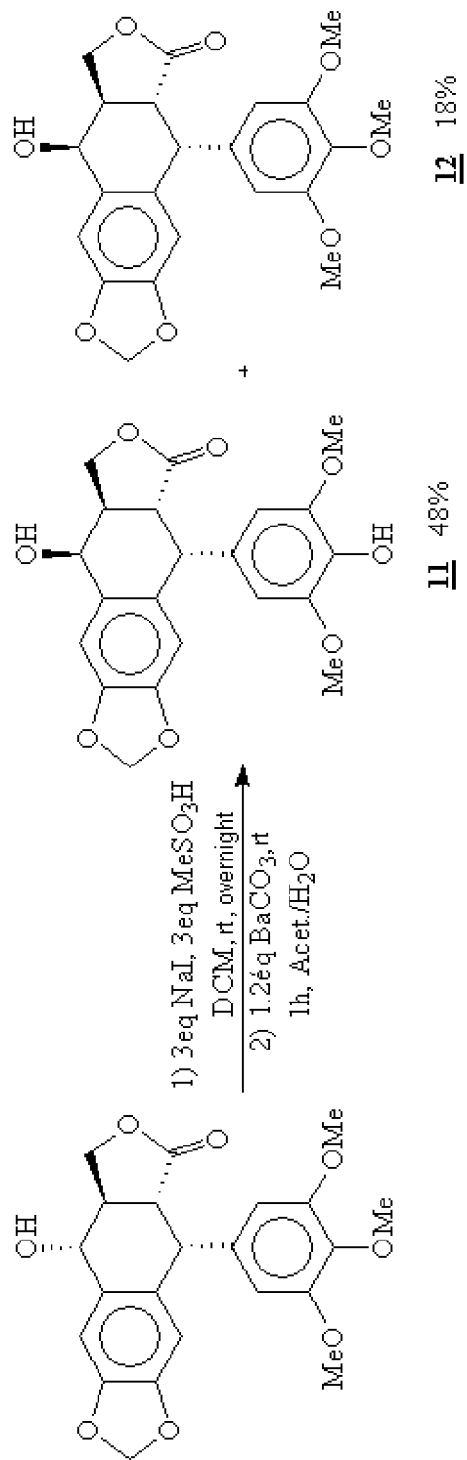
FIG. 1 is a reaction equation for obtaining compounds II and 12.

Starting with podophyllotoxin 1, steps for epimerization of the OH in position 4 and dimethylation of OMe in position 4' are conducted so as to lead to demethylepipodophyllotoxin 11, but the epimerized but non-dimethylated product is also observed in the medium: epipodophyllotoxin 12 (FIG. 1).

Figure 3:
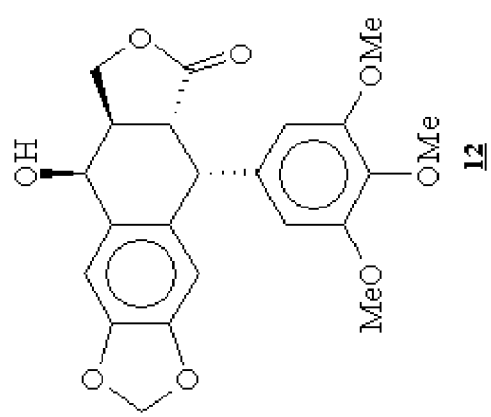
FIG. 3 is a reaction equation for obtaining compound 14.
Figure 3:
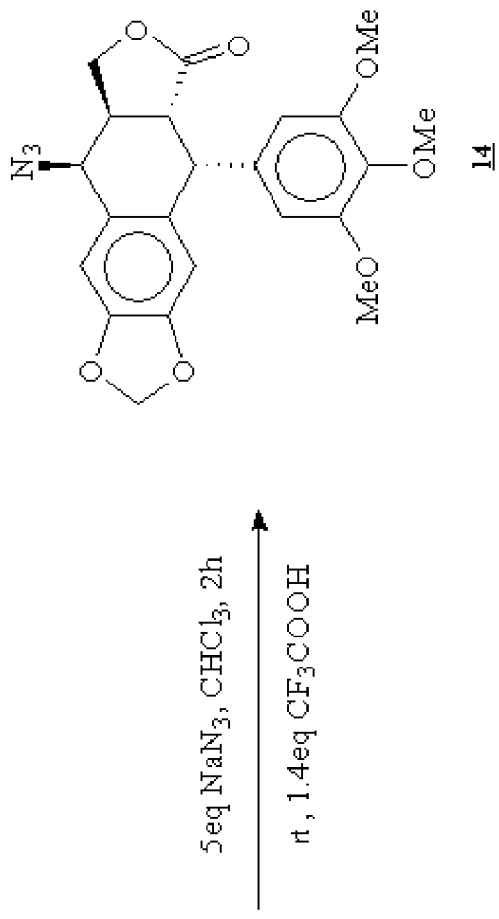
Figure 4:
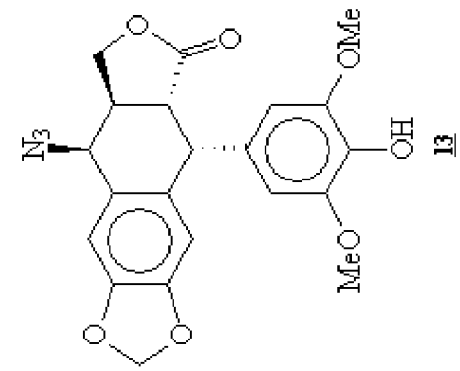
FIG. 4 is a reaction equation for obtaining compound 15.
Figure 4:
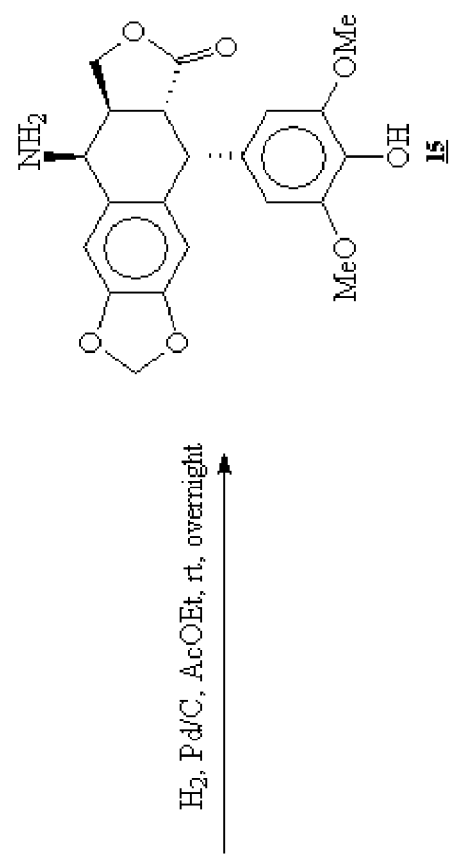
Figure 5:
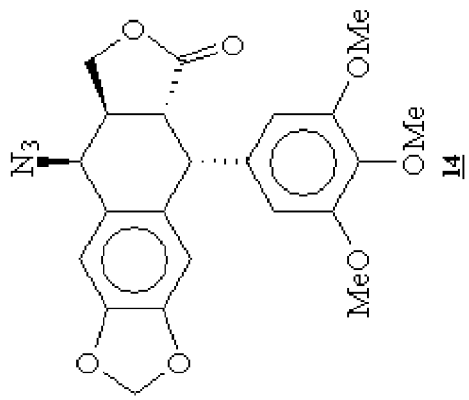
FIG. 5 is a reaction equation for obtaining compound 16.
Figure 5:
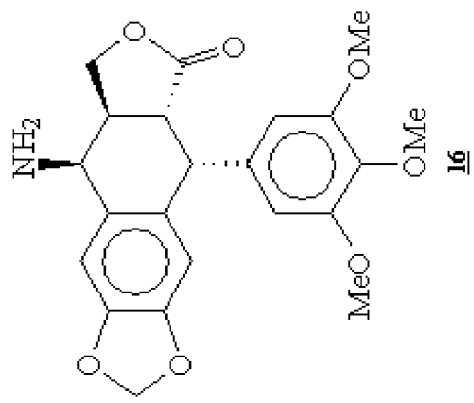

On both of these compounds, the OH in position 4 is then substituted with an azido group (FIGS. 2 and 3) which is then reduced to an amine group (FIGS. 4 and 5).

Synthesis of epipodophyllotoxin 12 and of 4'-demethylepipodophyllotoxin 11 (FIG. 1)

Podophyllotoxin 1 (1.00 g; 2.29 mmol; 1 eq.) is dissolved in dry dichloromethane DCM (30 mL). Sodium iodide (1.03 g; 6.88 mmol; 3 eq.) is added and the reaction medium is stirred for 5 minutes. Methane-sulfonic acid $MeSO_3H$ (0.66 g; 0.45 mL; 6.88 mmol; 3 eq.) is slowly added at 0° C. and the mixture is then warmed up to room temperature and stirred overnight. $BaCO_3$ (0.54 g; 2.75 mmol; 1.2 eq.) and a water/acetone mixture (25 mL) are added into the medium at 0° C. which is then stirred for one hour at room temperature. A 10% sodium thiosulfate $Na_2S_2O_3$ aqueous solution (30 mL) is added to the reaction, which is then extracted with dichloromethane (3×30 mL). The organic phases are collected and washed with a saturated solution (50 mL) of sodium chloride, dried on magnesium sulfate $MgSO_4$ and concentrated under reduced pressure.

The resulting red solid is purified by chromatography on silica gel with a dichloromethane/ethyl acetate mixture as en eluent, in proportions of eight to two.

Epipodophyllotoxin 12 (0.17 g) and 4'-demethylepipodophyllotoxin 11 (0.44 g) are isolated as pale pink solids with a yield of 66% by weight.

Characterization of Epipodophyllotoxin 12

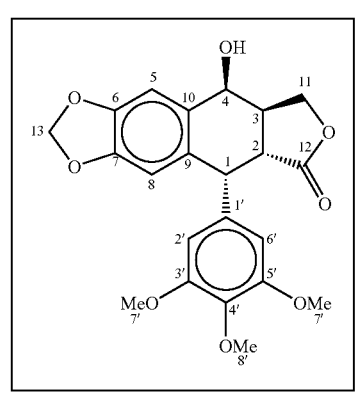

Rf=0.38, eluent: DCM/ethyl acetate (8:2).

$^1$H NMR (CDCl$_3$, 300 MHz)

2.77 (dddd, 1H, $^3J_{H3-H2}$ 14.1, $^3J_{H3-H11}$ 4.1, $^3J_{H3-H4}$ 3.3, $^3J_{H3-H11}$ 1.8, H3); 3.21 (dd, 1H, $^3J_{H2-H3}$ 14.1, $^3J_{H2-H1}$ 5.1, H2); 3.67 (s, 6H, H7'×6); 3.73 (s, 3H, H8'×3); 4.28 (d, 1H, $^3J_{H11-H3}$ 1.8, H11); 4.31 (d, 1H, $^3J_{H11-H3}$ 4.1, H11); 4.54 (d, 1H, $^3J_{H1-H2}$ 5.1, H1); 4.79 (d, 1H, $^3J_{H4-H3}$ 3.3, H4); 5.91 (dd, 2H, $^2J_{H13-H13}$ 8.1, 1.3, H13); 6.21 (s, 2H, H2', H6'); 6.48 (s, 1H, H8); 6.81 (s, 1H, H5).

$^{13}$C NMR (CDCl$_3$, 75 MHz)

38.1 (C3); 40.5 (C2); 43.8 (C1); 56.1 (2C; C7'×2); 60.6 (C8'); 66.6 (C4); 67.5 (C11); 101.5 (C13); 107.7 (2C; C2'; C6'); 108.8 (C5); 110.4 (C8); 131.7; 131.8; 134.9; 137.0; 147.4 (C7); 148.4 (C6); 152.4 (2C; C3'; C5'); 174.9 (C12).

Characterization of 4'-demethylepipodophyllotoxin 11

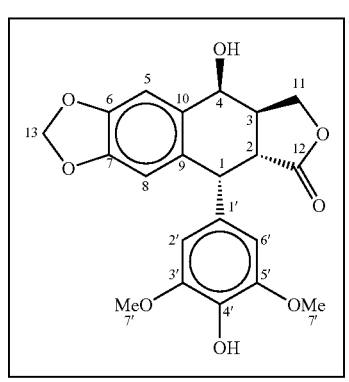

Rf=0.23, eluent: DCM/ethyl acetate (8:2).

$^1$H NMR (CDCl$_3$, 300 MHz)

2.75 (dddd, 1H, $^3J_{H3-H2}$ 14.1, $^3J_{H3-H11}$ 6.3, $^3J_{H3-H11}$ 3.8, $^3J_{H3-H4}$ 3.5, H3); 3.19 (dd, 1H, $^3J_{H2-H3}$ 14.1, $^3J_{H2-H1}$ 5.1, H2); 3.70 (s, 6H, H7'×6); 4.27 (d, 1H, $^3J_{H11-H3}$ 3.8, H11); 4.31 (d, 1H, $^3J_{H1-H3}$ 6.3, H11); 4.54 (d, 1H, $^3J_{H1-H2}$ 5.1, H1); 4.79 (d, 1H, $^3J_{H4-H3}$ 3.5, H4); 5.35 (s, 1H, OH); 5.92 (dd, 2H, $^3J_{H13-H13}$ 8.8, 1.3, H13); 6.22 (s, 2H, H2', H6'); 6.48 (s, 1H, H8); 6.81 (s, 1H, H5).

$^{13}$C NMR (CDCl$_3$, 75 MHz)

38.6 (C3); 41.0 (C2); 44.1 (C1); 56.8 (2C; C7'×2); 67.2 (C4); 68.0 (C11); 101.9 (C13); 108.2 (2C; C2'; C6'); 109.3 (C5); 110.9 (C8); 130.9; 132.2; 132.5; 134.4; 146, (2C; C3'; C5'); 147.8 (C7); 148.9 (C6); 175.5 (C12).

Figure 2:
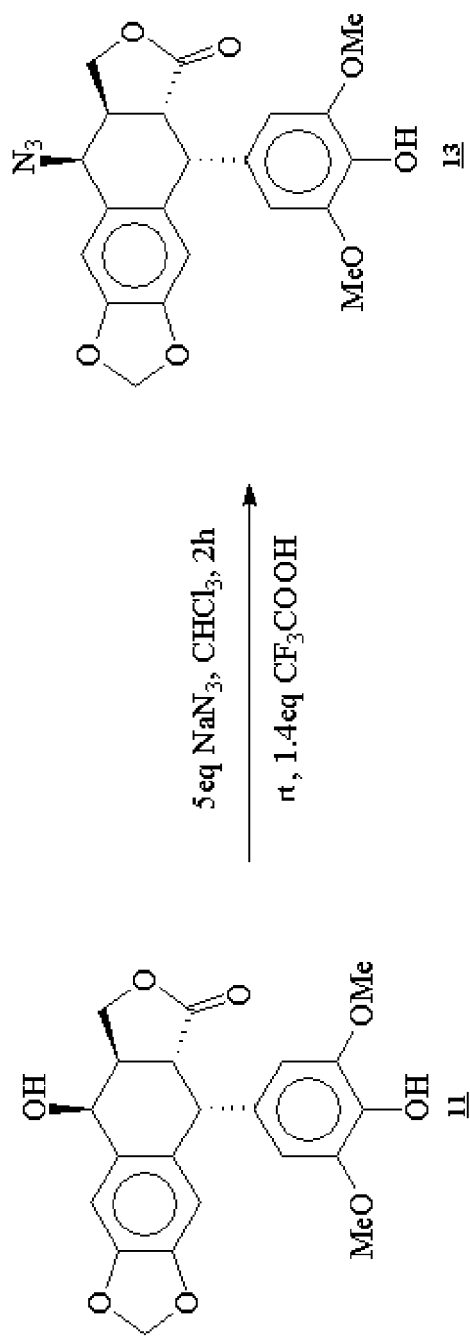
FIG. 2 is a reaction equation for obtaining compound 13.

Synthesis of 4β-azido-4-deoxy-4'-demethylepipodophyllotoxin 13 (FIG. 2)

On a solution containing 4'-demethylepipodophyllotoxin 11 (1.65 g; 4.1 mmol; 1 eq.) and sodium nitride NaN$_3$ (1.4 g; 21.0 mmol; 5 eq.) in chloroform CHCl$_3$ (15 mL), trifluoroacetic acid CF$_3$COOH (4.5 mL; 5.8 mmol; 1.4 eq.) is added dropwise and the medium is stirred for 2 h at room temperature. A saturated solution (10 mL) of sodium hydrogencarbonate NaHCO$_3$ is added, the mixture is thus extracted with chloroform (3×20 mL). The organic phases are combined, washed with water (40 mL), dried on magnesium sulfate MgSO$_4$ and concentrated in order to obtain 4β-azido-4-deoxy-4'-demethylepipodophyllotoxin 13 as a yellow solid with quantitative yield. The product is sufficiently pure for it to be used for the next step without any further purification.

Characterization of 4β-azido-4-deoxy-4'-demethylepipodophyllotoxin 13

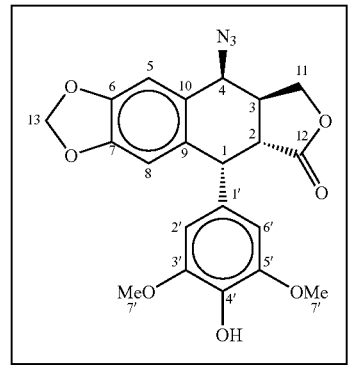

13

Rf=0.56, eluent: dichloromethane/ethyl acetate (8:2).
$^1$H NMR (CDCl$_3$, 300 MHz)
2.86 (m, 1H, H3); 3.10 (dd, 1H, $^3J_{H2\text{-}H3}$ 13.8, $^3J_{H2\text{-}H1}$ 5.2, H2); 3.70 (s, 6H, H7'×6); 4.23 (d$_{app}$, 2H, $^3J_{H11\text{-}H3}$ 9.4, H11×2); 4.55 (d, 1H, $^3J_{H1\text{-}H2}$ 5.2, H1); 4.70 (d, 1H, $^3J_{H4\text{-}H3}$ 3.7, H4); 5.36 (s, 1H, —OH); 5.95 (dd, 2H, $^3J_{H13\text{-}H13}$ 6.3, 1.2, H13); 6.20 (s, 2H, H2', H6'); 6.52 (s, 1H, H8); 6.73 (s, 1H, H5).
$^{13}$C NMR (CDCl$_3$, 75 MHz)
35.8 (C3); 40.3 (C2); 42.5 (C1); 55.5 (2C, C7'×2); 58.2 (C4); 66.8 (C11); 100.8 (C13); 106.8 (2C, C2', C6'); 107.6 (C5); 110.1 (C8); 125.8; 129.5; 131.3; 133.2; 145.4 (2C, C3', C5'); 146.7 (C7); 147.9 (C6); 173.1 (C12).

Synthesis of 4β-azido-4-deoxyepipodophyllotoxin 14 (FIG. 3)

In a solution containing epipodophyllotoxin 12 (670 mg; 1.6 mmol; 1 eq.) and sodium nitride NaN$_3$ (530 mg; 8.1 mmol; 5 eq.) in chloroform CHCl$_3$ (8 mL), trifluoroacetic acid CF$_3$COOH (0.55 mL; 2.2 mmol; 1.4 eq.) is added dropwise and the medium is stirred for two hours in room temperature. A saturated solution (10 mL) of sodium hydrogencarbonate NaHCO$_3$ is added, the mixture is then extracted with chloroform (3×15 mL). The organic phases are combined, washed with water (30 mL), dried on magnesium sulfate MgSO$_4$ concentrated in order to obtain 4β-azido-4-deoxyepipodophyllotoxin 14 as a yellow solid with quantitative yield. The product is sufficiently pure for it to be used for the next step without any further purification.

Characterization of 4β-azido-4-deoxyepipodophyllotoxin 14

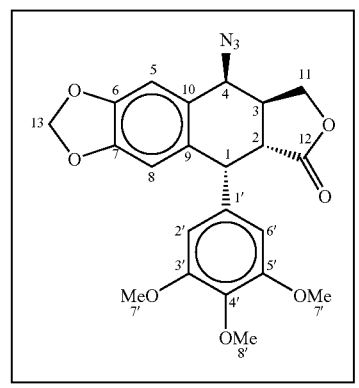

14

Rf=0.86; eluent: dichloromethane/ethyl acetate (8:2).
$^1$H NMR (CDCl$_3$, 300 MHz)
2.84-2.91 (m, 1H, H3); 3.12 (dd, 1H, $^3J_{H2\text{-}H3}$ 13.8, $^3J_{H2\text{-}H1}$ 5.2, H2); 3.67 (s, 6H, H7'×6); 3.73 (s, 3H, H8'×3); 4.24 (d, 1H, $^3J_{H11\text{-}H3}$ 2.5, H11); 4.26 (d, 1H, $^3J_{H11\text{-}H11}$ 0.6, H11); 4.56 (d, 1H, $^3J_{H1\text{-}H2}$ 5.2, H1); 4.71 (d, 1H, $^3J_{H4\text{-}H3}$ 3.7, H4); 5.95 (dd, 2H, $^3J_{H13\text{-}H13}$ 5.5, 1.3, H13); 6.19 (s, 2H, H2', H6'); 6.52 (s, 1H, H8); 6.74 (s, 1H, H5).
$^{13}$C NMR (CDCl$_3$, 75 MHz)
38.7 (C3); 43.0 (C2); 45.4 (C1); 58.1 (2C, C7'×2); 61.4 (C4); 62.5 (C8'); 69.4 (C11); 103.8 (C13); 110.0 (2C, C2', C6'); 110.6 (C5); 112.9 (C8); 128.6, 133.9; 136.8; 139.1; 149.1 (C7); 150.8 (C6); 154.4 (2C, C3', C5'); 175.9 (C12).

Synthesis of 4β-amino-4-deoxy-4'-demethylepipodophyllotoxin 15 (FIG. 4)

4β-azido-4-deoxy-4'-demethylepipodophyllotoxin 13 (354 mg; 0.83 mmol) is dissolved in ethyl acetate (25 mL) and palladium on charcoal is added. The reaction medium is placed under a hydrogen atmosphere and stirred for one night at room temperature. The mixture is filtered and concentrated under reduced pressure so as to obtain a solid which is purified by flash chromatography on silica gel with a dichloromethane/ethyl acetate mixture as an eluent in proportions of eight to two in order to obtain 4β-amino-4-deoxy-4'-demethylepipodophyllotoxin 15 as a white solid with a yield of 67% by weight.

Characterization of 4β-amino-4-deoxy-4'-demethyl-epipodophyllotoxin 15

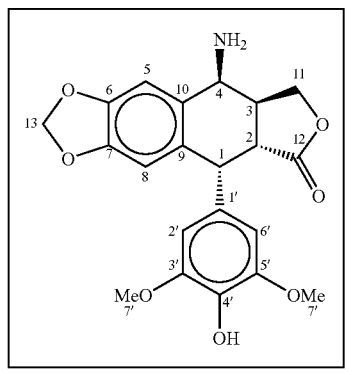

Rf=0.21; eluent: chloroform/methanol (19:1).

$^1$H NMR (CDCl$_3$, 300 MHz)

2.57-2.82 (m, 3H, H3, NH$_2$); 3.21 (dd, 1H, $^3J_{H2\text{-}H3}$ 14.1, $^3J_{H2\text{-}H1}$ 5.2, H2); 3.69 (s, 6H, H7'×6); 4.13 (d, 1H, $^3J_{H4\text{-}H3}$ 4.0, H4); 4.22 (d$_{app}$, 2H, $^3J_{H11\text{-}H3}$ 9.6, H11×2); 4.48 (d, 1H, $^3J_{H1\text{-}H2}$ 5.2, H1); 5.88 (dd, 2H, $^3J_{H13\text{-}H13}$ 7.7, 1.2, H13); 6.23 (s, 2H, H2', H6'); 6.41 (s, 1H, H8); 6.74 (s, 1H, H5).

$^{13}$C NMR (CDCl$_3$, 75 MHz)

38.3 (C3); 40.7 (C2); 44.1 (C1); 49.3 (C4); 56.8 (2C, C7'×2); 68.6 (C11); 101.8 (C13); 108.4 (2C, C2', C6'); 109.4 (C5); 110.3 (C8); 131.5; 131.6; 134.3; 134.4; 146.8 (2C, C3', C5'); 147.7; 148.0; 175.9 (C12).

Synthesis of 4β-amino-4-deoxyepipodophyllotoxin 16 (FIG. 5)

4β-azido-4-deoxyepipodophyllotoxin 14 (1,150 mg; 2.62 mmol) is dissolved in ethyl acetate (25 mL) and palladium on charcoal is added. The reaction medium is placed under a hydrogen atmosphere and stirred overnight at room temperature. The mixture is filtered and concentrated under reduced pressure so as to obtain a solid which is purified by flash chromatography on silica gel with a dichloromethane/ethyl acetate mixture in proportions of eight to two so as to obtain 4β-amino-4-deoxyepipodophyllotoxin 16 as a pale yellow solid with a yield of 81% by weight.

Characterization of 4β-amino-4-deoxyepipodophyllotoxin 16

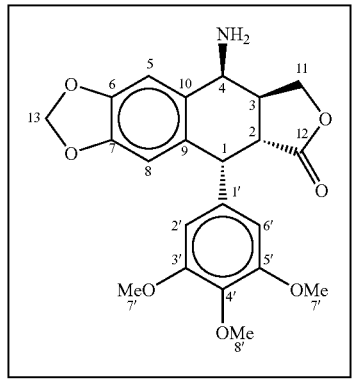

Rf=0.29, eluent: CHCl$_3$/methanol (19:1).

$^1$H NMR (CDCl$_3$, 300 MHz)

2.21 (ls, 2H, —NH$_2$); 2.75-2.85 (m, 1H, H3); 3.25 (dd, 1H, $^3J_{H2\text{-}H3}$ 14.1, $^3J_{H2\text{-}H1}$ 5.4, H2); 3.67 (s, 6H, H7'×6); 3.72 (s, 3H, H8'×3); 4.18 (d, 1H, $^3J_{H4\text{-}H3}$ 4.2, H4); 4.22 (dd, 1H, $^3J_{H11\text{-}H3}$ 8.8, $^3J_{H11\text{-}H11}$ 0.9, H11×2); 4.25 (s, 1H, H11); 4.49 (d, 1H, $^3J_{H1\text{-}H2}$ 5.4, H1); 5.88 (dd, 2H, $^3J_{H13\text{-}H13}$ 6.4, 1.3, H13); 6.22 (s, 2H, H2', H6'); 6.42 (s, 1H, H8); 6.77 (s, 1H, H5).

$^{13}$C NMR (CDCl$_3$, 75 MHz)

38.2 (C3); 40.6 (C2); 44.3 (C1); 49.4 (C4); 56.6 (2C, C7'×2); 61.1 (C8'); 68.5 (C11); 101.8 (C13); 108.6 (2C, C2', C6'); 109.1 (C5); 110.7 (C8); 131.6; 133.7; 136.0; 137.4; 147.8 (C7); 148.2 (C6); 152.9 (2C, C3', C5'); 175.6 (C12).

Figure 6:
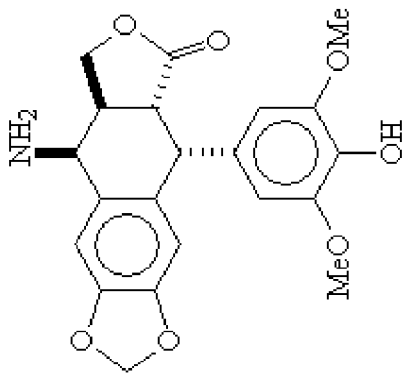
FIG. 6 is a reaction equation for obtaining compound 17.
Figure 6:
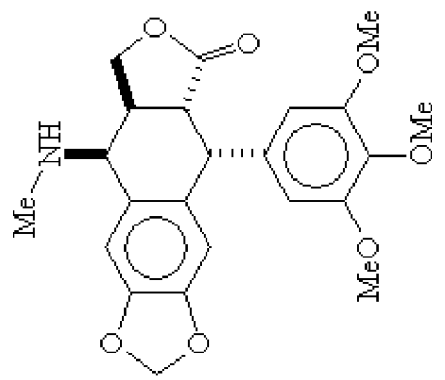

Synthesis of N-methyl-4β-amino-4-deoxyepipodophyllotoxin 17 (FIG. 6)

4β-amino-4-deoxy-4'-demethylepipodophyllotoxin 15 (115 mg; 0.29 mmol; 1 eq.) is dissolved in anhydrous tetrahydrofurane (5 mL) and slowly added to a sodium hydride solution (21 mg; 0.86 mmol; 3 eq.) in tetrahydrofurane (2 mL). The solution is thus stirred for 30 minutes at room temperature. Methyl iodide (123 mg; 0.86 mmol; 3 eq.) is added at room temperature and the reaction medium is stirred overnight. Water (10 mL) is added to stop the reaction. The mixture is then extracted with dichloromethane (3×10 mL). The organic phases are collected and washed with a saturated solution (20 mL) of sodium chloride, dried on magnesium sulfate MgSO$_4$ and concentrated under reduced pressure. The resulting yellow oil is purified by chromatography on silica gel with 100% ethyl acetate. N-methyl-epipodophyllotoxin 17 (54 mg) is isolated as a colorless oil with a yield of 44% by weight.

Characterization of N-methyl-4β-amino-4-deoxyepipodophyllotoxin 17

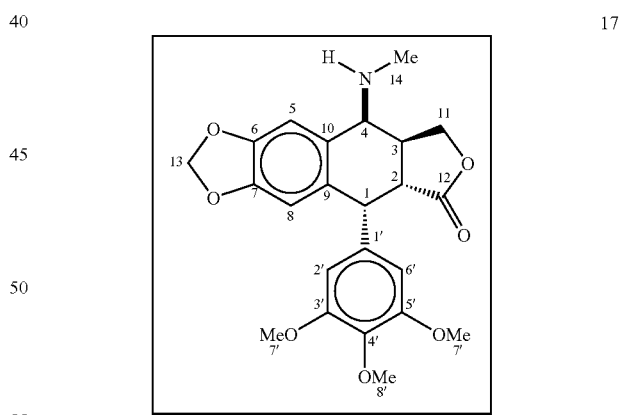

Rf=0.14, eluent: ethyl acetate.

$^1$H NMR (CDCl$_3$, 300 MHz)

1.95 (ls, 1H, N—H), 2.50 (ls, 1H, H2), 2.60-2.70 (dd, 1H, $^2J_{H11\text{-}H11}$ 9.4, 5.6, H3), 2.71 (s, 3H, H14×3), 3.59-3.65 (m, 2H, H11×2), 3.76 (s, 6H, H7'×6), 3.81 (s, 3H, H8'×3), 4.09 (s, 1H, H4), 4.29 (s, 1H, H1), 5.94 (dd, 2H, $^2J_{H13\text{-}H13}$ 12.7, 1.3, H13×2), 6.30 (s, 2H, H2', H6'), 6.48 (s, 1H, H8), 6.67 (s, 1H, H5).

$^{13}$C NMR (CDCl$_3$, 75 MHz)

27.6 (C14), 42.6 (C3), 45.9 (C1), 51.0 (C2), 55.9 (2C, C7'×2), 60.5 (C8'), 61.8 (C11), 61.8 (C4), 100.9 (C13), 105.7

(2C, C2', C6'), 107.0 (C5), 111.9 (C8), 128.8, 131.7, 136.4, 139.8, 145.4 (C7), 147.3 (C6), 152.8 (2C, C3', C5'), 175.2 (C12).

Mass spectrometry: 428 (M+H)+, 414 (M+H−Me)+.

The steps for benzylation of a sugar 18 (FIG. 7), for acid hydrolysis of the anomeric position of a compound 19 (FIG. 8), and for oxidation of a compound 20 (FIG. 9) lead to a lactone 21. On this lactone 21, introduction of the difluoroester unit onto a compound 22 is accomplished via a Reformatsky reaction (FIG. 10). This ester function is then saponified in order to obtain a compound 23 (FIG. 11) in view of the coupling step.

Figure 7:
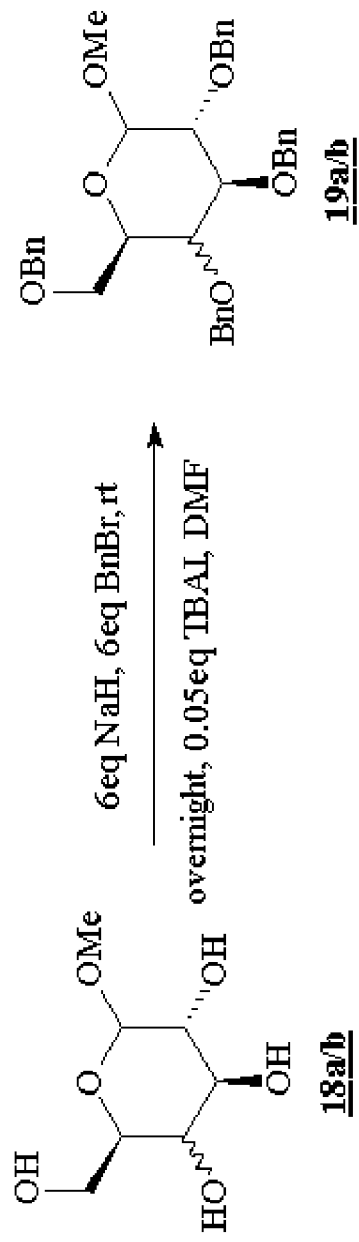
FIG. 7 is a reaction equation for obtaining compound 19a or 19b.

The experimental results are given as a glucose series, references of the products being followed by the letter a, and as a galactose series, references of the product being followed by the letter b:

Synthesis of 1-O-methyl-2,3,4,5,6-tetra-O-benzyl-D-glucopyranose 19a (FIG. 7)

In a flask under an argon atmosphere, 1-O-methyl-D-glucopyranose 18a (5 g; 26 mmol; 1 eq.) and tetrabutylammonium iodide nBu$_4$NI (0.5 g; 1.3 mmol; 0.05 eq.) are placed in a dimethylformamide DMF solution (250 mL). Sodium hydride NaH (3.7 g; 150 mmol; 6 eq.) is slowly introduced. Benzyl bromide BnBr (18 mL; 150 mmol; 6 eq.) is then added and the reaction is stirred for 24 h at room temperature. Water (200 mL) is slowly added and the aqueous phase is extracted with ether (3×150 mL). The organic phases are collected, dried on magnesium sulfate MgSO$_4$ and concentrated under reduced pressure. The product 19a is purified by silica column chromatography with a cyclohexane/ethyle acetate (9/1) mixture as an eluent.

The product 19a is isolated as colorless oil with a yield of 83% by weight.

Characterization of 19a

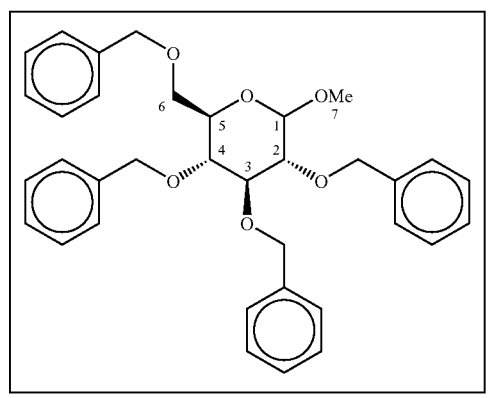

Rf=0.38, eluent: cyclohexane/ethyl acetate (9:1).

$^1$H NMR (CDCl$_3$, 300 MHz)

3.29 (s, 3H, H7); 3.45-3.67 (m, 5H, H2, H3, H4, 2×H6); 3.91 (t, 1H, $^3J_{H5-H6}$ 8.9, H5); 4.36-4.92 (m, 9H, 4×CH$_2$Ph, H1); 7.04-7.31 (m, 20H, H$_{Ar}$).

$^{13}$C NMR (CDCl$_3$, 75 MHz)

53.8 (C7); 67.1; 68.7; 72.1; 72.1; 73.7; 74.4; 76.3; 78.5; 80.8; 96.9 (C1); 126.3; 126.3; 126.4; 126.5; 126.6 (2C); 126.6; 126.8; 127.0 (2C); 127.1; 127.1; 136.6; 136.8; 136.9; 137.5.

Synthesis of 1-O-methyl-2,3,4,5,6-tetra-O-benzyl-D-galactopyranose 19b (FIG. 7)

In a flask under an argon atmosphere, 1-O-methyl-D-galactopyranose 18b (5 g; 26 mmol; 1 eq.) and tetrabutylammonium iodide (0.5 g; 1.3 mmol; 0.05 eq.) are placed in a DMF solution (250 mL). Sodium hydride (3.7 g; 150 mmol; 6 eq.) is slowly introduced. Benzyl bromide (18 mL; 150 mmol; 6 eq.) is added and the reaction is stirred for 24 h at room temperature. Water (200 mL) is slowly added and the aqueous phase is extracted with ether (3×150 mL). The organic phases are collected, dried on magnesium sulfate MgSO$_4$ and concentrated under reduced pressure.

The product 19b is purified by silica column chromatography with a cyclohexane/ethyl acetate (9/1) mixture as an eluent.

The product 19b is isolated as a colorless oil with a yield of 95% by weight.

Characterization of 19b

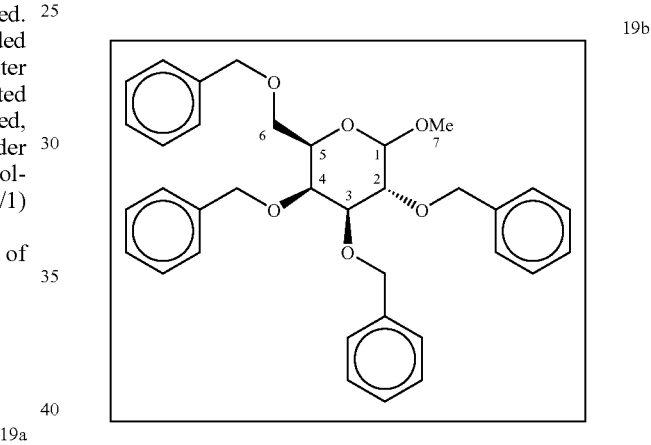

Rf=0.48, eluent: cyclohexane/ethyl acetate (8:2).

$^1$H NMR (CDCl$_3$, 300 MHz)

3.3 and 3.4 (2s, 3H, CH$_3$); 3.4-3.5 (m, 2H6, H5, 0.5H3$_\beta$); 3.7 (dd, 7.7-9.6, 0.5H, H2$_\beta$); 3.8-3.9 (m, 2H, 0.5H3$_\alpha$, H4); 4 (dd, 3.5__10.8, 0.5H, H2$_\alpha$); 4.2 (d, 7.7, 0.5H, H1$_\beta$); 4.6 (d, 3.5, 0.5H, H1$_\alpha$); 4.3-4.9 (m, 8H, H2, 4OCH$_2$Ph); 7.2 (m, 20H, H ar.)

$^{13}$C NMR (CDCl$_3$, 75.5 MHz)

55.8 and 57.5 (CH$_3$); 69.3 and 69.5 (C6); 69.6 (C5); 73.4; 73.7; 73.8 (C4); 73.9; 74.0; 74.8; 75.2; 75.6; 76.9; 79.5 and 80.1 (C2); 82.6 (C3); 99.2 and 105.4 (C1); 127.9-128 (Car.); 138-139 (Car. quat.).

Synthesis of 2,3,4,5,6-tetra-O-benzyl-D-glucopyranose 20a (FIG. 8)

In a flask containing 1-O-methyl-2,3,4,5,6-tetra-O-benzyl-D-glucopyranose 19a (6.4 g; 11.54 mmol) in an acetic acid solution (93 mL), a 3M solution of sulfuric acid (13 mL) is added and the reaction medium is heated to 110° C. for one hour. The reaction is cooled to room temperature. A white precipitate appears and the latter is filtered and dried in ambient air.

The compound 20a is obtained very pure as a white solid with a yield of 59% by weight and is directly engaged in the next step without any purification.

Characterization of 20a

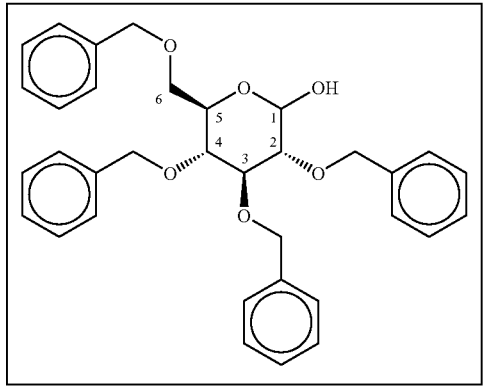

20a

Rf=0.35; eluent: cyclohexane/vinyl acetate (7:3).

NMR clearly shows two (α,β) anomers in carbon NMR.

$^1$H NMR (CDCl$_3$, 300 MHz)

3.58-3.66 (m, 4H, H2, H3, 2×H6); 3.94-4.06 (m, 2H, H4, H5); 4.44-4.96 (m, 8H, 4×CH$_2$Ph); 5.21 (d, 1H, $^3J_{H1-H2}$ 3.5, H1); 7.04-7.32 (m, 20H, H$_{Ar}$).

$^{13}$C NMR (CDCl$_3$, 75 MHz)

Majority anomer: 69.0 (C6); 70.6; 73.6; 73.9; 75.4; 76.1; 78.1; 80.4; 82.1; 91.7 (C1); 128.0; 128.1; 128.1; 128.3; 128.4; 128.4 (2C); 128.5; 128.6; 128.8 (2C); 128.8 (2C); 128.9; 138.2; 138.3; 138.6; 139.1.

Minority anomer: 69.3 (C6); 75.0; 75.2; 78.2; 83.5; 85.0; 97.9 (C1); 138.1; 138.4; 138.7; 138.9.

Melting point:

M.p.=151° C.

Synthesis of
2,3,4,5,6-tetra-O-benzyl-D-galactopyranose 20b
(FIG. 8)

In a flask containing 1-O-methyl-2,3,4,5,6-tetra-O-benzyl-D-galactopyranose 19b (6.4 g; 11.54 mmol) in an acetic acid solution (93 mL), a 3M solution of sulfuric acid (13 mL) is added and the reaction mixture is heated to 100° C. for one hour. The reaction is cooled to room temperature. The organic phases are collected and then washed with 100 mL with a saturated solution of sodium hydrogencarbonate NaHCO$_3$ and finally with 100 mL of water. The organic phase is then concentrated.

The thereby obtained raw product is purified by silica column chromatography with a cyclohexane/ethyl acetate mixture as an eluent in proportions of 8.5 to 1.5.

After concentration of the collected fractions, the product 20b appears as white crystals with a yield of 75% by weight.

Characterization of 20b

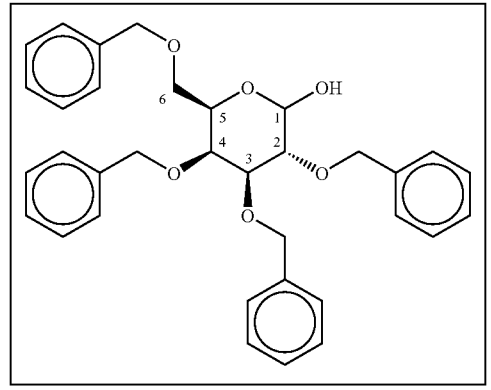

20b

Rf=0.67, eluent: cyclohexane/vinyl acetate (6:4).

NMR clearly shows two (α and β) anomers in carbon NMR.

Synthesis of the Lactone Derived from Glucose 21a
(FIG. 9)

In a flask containing 2,3,4,5,6-tetra-O-benzyl-D-glucopyranose 20a (2.9 g; 5.35 mmol) under an inert atmosphere, dimethylsulfoxide DMSO (19 mL) is added with acetic anhydride (13 mL). The reaction medium is stirred overnight at room temperature. A saturated NaHCO$_3$ solution (20 mL) is added and the mixture is extracted twice with ether (20 mL). The organic phases are collected and washed with water (10 mL) ten times, dried on magnesium sulfate and concentrated.

The reaction raw product is purified by chromatography on silica gel with a cyclohexane/ethyl acetate mixture as an eluent in proportions of eight to two.

The desired product 21a is thereby isolated as a colorless oil with a yield of 82% by weight.

Characterization of 21a

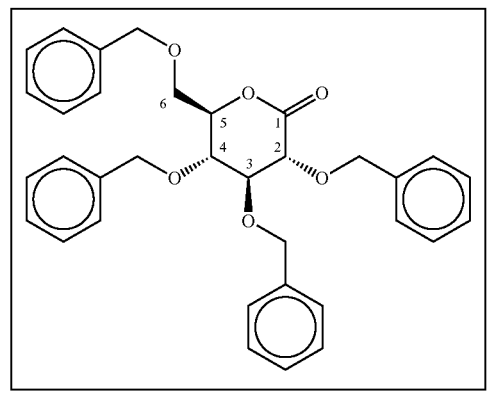

21a

TMC

Rf=0.61, eluent: cyclohexane/ethyl acetate (8:2).

$^1$H NMR (CDCl$_3$, 300 MHz)

3.65 (dd, 1H, $^3J_{H5-H6}$ 3.3, $^3J_{H6-H6}$ 11.0, H6); 3.72 (dd, 1H, $^3J_{H6-H5}$ 2.4, $^3J_{H6-H6}$ 11.0, H6); 3.89-3.95 (m, 2H, H3, H4);

4.13 (d, 1H, $^3J_{H2-H3}$ 6.8, H2); 4.44-4.74 (m, 8H, CH$_2$, H5); 4.96 (d$_{app}$, 1H, $^3$H 11.4); 7.15-7.34 (m, 20H, H$_{Ar}$).

RMN $^{13}$C (CDCl$_3$, 75 MHz)

68.6 (C6); 73.8; 74.0; 74.1; 74.1; 76.4; 77.8; 78.5; 81.2; 128.2; 128.3; 128.3; 128.4 (2C); 128.5; 128.7; 128.2 (2C); 128.8; 137.4; 137.9; 137.9; 138.0; 166.9 (C1).

Synthesis of the Lactone Derived from Galactose 21b (FIG. 9)

In a flask containing 2,3,4,5,6-tetra-O-benzyl-D-galactopyranose 20b (2.9 g; 5.35 mmol) under an inert atmosphere, DMSO (19 mL) is added with acetic anhydride (13 mL). The reaction medium is stirred overnight at room temperature. A saturated NaHCO$_3$ solution (20 mL) is added and the mixture is extracted twice with ether (20 mL). The organic phases are collected and washed with water (10 mL) ten times, dried on magnesium sulfate and concentrated.

The raw reaction product is purified by chromatography on silica gel with a cyclohexane/ethyl acetate mixture as an eluent in proportions of eight to two. The desired product 21b is thereby isolated as a white solid with a yield of 82% by weight.

Characterization of 21b

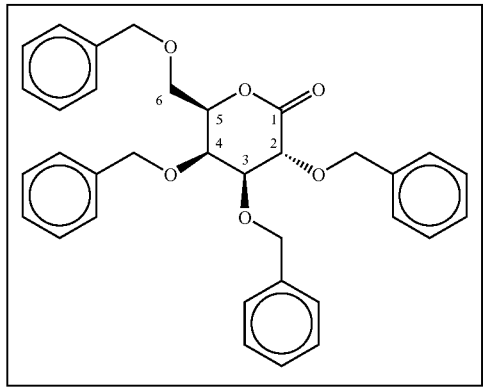

21b

Rf=0.61, eluent: cyclohexane/ethyl acetate (8:2).

$^1$H NMR (CDCl$_3$, 300 MHz)

3.6 (m, 2H, H6); 3.8 (dd, 2.1-9.6, 1H, H3); 4.1 (s, 1H, H4); 4.2 (m, 1H, H5); 4.4-5.1 (m, 9H, H2; 4OCH$_2$Bn H6); 7.2 (m, 20H, H ar.)

$^{13}$C NMR (CDCl$_3$, 75 MHz)

67.4 (C6); 72.4 (C4); 72.6 (OCH$_2$Bn); 73.5 (OCH$_2$Bn); 74.6 (OCH$_2$Bn); 75.1 (OCH$_2$Bn); 77.1 (C5); 77.2 (C2); 79.9 (C3); 127.4-128.3 (Car.); 137.2; 137.3; 137.6 (Car. quat.); 169.8 (CO).

Synthesis of the Gem-difluoroester Derived from Glucose 22a (FIG. 10)

In a flask under an inert atmosphere containing zinc (3.34 g; 51 mmol; 7 eq.) activated beforehand, tetrahydrofurane THF (60 mL) is added and the mixture is thereby refluxed by heating. A solution consisting of the lactone derived from 21a (3.94 g; 7.3 mmol; 1 eq.) and of ethyl bromodifluoroacetate (2.83 mL; 22 mmol; 3 eq.) in THF (60 mL) is slowly added to the previous mixture. The reaction is stirred under reflux for three hours. The mixture is cooled to room temperature, and a 1M solution of hydrochloric acid HCl (120 mL) is added, followed by the addition of dichloromethane (120 mL). The aqueous phase is extracted with dichloromethane (100 mL) twice. The organic phases are dried on magnesium sulphate MgSO$_4$, filtered and concentrated under reduced pressure. The residue is purified on a silica gel chromatographic column with a cyclohexane/ethyl acetate mixture as an eluent in proportions of eight to two.

The pure product 22a is isolated as a colorless oil with a yield of 75% by weight.

Characterization of 22a

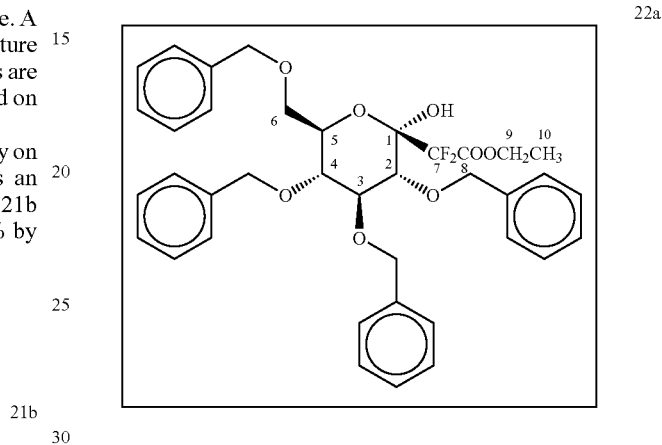

22a

Rf=0.35, eluent: cyclohexane/ethyl acetate (8:2).

$^1$H NMR (CDCl$_3$, 300 MHz)

1.30 (t, 3H, $^3J_{H9-H10}$ 7.1, H10); 3.63-3.81 (m, 3H, H3, 2×H6); 4.01-4.10 (m, 2H, H4, H5); 4.16 (s, 1H, H2); 4.29 (q, 2H, $^3J_{H9-H10}$ 7.1, 2×H9); 4.50-4.81 (m, 4H); 4.85-4.92 (m, 4H); 7.21-7.38 (m, 20H, H$_{Ar}$).

$^{13}$C NMR (CDCl$_3$, 75 MHz)

14.3 (C10); 63.7 (C9); 68.6 (C6); 73.0 (C2); 73.8; 75.5; 75.7; 76.4; 77.8 (C3); 78.6 (C4); 83.7 (C5); 96.5 (t; $^2J_{C-F}$ 25.5; C1); 128.0 (2C); 128.1 (2C); 128.1; 128.2; 128.3 (2C); 128.6; 128.7 (2C); 128.8 (2C); 128.8 (2C); 128.9 (2C); 137.9; 138.3; 138.7; 138.7; 163.3 (t; $^2J_{C-F}$ 30.3; C8).

$^{19}$F NMR (CDCl$_3$, 282 MHz)

−117.7 (d, 1F, $^2J_{F-F}$ 256.4); −120.1 (d, 1F, $^2J_{F-F}$ 256.4).

Synthesis of the Gem-difluoroester Derived from Galactose 22b (FIG. 10)

In a flask under an inert atmosphere containing zinc (3.34 g; 51 mmol; 7 eq.) activated beforehand, THF (60 mL) is added and the mixture is then refluxed by heating. A solution consisting of the lactone derived from the galactose 21b (3.94 g; 7.3 mmol; 1 eq.) and of ethyl bromodifluoroacetate (2.83 mL; 22 mmol; 3 eq.) in THF (60 mL) is slowly added to the previous mixture. The reaction is stirred under reflux for three hours. The mixture is cooled to room temperature and a 1M solution of hydrochloric acid HCl (120 mL) is added, followed by addition of dichloromethane (120 mL). The aqueous phase is extracted with dichloromethane (100 mL) twice. The organic phases are dried on magnesium sulfate MgSO$_4$, filtered and concentrated under reduced pressure.

The residue is purified on a silica gel chromatographic column with a cyclohexane/ethyl acetate mixture as an eluent in proportions of eight to two. The pure product 22b is isolated as a white solid with a yield of 82% by weight.

Characterization of 22b

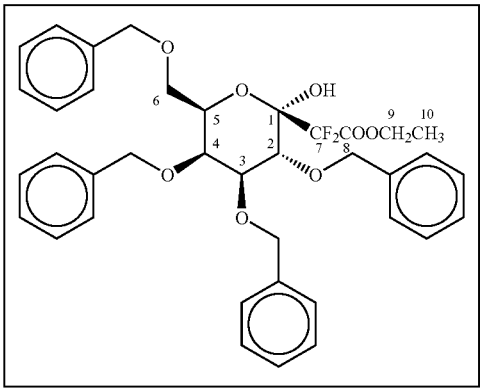

Rf=0.35, eluent: cyclohexane/ethyl acetate (8:2).
$^1$H NMR (CDCl$_3$, 300 MHz)
1.1 (t, 7.2, 3H, CH$_3$); 3.4-3.5 (m, 2H, H6); 3.7-3.8 (dd, 2.5-9.5, 1H, H3); 3.8 (d, 2, 1H, H4); 4-4.1 (m, 3H, H5; CH$_2$); 4.25-4.85 (m, 9H, H2; 4OCH$_2$Bn); 7.2 (m, 20H, Har).
$^{13}$C NMR (CDCl$_3$, 75 MHz)
14.2 (CH$_3$); 63.6 (CH$_2$); 68.6 (C6); 71.7 (C5); 73.2 (OCH$_2$Bn); 73.9 (OCH$_2$Bn); 74.1 (C4); 74.9 (OCH$_2$Bn); 75.1 (C2); 75.8 (OCH$_2$Bn); 81.2 (C3); 96.9 (t, 27 Hz, C1); 113 (t, 264 Hz, CF$_2$); 128.0-128.9 (Car.); 138.2; 138.3; 138.6; 139.1 (Car. quat.); 163.3 (t, 31 Hz, CO$_2$Et).
$^{19}$F NMR (CDCl$_3$, 282 MHz)
−118.4 (d, J$_{F-F}$=256 Hz); −120.2 (d, J$_{F-F}$=256 Hz).

Synthesis of the Gem-difluoroacid Derived from Glucose 23a (FIG. 11)

In a flask under an inert atmosphere containing the gem-difluoroester derived from glucose 22a (615 mg; 0.93 mmol; 1 eq.) in solution in THF (5 mL), an aqueous solution of lithine (2M; 2 eq.) is added and the mixture is stirred overnight at room temperature. The mixture is concentrated and dissolved in dichloromethane (5 mL), it is then acidified with a 1M solution of hydrochloric acid HCl (50 mL). The mixture is extracted with dichloromethane (3×25 mL), and the organic phases are combined, washed with a saturated solution of sodium chloride NaCl and directly concentrated.

The acid 23a is isolated with a yield of 90% by weight as a colorless oil which may be directly used for the next step without any additional purification.

Characterization of 23a

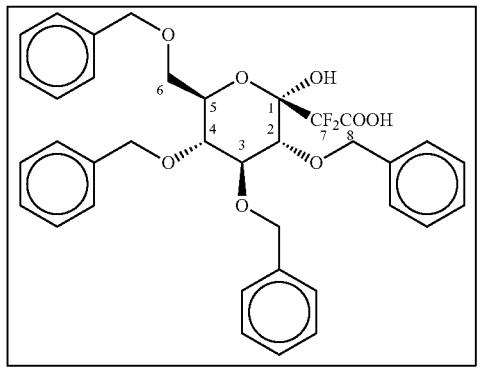

Rf=0.50, eluent: dichloromethane/methanol (9:1).
$^1$H NMR (CDCl$_3$, 300 MHz)
3.36-3.45 (m; 2H; H3; H6); 3.58-3.63 (m; 1H; H6); 3.88 (m; 2H; H4; H5); 4.00 (m; 1H; H2); 4.38 (m; 8H); 6.06 (ls; 2H; OH; COOH); 7.03-7.28 (m; 20H; H$_{Ar}$).
$^{13}$C NMR (CDCl$_3$, 75 MHz)
68.0 (C6); 71.4 (C2); 73.0; 74.9; 75.1; 75.9; 77.2 (C3); 77.9 (C4); 82.1 (C5); 94.9 (t; $^2$J$_{C-F}$ 26.8; C1); 126.6; 126.7; 126.9; 127.0; 127.0; 127.3; 127.3; 127.4; 127.5; 135.6; 136.2; 136.4; 137.1,
$^{19}$F NMR (CDCl$_3$, 282 MHz)
−117.2 (d, 1F, $^2$J$_{F-F}$ 258.6); −119.0 (d, 1F, $^2$J$_{F-F}$ 258.6).

Synthesis of the Gem-difluoroacid Derived from Galactose 23b (FIG. 11)

In a flask under an inert atmosphere containing the gem-difluoroester derived from galactose 22b (615 mg; 0.93 mmol; 1 eq.) in solution in THF (5 mL), an aqueous solution of lithine LiOH (2M; 2 eq.) is added and the mixture is stirred overnight at room temperature. The medium is concentrated and dissolved in dichloromethane (5 mL), it is then acidified with a 1M solution of hydrochloric acid HCl (50 mL). The mixture is extracted with dichloromethane (3×25 mL), and the organic phases are combined, washed with a saturated solution of sodium chloride NaCl and directly concentrated.

The acid 23b is isolated with a quantitative yield as a colorless oil which may be directly used for the next step without any additional purification.

Characterization of 23b

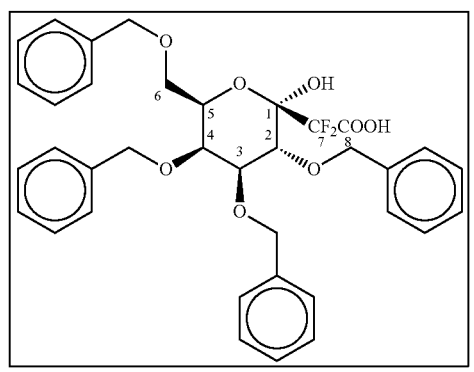

Rf=0.50, eluent: dichloromethane/methanol (9:1).
$^1$H NMR (CDCl$_3$, 300 MHz)
3.2 (dd, 4.5 Hz and 9.8 Hz, 1H, H6); 3.5 (dd, 7.7 Hz and 9.8 Hz, 1H, H6); 3.7 (d, 2 Hz, 1H, H4); 3.8 (dd, 2.6 Hz and 9.5 Hz, 1H, H3); 4 (dd, 4.5 Hz and 7.7 Hz; 1H, H5); 4.3-4.9 (m, 9H, H2; 4OCH$_2$Bn); 7.2 (m, 20H, Har).
$^{13}$C NMR (CDCl$_3$, 75 MHz)
69.4 (C6); 71.7 (C5); 73.5 (OCH$_2$Bn); 74.0 (OCH$_2$Bn); 74.1 (C4); 75.0 (OCH$_2$Bn); 75.1 (C2); 75.9 (OCH$_2$Bn); 80.8 (C3); 95.4 (t, 27 Hz, C1); 112.5 (t, 260 Hz, CF$_2$); 127.8-129.0 (Car.); 137.6; 138.0; 138.1 (Car. quat.); 163.1 (t, 30 Hz, CO$_2$H).
$^{19}$F NMR (CDCl$_3$, 282 MHz)
−117.3 (d, J$_{F-F}$=259 Hz); −119.0 (d, J$_{F-F}$=259 Hz)

Synthesis of the Compound 24a (FIG. 12)

On a suspension of the difluoroacid derived from glucose 23a (195 mg; 0.307 mmol; 1 eq.), of the amine of demethyl-epipodophyllotoxin 15 (135 mg; 0.338 mmol; 1.1 eq.), of 1-hydroxybenzotriazole HOBT (45 mg; 0.322 mmol; 1.05 eq.), and of N-methylmorpholine NMM (65 mg; 0.629 mmol; 2.05 eq.) in dichloromethane (10 mL) under an argon atmosphere, 1-(3-dimethylaminopropyl)-3-ethyl-carbodiimide hydrochloride EDCI (62 mg; 0.322 mmol; 1.05 eq.) is added. The reaction is stirred at room temperature for three days. Water (10 mL) is added and the aqueous phase is extracted with dichloromethane (3×15 mL). The organic phases are washed in a saturated solution of sodium chloride NaCl (15 mL), dried on magnesium sulfate $MgSO_4$ and concentrated in vacuo in order to obtain a yellow solid. The residue is purified by chromatography on silica gel with a dichlormethane/ethyl acetate mixture as an eluent in proportions of eight to two.

The pure desired product 24a is obtained as a white solid with a yield of 62% by weight.

Characterization of 24a

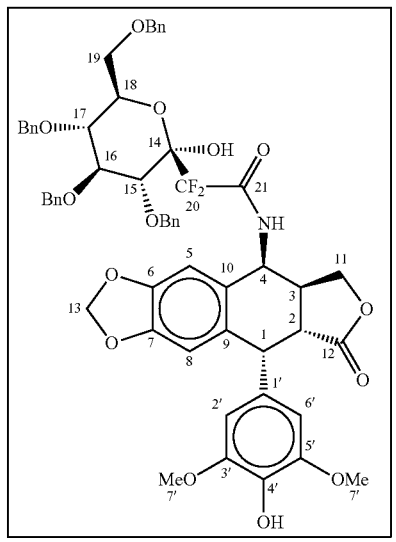

24a

Rf=0.68; eluent: dichloromethane/ethyl acetate (80:20).

$^1$H NMR (CDCl$_3$, 300 MHz)

2.77-2.84 (m, 1H, H2); 2.85-2.94 (m, 1H, H3); 3.43-3.46 (d$_{app}$, 1H, J 10.7, H19); 3.55 (t, 1H, $^3$J 9.4, H16); 3.61-3.62 (m, 1H, H19); 3.66 (s, 6H, H7'×6); 3.81-3.98 (m, 4H, H11, H15, H17, H18); 4.24-4.51 (m, 4H, H11, H1); 4.66-4.84 (m, 6H); 5.16 (dd, 1H, $^3$J$_{H4\text{-}H3}$ 7.5, $^3$J$_{H4\text{-}NH}$ 4.2, H4); 5.49 (s, 1H, Ph-OH); 5.86 (dd, 2H, $^2$J$_{H13\text{-}H13}$ 7.3, $^3$J 1.1, H13×2); 6.19 (s, 2H, H2', H6'); 6.40 (s, 1H, H8); 6.68 (s, 1H, H5); 6.98 (d, 1H, $^3$J$_{NH\text{-}H4}$ 4.2, —NH); 7.00-7.28 (m, 20H).

$^{13}$C NMR (CDCl$_3$, 75 MHz)

35.7 (C3); 40.3 (C2); 42.2 (C1); 47.4 (C4); 55.1 (2C; C7'×2); 66.4 (C19); 67.2 (C11); 70.7 (C15); 71.7; 73.7; 74.1; 74.7; 75.9 (C16); 76.6 (C17); 81.7 (C18); 94.9 (t; $^2$J$_{C\text{-}F}$ 27.5; C14); 100.4 (C13); 106.4 (2C; C2', C6'); 107.7 (C5); 108.8 (C8); 126.0; 126.3; 126.4; 126.5; 126.6; 126.7; 127.1; 127.2; 128.7; 131.3; 131.5; 132.8; 135.9; 136.4; 136.4; 136.9; 145.2 (2C; C3'; C5'); 146.4 (C7); 147.3 (C6); 162.0 (t; $^2$J$_{C\text{-}F}$ 26.8; C21); 172.7 (C12), $^{19}$F NMR (CDCl$_3$, 282 MHz)

−116.3 (d, 1F, $^2$J$_{F\text{-}F}$ 258.6); −120.6 (d, 1F, $^2$J$_{F\text{-}F}$ 258.6).

Synthesis of the Compound 25a (FIG. 12)

On a suspension of the difluoroacid derived from glucose 23a (130 mg; 0.205 mmol; 1 eq.), of the amine of epipodophyllotoxin 16 (93 mg; 0.225 mmol; 1.1 eq.), of HOBT (30 mg; 0.215 mmol; 1.05 eq.), of NMM (43 mg; 0.420 mmol; 2.05 eq.) in dichloromethane (10 mL) under an argon atmosphere, EDCI (42 mg; 0.215 mmol; 1.05 eq.) is added. The reaction is stirred at room temperature for five days. Water (15 mL) is added, and the aqueous phase is extracted with dichloromethane (3×15 mL). The organic phases are washed with a saturated solution of NaCl (20 mL), dried on magnesium sulfate $MgSO_4$ and concentrated in vacuo in order to leave a white solid.

The residue is purified by chromatography on silica gel with a dichloromethane/ethyl acetate mixture as an eluent in proportions of eight to two.

The pure desired product 25a is obtained as a white solid with a yield of 50% by weight.

Characterization of 25a

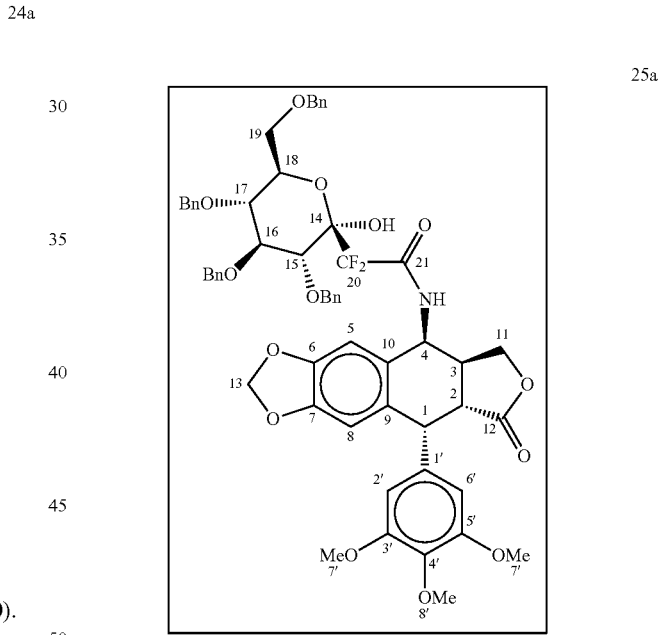

25a

Rf=0.88; eluent: DCM/AcOEt (80:20).

$^1$H NMR (CDCl$_3$, 300 MHz)

2.84-2.90 (m; 1H; H2); 2.94-3.00 (m; 1H; H3); 3.51-3.72 (m; 3H; H19×2; H16); 3.75 (s; 6H; H7'×6); 3.80 (s; 3H; H8'×3); 3.95-4.04 (m; 4H; H11; H15; H18; H17); 4.35-4.53 (m; 4H; H11; H1); 4.77-4.88 (m; 6H); 5.23 (dd, 1H, $^3$J$_{H4\text{-}NH}$ 7.3, $^3$J$_{H4\text{-}H3}$ 4.5, H4); 5.96 (dd, 2H, $^2$J$_{H13\text{-}H13}$ 10.3, $^3$J 1.3, H13×2); 6.26 (s, 2H, H2', H6'); 6.48 (s, 1H, H8); 6.76 (s, 1H, H5); 6.98 (d, 1H, $^3$J$_{NH\text{-}H4}$ 7.2, —NH); 7.01-7.26 (m, 20H).

$^{13}$C NMR (CDCl$_3$, 75 MHz)

37.5 (C3); 42.0 (C2); 44.1 (C1); 48.9 (C4); 56.6 (2C; C7'×2); 61.2 (C8'); 68.2 (C19); 69.0 (C11); 72.5 (C15); 73.4; 75.4; 75.9; 76.4; 77.6 (C16); 78.3 (C17); 83.5 (C18); 96.6 (t; $^2$J$_{C\text{-}F}$ 27.4; C14); 102.1 (C13); 108.5 (2C; C2', C6'); 109.5 (C5); 110.5 (C8); 127.7; 128.1; 128.1; 128.2; 128.2; 128.3; 128.4; 128.7; 128.8; 128.8; 128.9; 132.9; 135.0; 137.6; 137.7;

138.2; 138.6; 148.1 (C7); 149.1 (C6); 153.0 (2C; C3'; C5'); 163.7 (t; $^2J_{C-F}$ 28.0; C21); 172.4 (C12), $^{19}F$ NMR (CDCl$_3$, 282 MHz)

−116.6 (d, 1F, $^2J_{F-F}$ 258.6); −120.3 (d, 1F, $^2J_{F-F}$ 258.6).

Mass spectrometry: ESI+: 1068 (M+K)+, 1052 (M+Na)+, 1030 (M+H)+.

Synthesis of 24b (FIG. 12)

On a suspension of the difluoroacid derived from galactose 23b (185 mg; 0.291 mmol; 1 eq.), of the amine derived from demethylepipodophyllotoxin 15 (130 mg; 0.321 mmol; 1.1 eq.), of HOBT (42 mg; 0.316 mmol; 1.05 eq.), of NMM (61 mg; 0.597 mmol; 2.05 eq.) in DCM (8 mL) under an argon atmosphere, EDCI (60 mg; 0.306 mmol; 1.05 eq.) is added. The reaction is stirred at room temperature for four days. Water (10 mL) is added, and the aqueous phase is extracted with dichloromethane (3×15 mL). The organic phases are washed with a saturated solution of NaCl (25 mL), dried on magnesium sulfate MgSO$_4$ and concentrated in vacuo in order to leave a white solid.

The residue is purified by chromatography on silica gel with a dichloromethane/ethyl acetate mixture as an eluent in proportions of nine to one.

The pure desired product 24b is obtained as a white solid with a yield of 55% by weight.

Characterization of 24b

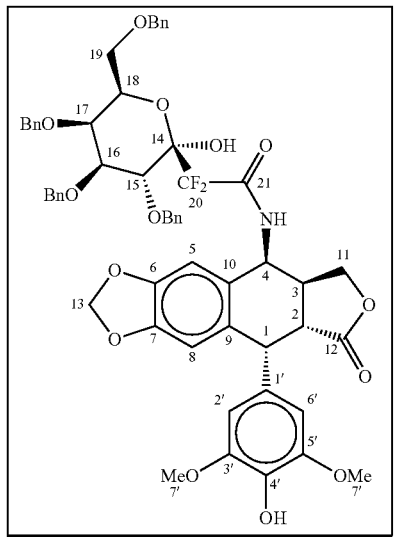

24b

Rf=0.65 eluent: dichloromethane/AcOEt (80:20).

$^1H$ NMR (CDCl$_3$, 300 MHz)

2.78-2.91 (m; 2H; H2; H3); 3.39-3.41 (m; 2H; H19×2); 3.67 (s; 6H; H7'×6); 3.70-3.86 (m; 4H; H11; H16; H17; H18); 4.02-4.08 (m; 1H; H15); 4.26-4.88 (m; 10H; H11; H1); 5.06 (dd, 1H, $^3J_{H4-H3}$ 4.2, $^3J_{H4-NH}$ 7.1, H4); 5.86 (d, 2H, $^2J_{H13-H13}$ 7.2, H13×2); 6.17 (s, 2H, H2', H6'); 6.38 (s, 1H, H8); 6.63 (s, 1H, H5); 6.79 (d, 1H, $^3J_{NH-H4}$ 7.1, —NH); 7.00-7.28 (m, 20H).

$^{13}C$ NMR (CDCl$_3$, 75 MHz) 37.1 (C3); 41.9 (C2); 43.6 (C1); 48.6 (C4); 56.5 (2C; C7'×2); 68.2 (C19); 68.8 (C11); 71.4 (C15); 73.0; 73.3; 73.4 (C16); 74.4 (C17); 74.6; 75.6; 80.7 (C18); 96.5 (t; $^2J_{C-F}$ 26.3; C14); 101.7 (C13); 107.9 (2C; C2'; C6'); 109.4 (C5); 110.2 (C8); 127.6; 127.6; 127.8; 127.9; 128.0; 128.0; 128.3; 128.4; 128.4; 128.5; 128.5; 128.6; 128.7; 130.2; 132.8; 134.2; 137.7; 137.8; 138.1; 138.4; 146.6 (2C; C3'; C5'); 147.6 (C7); 148.6 (C6); 163.4 (t; $^2J_{C-F}$ 28.0; C21); 174.2 (C12), $^{19}F$ NMR (CDCl$_3$, 282 MHz)

−118.3 (d, 1F, $^2J_{F-F}$ 257.5); −119.6 (d, 1F, $^2J_{F-F}$ 257.5).

Synthesis of 25b (FIG. 12)

On a suspension of the difluoroacid derived from galactose 23b (105 mg; 0.165 mmol; 1 eq.), of the amine derived from epipodophyllotoxin 16 (75 mg; 0.181 mmol; 1.1 eq.), of HOBT (24 mg; 0.173 mmol; 1.05 eq.), of NMM (35 mg; 0.338 mmol; 2.05 eq.) in dichloromethane (10 mL) under an argon atmosphere, EDCI (34 mg; 0.173 mmol; 1.05 eq.) is added. The reaction is stirred at room temperature for five days. Water (15 mL) is added, and the aqueous phase is extracted with dichloromethane (3×20 mL). The organic phases are washed with a saturated NaCl solution (25 mL), dried on MgSO$_4$ and concentrated in vacuo in order to leave a white solid. The residue is purified by chromatography on silica gel with a dichloromethane/ethyl acetate mixture as an eluent in proportions of eight to two.

The pure desired product 25b is obtained as a white solid with a yield of 27% by weight.

Characterization of 25b

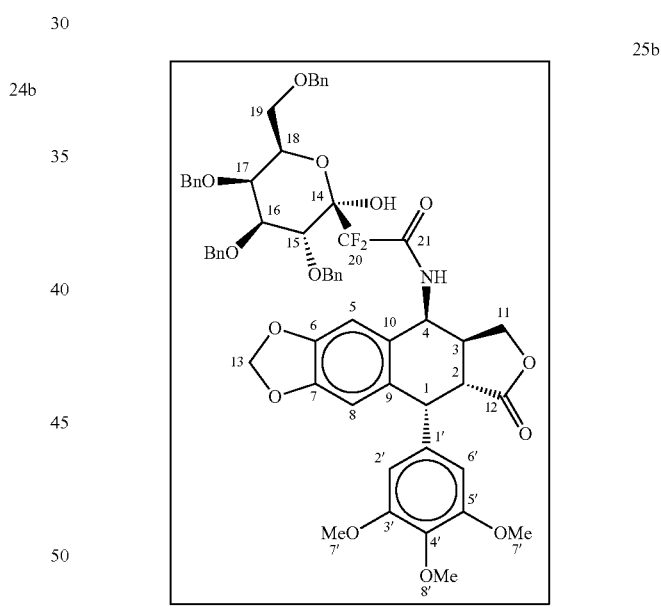

25b

Rf=0.90; eluent: DCM/AcOEt (80:20).

$^1H$ NMR (CDCl$_3$, 300 MHz)

2.79-2.92 (m, 2H, H2, H3); 3.39 (dd, $^3J_{H19-H19}$ 7.7, $^3J_{H19-H18}$ 1.3, 2H, H19×2); 3.67 (s, 6H, H7'×6); 3.71 (s, 3H, H8'×3); 3.68-3.87 (m, 3H, H11, H16, H18); 4.02-4.10 (m, 1H, H15); 4.27-4.89 (m, 11H, H1, H11, H17); 5.06 (dd, 1H, $^3J_{H4-H3}$ 4.0, $^3J_{H4-NH}$ 7.3, H4); 5.87 (dd, 2H, $^2J_{H13-H13}$ 6.9, J 1.1, H13×2); 6.18 (s, 2H, H2', H6'); 6.40 (s, 1H, H8); 6.64 (s, 1H, H5); 6.74 (d, 1H, $^3J_{NH-H4}$ 7.3, —NH); 7.15-7.25 (m, 20H).

$^{13}C$ NMR (CDCl$_3$, 75 MHz)

36.9 (C3); 41.4 (C2); 43.4 (C1); 48.2 (C4); 55.9 (2C; C7'×2); 60.5 (C8'); 67.9 (C19); 68.4 (C11); 71.1 (C15); 72.7; 73.0; 73.0 (C16); 74.0 (C17); 74.2; 75.2; 80.4 (C18); 96.1 (t;

$^2J_{C-F}$ 26.8; C14); 101.3 (C13); 107.9 (2C; C2'; C6'); 109.0 (C5); 109.8 (C8); 127.2; 127.2; 127.4; 127.5; 127.6; 127.7; 128.0; 128.1; 128.1; 128.2; 128.2; 128.3; 132.3; 134.3; 137.0; 137.3; 137.4; 137.7; 138.0; 147.3 (C7); 148.3 (C6); 152.3 (2C; C3'; C5'); 163.0 (t; $^2J_{C-F}$ 28.0; C21); 178.8 (C12), $^{19}$F NMR (CDCl$_3$, 282 MHz)

−118.4 (d, 1F, $^2J_{F-F}$ 258.6); −119.5 (d, 1F, $^2J_{F-F}$ 258.6).

Synthesis of the compound 26a (FIG. 13)

In a flask, the compound 24a (140 mg; 0.138 mmol) is dissolved in methanol (7 mL) with palladium on charcoal and placed under a hydrogen atmosphere. The mixture is stirred overnight at room temperature. The reaction mixture is filtered, concentrated and purified by a silica gel chromatographic column with a dichloromethane/methanol mixture as an eluent in proportions of nine to one.

Le product 26a is isolated as a white solid with a yield of 78% by weight.

Characterization of 26a

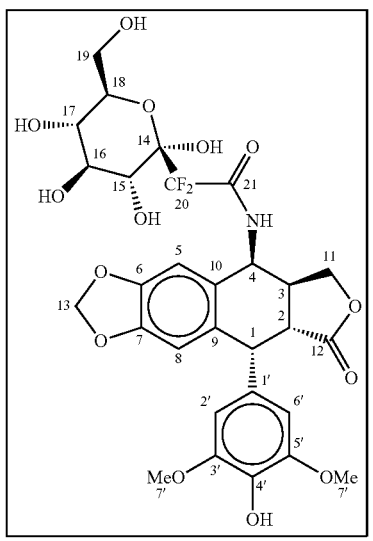

26a

Rf=0.35; eluent: DCM/methanol (80:20).

$^1$H NMR (MeOD, 300 MHz)

2.96-3.11 (m, 1H, H3); 3.18-3.33 (m, 2H, H2); 3.57-3.71 (m, 5H, H18); 3.70 (s, 6H, H7'×6); 3.97 (dd, 1H, $^2J_{H11-H11}$ 9.0, $^3J_{H11-H13}$ 10.9, H11); 4.36 (t$_{app}$, 1H, $^2J_{H11-H11}$ 9.0, H11); 4.58 (d, 1H, $^3J_{H1-H2}$ 5.1, H1); 5.29 (d, 1H, $^3J_{H4-H3}$ 4.5, H4); 5.95 (d, 2H, $^3J_{H13-H13}$ 1.6, H13×2); 6.32 (s, 2H, H2', H6'); 6.50 (s, 1H, H8); 6.77 (s, 1H, H5).

$^{13}$C NMR (MeOD, 75 MHz)

30.7 (C3); 38.6 (C2); 42.8 (C1); 44.9 (C4); 56.5 (2C; C7'×2); 61.7 (C19); 70.2 (C11); 70.6; 71.9; 74.7; 75.7; 97.7 (t; $^2J_{C-F}$ 25.7; C14); 102.9 (C13); 109.3 (2C; C2'; C6'); 110.2 (C5); 110.9 (C8); 129.7; 131.7; 134.2; 135.8; 148.6 (2C; C3'; C5'); 148.8 (C7); 149.7 (C6); 165.6 (t; $^2J_{C-F}$ 29.1; C21); 177.1 (C12).

$^{19}$F NMR (MeOD, 282 MHz)

−119.4 (d, 1F, $^2J_{F-F}$ 256.4); −120.7 (d, 1F, $^2J_{F-F}$ 256.4).

Mass spectrometry: ESI+: 678 (M+Na)+.

Synthesis of the Compound 27a (FIG. 13)

In a flask, the compound 25a (100 mg; 0.097 mmol) is dissolved in methanol (5 mL) with palladium on charcoal and placed under a hydrogen atmosphere. The mixture is stirred overnight at room temperature. The reaction medium is filtered, concentrated in order to thereby obtain the desired product 27a as a white solid with a yield of 90% by weight.

Characterization of 27a

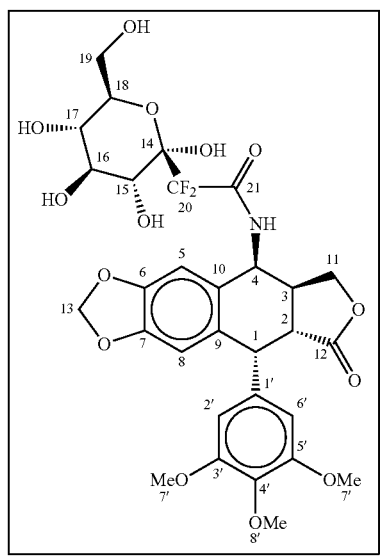

27a

Rf=0.89; eluent: DCM/methanol (80:20).

$^1$H NMR (MeOD, 300 MHz)

2.87-3.07 (m, 1H, H3); 3.13-3.28 (m, 2H, H2); 3.49-3.60 (m, 5H); 3.60 (s, 9H, H7'×6, H8'×3); 3.90 (dd, 1H, $^2J_{H11-H11}$ 9.0, $^3J_{H11-H3}$ 10.7, H11); 4.28 (t$_{app}$, 1H, 2J$_{H11-H11}$ 9.0, H11); 4.52 (d, 1H, $^3J_{H1-H2}$ 5.2, H1); 5.22 (d, 1H, $^3J_{H4-H3}$ 4.6, H4); 5.87 (d, 2H, $^3J_{H13-H13}$ 1.0, H13×2); 6.28 (s, 2H, H2', H6'); 6.42 (s, 1H, H8); 6.70 (s, 1H, H5).

$^{13}$C NMR (MeOD, 75 MHz)

39.7 (C3); 43.7 (C2); 46.1 (C1); 49.9 (C4); 57.6 (2C; C7'×2); 62.1 (C8'); 62.8 (C19); 71.3 (C11); 71.6; 72.9; 75.8; 76.8; 97.1 (t; $^2J_{C-F}$ 26.3; C14); 104.0 (C13); 110.5 (2C; C2'; C6'); 111.3 (C5); 111.9 (C8); 130.8; 134.9; 138.2; 139.2; 150.0 (C7); 150.9 (C6); 154.9 (2C; C3'; C5'); 165.0 (t; $^2J_{C-F}$ 28.6; C21); 178.0 (C12).

$^{19}$F NMR (MeOD, 282 MHz)

Majority anomer: −119.4 (d, 1F, $^2J_{F-F}$ 257.5); −120.6 (d, 1F, $^2J_{F-F}$ 256.4).

Minority anomer: −119.9 (d, 1F, $^2J_{F-F}$ 257.5); −121.1 (d, 1F, $^2J_{F-F}$ 256.4).

Mass spectrometry: ESI+

708 (M+K)+, 692 (M+Na)+, 670 (M+H)+.

Synthesis of 26b (FIG. 13)

In a flask, the compound 24b (95 mg; 0.094 mmol) is dissolved in methanol (8 mL) with palladium on charcoal and placed under a hydrogen atmosphere. The mixture is stirred overnight at room temperature. The reaction medium is filtered, concentrated and purified by a silica gel chromatographic column with a dichloromethane/methanol mixture as an eluent in proportions of eight to two.

Le product 26b is isolated as a white solid with a yield of 89% by weight.

Characterization of 26b

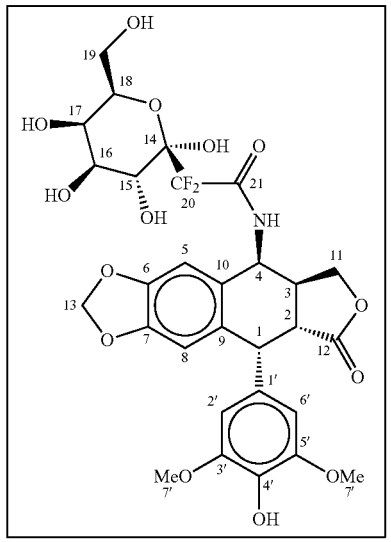

26b

¹H NMR (MeOD, 300 MHz)

Anomer 1: 2.93-3.09 (m; 1H; H3); 3.16-3.27 (m; 2H; H2); 3.51-3.61 (m; 1H; H19); 3.71 (s; 6H; H7'×6); 3.70-3.78 (m; 2H; H19); 3.85-4.16 (m; 3H; H11); 4.32-4.36 (m; 2H; H11); 4.57 (d, 1H, $^3J_{H1-H2}$ 5.1, H1); 5.32 (d, 1H, $^3J_{H4-H3}$ 4.6, H4); 5.94 (s, 2H, H13×2); 6.33 (s, 2H, H2', H6'); 6.49 (s, 1H, H8); 6.77 (s, 1H, H5).

Anomer 2: 5.26 (d, 1H, $^3J_{H4-H3}$ 4.5, H4); 6.85 (s, 1H, H5).

¹³C NMR (MeOD, 75 MHz)

39.0 (C3); 43.2 (C2); 45.3 (C1); 50.1 (C4); 56.9 (2C; C7'×2); 64.4 (C19); 70.6 (C11); 72.4; 76.2; 77.7; 82.2; 103.3 (C13); 109.7 (2C; C2'; C6'); 110.5 (C5); 111.3 (C8); 130.2; 132.2; 134.7; 136.2; 149.0 (2C; C3'; C5'); 149.2 (C7); 150.1 (C6); 177.6 (C12),

¹⁹F NMR (MeOD, 282 MHz)

Anomer 1: −119.1 (d, 1F, $^2J_{F-F}$ 257.6); -120.3 (d, 1F, $^2J_{F-F}$ 257.6).

Anomer 2: −121.4 (d, 1F, $^2J_{F-F}$ 256.4); −123.1 (d, 1F, $^2J_{F-F}$ 256.4).

Mass spectrometry: ESI+: 694 (M+K)+, 678 (M+Na)+, 656 (M+H)+.

Synthesis of the Compound 27b (FIG. 13)

In a flask, the compound 25b (42 mg; 0.041 mmol) is dissolved in methanol (5 mL) with palladium on charcoal and placed under a hydrogen atmosphere. The mixture is stirred overnight at room temperature. The reaction medium is filtered, concentrated in order to thereby obtain the desired product 27b as a white solid with a yield of 86% by weight.

Characterization of 27b

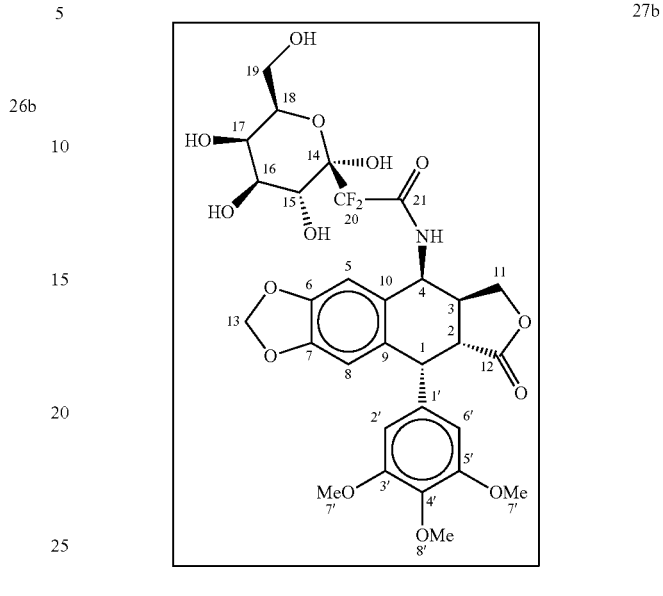

27b

Rf=0.70; eluent: dichloromethane/methanol (80:20).

¹H NMR (MeOD, 300 MHz)

Majority anomer: 2.92-3.09 (m, 1H, H3); 3.17-3.23 (m, 1H, H2); 3.51 (dd, 1H, $^2J_{H19-H19}$ 7.1, $^3J_{H19-H18}$ 2.7, H19); 3.61 (dd, 1H, $^3J_{H19-H19}$ 7.1, $^3J_{H19-H18}$ 3.6, H19); 3.68 (s, 9H, H7'×6, H8'×3); 3.65-3.76 (m, 1H); 3.85-4.13 (m, 3H, H11); 4.31 ($d_{app}$, 2H, $^2J_{H11-H11}$ 7.7, H11); 4.58 (d, 1H, $^3J_{H1-H2}$ 5.1, H1); 5.31 (d, 1H, $^3J_{H4-H3}$ 4.5, H4); 5.92 (s, 2H, H13×2); 6.34 (s, 2H, H2', H6'); 6.46 (s, 1H, H8); 6.75 (s, 1H, H5); 8.82 (d, 1H, $^3J_{NH-H4}$ 8.0, NH), Minority anomer: 5.25 (d, 1H, $^3J_{H4-H3}$ 4.3, H4); 6.84 (s, 1H, H5), ¹³C NMR (MeOD, 75 MHz)

Majority anomer: 39.1 (C3); 43.0 (C2); 45.5 (C1); 50.0 (C4); 56.9 (2C; C7'×2); 62.3 (C8'); 64.4 (C19); 68.9 (C11); 72.4; 76.2; 77.7; 82.2; 103.4 (C13); 109.8 (2C; C2'; C6'); 110.6 (C5); 111.2 (C8); 130.2; 134.3; 137.6; 138.5; 149.3 (C7); 150.2 (C6); 154.2 (2C; C3'; C5'); 176.2 (C12).

Minority anomer: 62.3 (C19); 68.8; 70.5; 72.7; 74.0; 111.6 (C5).

¹⁹F NMR (MeOD, 282 MHz)

Majority anomer: −121.4 (dd, 1F, $^2J_{F-F}$ 256.4, $^2J_{F-F}$ 12.9); −123.0 (dd, 1F, $^2J_{F-F}$ 256.4, $^2J_{F-F}$ 12.6).

Minority anomer: −119.1 (dd, 1F, $^2J_{F-F}$ 257.5, $^2J_{F-F}$ 12.6); −120.2 (dd, 1F, $^2J_{F-F}$ 257.5, $^2J_{F-F}$ 12.6).

Synthesis of the Compound 28a (FIG. 14)

In a flask, the compound 26a (65 mg; 0.10 mmol, 1 eq.) is dissolved in nitromethane MeNO₂ (3 mL) with paratoluene-sulfonic acid APTS (5 mg; 0.025 mmol; 0.25 eq.) and dimethoxyethane (270 mg; 3.0 mmol; 30 eq.) at room temperature under an inert atmosphere. The reaction medium is stirred for three hours. Water (10 mL) is added, and the aqueous phase is extracted with chloroform CHCl₃ (2×20 mL). The organic phases are collected and washed with a saturated solution of sodium chloride NaCl (20 mL), dried on Na₂SO₄ and concentrated in vacuo in order to obtain a yellow oil. The reaction raw product is purified by chromatography column on silica gel with a dichloromethane/methanol mixture as an eluent in proportions of nine to one. The product 28a is isolated as a white solid with a yield of 95% by weight.

Characterization of 28a

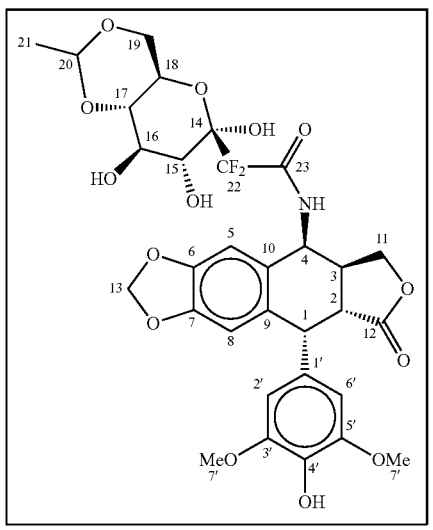

28a

Rf=0.50; eluent: dichloromethane/methanol (90:10).

$^1$H NMR (MeOD, 300 MHz)

1.27 (d, 3H, $^3J_{H21\text{-}H20}$ 5.0, H21×3); 2.98-3.09 (m, 1H, H3); 3.11-3.32 (m, 2H, H2+H18); 3.45-3.48 (m, 1H, H19); 3.71 (s, 6H, H7'×6); 3.72-3.87 (m, 5H, H11, H15, H16, H17, H19); 4.33 ($t_{app}$, 1H, $2J_{H11\text{-}H11}$ 7.7, H11); 4.57 (d, 1H, $^3J_{H1\text{-}H2}$ 4.9, H1); 4.74 (q, 1H, $^3J_{H20\text{-}H21}$ 5.0, H20); 5.31 (d, 1H, $^3J_{H4\text{-}H3}$ 4.5, H4); 5.94 (d, 2H, $^3J_{H13\text{-}H13}$ 1.4, H13×2); 6.33 (s, 2H, H2', H6'); 6.49 (s, 1H, H8); 6.75 (s, 1H, H5).

$^{13}$C NMR (MeOD, 75 MHz)

21.0 (C21); 38.8 (C3); 43.2 (C2); 45.3 (C1); 49.8 (C4); 57.1 (2C; C7'×2); 65.3; 69.4 (C19); 70.4 (C11); 72.9; 73.1; 81.6 (C18); 98.6 (t; $^2J_{C\text{-}F}$ 26.3; C14); 101.7 (C20); 103.4 (C13); 109.8 (2C; C2'; C6'); 110.6 (C5); 111.4 (C8); 130.1; 132.1; 134.7; 136.2; 149.0 (2C; C3'; C5'); 149.1 (C7); 150.1 (C6); 165.5 (t; $^2J_{C\text{-}F}$ 28.0; C23); 177.4 (C12).

$^{19}$F NMR (MeOD, 282 MHz)

−119.7 (d, 1F, $^2J_{F\text{-}F}$ 256.4); −122.3 (d, 1F, $^2J_{F\text{-}F}$ 257.5).

Mass spectrometry: ESI−: 680 (M−H).

Synthesis of the Compound 29a (FIG. 14)

In a flask, the compound 27a (45 mg; 0.07 mmol, 1 eq.) is dissolved in nitromethane (3 mL) with APTS (3 mg; 0.016 mmol; 0.25 eq.) and dimethoxyethane (170 mg; 1.9 mmol; 30 eq.) at room temperature under an inert atmosphere. The reaction medium is stirred for three hours. Water (10 mL) is added, and the aqueous phase is extracted with chloroform CHCl$_3$ (2×20 mL). The organic phases are collected and washed with a saturated solution of NaCl (20 mL), dried on Na$_2$SO$_4$ and concentrated in vacuo in order to obtain a yellow oil. The reaction raw product is purified by a silica gel chromatographic column with a dichloromethane/methanol mixture as an eluent in proportions of nine to one. The product 29a is isolated as a white solid with a yield of 87% by weight.

Characterization of 29a

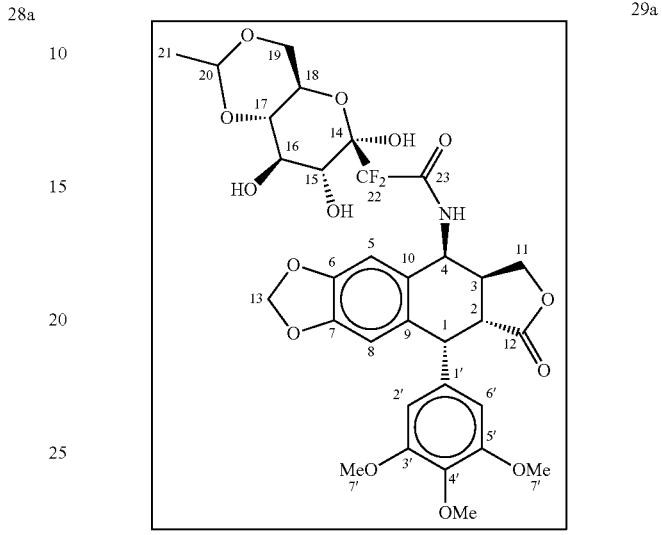

29a

Rf=0.45; eluent: dichloromethane/methanol (90:10).

$^1$H NMR (MeOD, 300 MHz)

1.28 (d, 3H, $^3J_{H21\text{-}H20}$ 5.0, H21×3); 2.97-3.08 (m, 1H, H3); 3.15-3.31 (m, 2H, H2, H18); 3.44 (t, 1H, $^3J_{H19\text{-}H18}$ 10.1, H19); 3.71 (s, 9H, H7'×6, H8'×3); 3.70-3.96 (m, 4H, H11, H15, H16, H17, H19); 4.34 ($t_{app}$, 1H, $^2J_{H11\text{-}H11}$ 8.8, H11); 4.61 (d, 1H, $^3J_{H1\text{-}H2}$ 5.2, H1); 4.73 (q, 1H, $^3J_{H20\text{-}H21}$ 5.0, H20); 5.30 (d, 1H, $^3J_{H4\text{-}H3}$ 4.6, H4); 5.94 (dd, 2H, $^3J_{H13\text{-}H13}$ 3.2, J 1.0, H13×2); 6.35 (s, 2H, H2', H6'); 6.50 (s, 1H, H8); 6.75 (s, 1H, H5).

$^{13}$C NMR (MeOD, 75 MHz)

21.0 (C21); 38.9 (C3); 43.0 (C2); 45.5 (C1); 49.7 (C4); 59.9 (2C; C7'×2); 61.4 (C8'); 65.2 (C19); 69.4; 70.4; 72.9; 73.1; 81.6; 98.6 (t; $^2J_{C\text{-}F}$ 30.0; C14); 101.1 (C20); 103.4 (C13); 109.8 (2C; C2'; C6'); 110.6 (C5); 111.3 (C8); 130.2; 134.5; 137.5; 138.6; 149.3 (C7); 150.2 (C6); 154.2 (2C; C3'; C5'); 165.5 (t; $^2J_{C\text{-}F}$ 33.7; C23); 177.2 (C12).

$^{19}$F NMR (MeOD, 282 MHz)

−119.8 (d, 1F, $^2J_{F\text{-}F}$ 257.5); −121.9 (d, 1F, $^2J_{F\text{-}F}$ 257.5).

Mass spectrometry: ESI+: 734 (M+K)+, 718 (M+Na)+, 696 (M+H)

Synthesis of the Compound 28b (FIG. 14)

In a flask, the compound 26b (45 mg; 0.068 mmol; 1 eq.) is dissolved in nitromethane (3 mL) with APTS (4 mg; 0.017 mmol; 0.25 eq.) and dimethoxyethane (190 mg; 2.1 mmol; 30 eq.) at room temperature under an inert atmosphere. The reaction medium is stirred for three hours. Water (10 mL) is added, and the aqueous phase is extracted with CHCl$_3$ (2×20 mL). The organic phases are collected and washed with a saturated solution of NaCl (20 mL), dried on Na$_2$SO$_4$ and concentrated in vacuo in order to leave a yellow oil. The reaction raw product is purified by a silica gel chromatographic column with a dichloromethane/methanol mixture as an eluent in proportions of nine to one. The product 28b is isolated as a white solid with a yield of 59% by weight.

Characterization of 28b

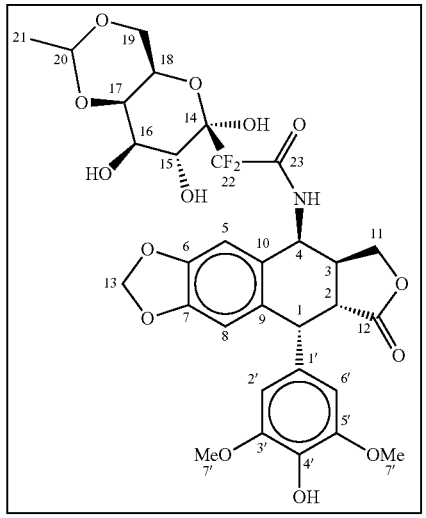

Rf=0.40; eluent: DCM/methanol (90:10).
$^1$H NMR (MeOD, 300 MHz)
Anomer 1: 1.29 (d, 3H, $^3J_{H21-H20}$ 4.9, H21×3); 2.94-3.09 (m, 1H, H3); 3.18-3.29 (m, 1H, H2); 3.71 (s, 6H, H7'×6); 3.61-4.19 (m, 7H, H11, H15, H16, H17, H18, H19×2); 4.33 ($t_{app}$, 1H, $^2J_{H11-H11}$ 8.3, H11); 4.57 (t, 1H, $^3J_{H1-H2}$ 5.6, H1); 4.76 (q, 1H, $^3J_{H20-H21}$ 4.9, H20); 5.33 (d, 1H, $^3J_{H4-H3}$ 4.5, H4); 5.94 (s, 2H, H13×2); 6.33 (s, 2H, H2', H6'); 6.50 (s, 1H, H8); 6.80 (s, 1H, H5).
Anomer 2: 1.27 (d, 3H, $^3J_{H21-H20}$ 4.8, H21×3); 1.33 (d, 3H, $^3J_{H21-H20}$ 4.8, H21×3); 4.95 (q, 1H, $^3J_{H20-H21}$ 4.8, H20); 5.07 (q, 1H, $^3J_{H20-H21}$ 4.8, H20); 5.25 (d, 1H, $^3J_{H4-H3}$ 4.5, H4); 6.34 (s, 2H, H2', H6'); 6.98 (s, 1H, H5).
$^{13}$C NMR (MeOD, 75 MHz)
Anomer 1: 20.4 (C21); 39.1 (C3); 43.2 (C2); 45.3 (C1); 49.4 (C4); 57.1 (2C; C7'×2); 65.9; 67.0 (C11); 70.5 (C19); 71.0; 77.4; 100.4 (C20); 103.3 (C13); 109.7 (2C; C2'; C6'); 110.5 (C5); 111.3 (C8); 130.2; 132.2; 134.7; 149.0 (2C; C3'; C5'); 149.3 (C7); 150.1 (C6); 177.1 (C12).
Anomer 2: 20.6 (C21); 21.5 (C21); 67.4 (C11); 70.7 (C19); 76.9; 77.1; 79.9; 82.4; 110.8 (C5).
$^{19}$F NMR (MeOD, 282 MHz)
Anomer 1: −118.5 (d, 1F, $^2J_{F-F}$ 254.9); −121.8 (d, 1F, $^2J_{F-F}$ 256.4).
Anomer 2: −121.6 (d, 1F, $^2J_{F-F}$ 255.4); −123.5 (d, 1F, $^2J_{F-F}$ 255.4).

Synthesis of the Compound 29b (FIG. 14)

In a flask, the compound 27b (25 mg; 0.037 mmol; 1 eq.) is dissolved in nitromethane (3 mL) with APTS (2 mg; 0.01 mmol; 0.25 eq.) and dimethoxyethane (108 mg; 1.2 mmol; 30 eq.) at room temperature under an inert atmosphere. The reaction medium is stirred for three hours. Water (10 mL) is added, and the aqueous phase is extracted with CHCl$_3$ (2×20 mL). The organic phases are collected and washed with a saturated solution of NaCl (20 mL), dried on Na$_2$SO$_4$ and concentrated in vacuo in order to leave a yellow oil. The reaction raw product is purified by a silica gel chromatographic column with a dichloromethane/methanol mixture as an eluent in proportions of nine to one. The product 29b is isolated as a white solid with a yield of 58% by weight.

Characterization of 29b

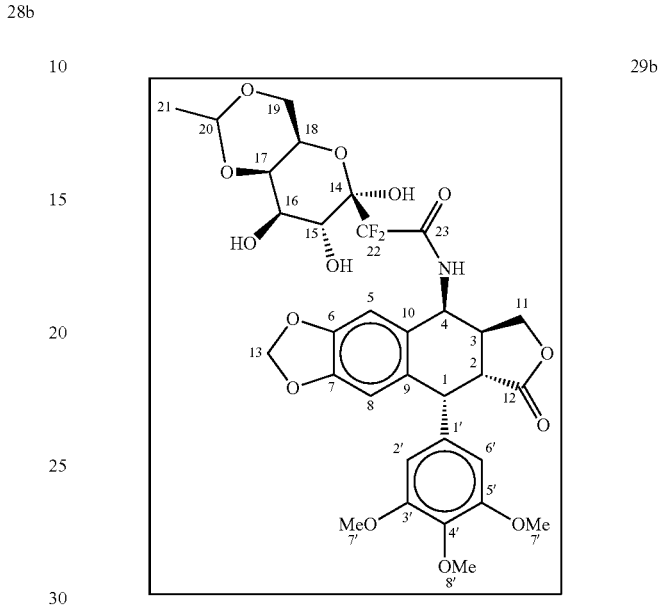

Rf=0.58; eluent: dichloromethane/methanol (90:10).
$^1$H NMR (MeOD, 300 MHz)
Anomer 1: 1.29 (d, 3H, $^3J_{H21-H20}$ 5.0, H21×3); 3.00-3.06 (m, 1H, H3); 3.21-3.30 (m, 1H, H2); 3.71 (s, 9H, H7'×6, H8'×3); 3.59-4.20 (m, 7H, H11, H15, H16, H17, H18, H19×2); 4.29-4.38 (m, 1H, H11); 4.61 ($t_{app}$, 1H, $^3J_{H1-H2}$ 6.7, H1); 4.76 (q, 1H, $^3J_{H20-H21}$ 5.0, H20); 5.26 (d, 1H, $^3J_{H4-H3}$ 4.5, H4); 5.95 (s, 2H, H13×2); 6.36 (d, 2H, J 2.9, H2', H6'); 6.49 (s, 1H, H8); 6.89 (s, 1H, H5).
Anomer 2: 1.26 (d, 3H, $^3J_{H21-H20}$ 4.7, H21×3); 4.96 (q, 1H, $^3J_{H20-H21}$ 4.7, H20); 5.34 (d, 1H, $^3J_{H4-H3}$ 4.4, H4); 6.78 (d, 1H, J 2.6, H5).
$^{13}$C NMR (MeOD, 75 MHz)
Anomer 1: 21.5 (C21); 39.2 (C3); 43.0 (C2); 45.5 (C1); 49.1 (C4); 56.9 (2C; C7'×2); 61.4 (C8'); 65.9; 67.0; 68.5; 69.9; 71.0; 77.2; 100.4 (C20); 103.3 (C13); 109.9 (2C; C2'; C6'); 110.6 (C5); 111.2 (C8); 130.1; 134.3; 137.6; 138.6; 149.4 (C7); 150.2 (C6); 154.2 (2C; C3'; C5'); 177.2 (C12),
Anomer 2: 20.4 (C21); 20.6 (C21); 70.7; 76.6; 76.9; 77.4; 103.9 (C13); 109.8 (2C; C6'; C2'); 110.8 (C5),
$^{19}$F NMR (MeOD, 282 MHz)
Anomer 1: −119.6 (d, 1F, $^2J_{F-F}$ 256.4); −121.7 (d, 1F, $^2J_{F-F}$ 257.5).
Anomer 2: −121.7 (d, 1F, $^2J_{F-F}$ 257.4); -124.0 (d, 1F, $^2J_{F-F}$ 256.4).
Mass spectrometry: ESI–: 694 (M–H).

Synthesis of the Compound 30a (FIG. 15)

The product 25a (30 mg; 0.051 mmol; 1 eq.) is dissolved in 5 mL of THF. The complex BH$_3$.THF 1M (0.10 mL; 0.102 mmol; 2 eq.) is added onto the mixture at room temperature, and the reaction is refluxed for three hours. The reaction medium is left to return to room temperature. A 1N HCl solution (10 mL) is added, and the aqueous phase is extracted with DCM (3×10 mL). The organic phases are washed with a saturated solution of NaCl (15 mL), dried on MgSO₄ and concentrated in vacuo in order to leave a white solid. The residue is purified by chromatography on silica gel with a DCM/AcOEt (90:10) mixture as an eluent in order to obtain the pure desired product 30a as a white solid with a yield of 46% by weight.

Characterization of 30a

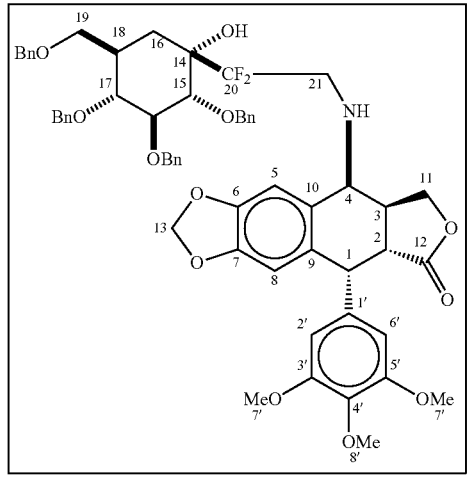

30a

Rf=0.66; eluent: DCM/AcOEt (90:10).

$^1$H NMR (CDCl₃, 300 MHz)

2.62-2.78 (m, 1H, H3); 3.07 (dd, 1H, $^3$J 5.2, 14.1, H2); 3.52-3.58 (m, 3H, H16, H19×2); 3.66 (s, 6H, H7'×6); 3.72 (s, 3H, H8'×3); 3.85-3.99 (m, 4H, H4, H15, H17, H18); 4.16-4.21 (m, 2H, H11×2); 4.38-4.53 (m, 4H, H1); 4.71-4.82 (m, 7H); 5.86 (d, 2H, $^2$J$_{H13-H13}$ 14.7, H13×2); 6.17 (s, 2H, H2', H6'); 6.38 (s, 1H, H8); 6.79 (s, 1H, H5); 7.12-7.31 (m, 20H).

$^{13}$C NMR (CDCl₃, 75 MHz)

39.0 (C3); 41.4 (C2); 44.1 (C1); 56.6 (2C; C7'×2); 57.0 (C4); 61.1 (C8'); 68.7 (C11); 68.9 (C19); 72.1 (C15); 73.5; 75.4; 75.7; 76.4; 78.0 (C16); 78.8 (C17); 83.8 (C18); 96.7 (t; $^2$J$_{C-F}$ 9.1; C14); 101.6 (C13); 108.5 (2C; C2'; C6'); 108.9 (C5); 110.3 (C8); 127.7; 127.8; 127.9; 128.0; 128.1; 128.2; 128.5; 128.5; 128.6; 128.7; 131.7; 135.6; 137.3; 137.7; 138.0; 138.3; 138.5; 147.5 (C7); 148.1 (C6); 152.6 (2C; C3'; C5'); 175.2 (C12).

$^{19}$F NMR (CDCl₃, 282 MHz)

−115.5 (dt$_{app}$, 1F, $^2$J$_{F-F}$ 252.2, $^3$J$_{F-H}$ 11.8); −117.2 (dt$_{app}$, 1F, $^2$J$_{F-F}$ 252.2, $^3$J$_{F-H}$ 16.1).

Synthesis of the Compound 31a (FIG. 16)

Onto a suspension of the difluoroacid derived from glucose 23a (48 mg; 0.075 mmol; 1.00 eq.), of the amine of epipodophyllotoxin 17 (31 mg; 0.082 mmol; 1.10 eq.), of HOBT (11 mg; 0.079 mmol; 1.05 eq.), of NMM (16 mg; 0.154 mmol; 2.05 eq.) in dichloromethane (7 mL) under an argon atmosphere, EDCI (16 mg; 0.079 mmol; 1.05 eq.) is added. The reaction is stirred at room temperature for 7 days. Water (10 mL) is added, and the aqueous phase is extracted with dichloromethane (3×10 mL). The organic phases are washed with a saturated solution of NaCl (10 mL), dried on magnesium sulfate MgSO₄ and concentrated in vacuo in order to leave a white solid.

The residue is purified by chromatography on silica gel with a dichloromethane/ethyl acetate mixture as an eluent in proportions of 9 to 1.

The pure desired product 31a is obtained as a colorless oil with a yield of 29% by weight.

Characterization of 31a

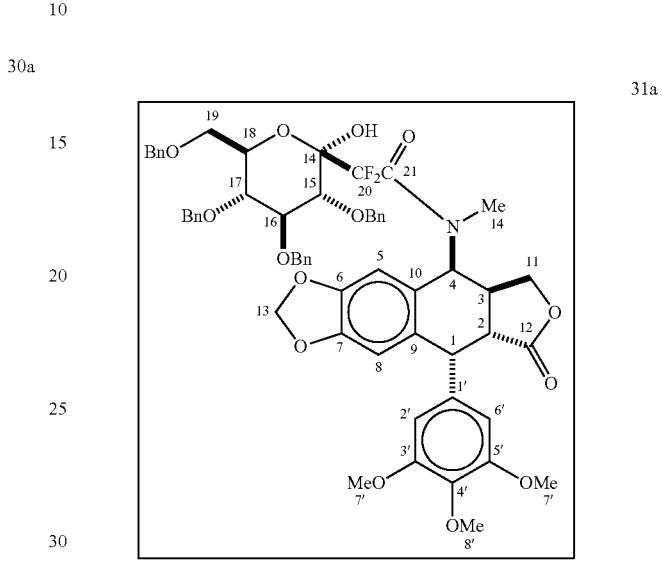

31a

Rf=0.48, eluent: DCM/AcOEt (80:20).

$^1$H NMR (CDCl₃, 300 MHz)

2.52 (s, 1H, H2), 2.65 (s, 3H, H14×3), 2.83 (dd, 1H, $^3$J$_{H3-H11}$ 9.3, 5.0, H3), 3.53-3.80 (m, 3H, H19×2, H16), 3.75 (s, 6H, H7'×6), 3.80 (s, 3H, H8'×3), 3.88 (s, 1H, H4), 3.93-4.21 (m, 5H, H11×2, H15, H17, H18), 4.30 (s, 1H, H1), 4.32-4.88 (m, 8H), 5.93 (dd, 2H, $^2$J$_{H13-H13}$ 6.3, J 1.2, H13×2), 6.29 (s, 2H, H2', H6'), 6.48 (s, 1H, H8), 6.61 (s, 1H, H5), 7.12-7.33 (m, 20H).

$^{13}$C NMR (CDCl₃, 75 MHz)

27.6 (C14), 40.3 (C3), 46.5 (C1), 51.3 (C2), 56.7 (2C, C7'×2), 61.2 (C8'), 62.4 (C4), 66.4 (C11), 68.5 (C19), 73.0 (C15), 73.7, 75.4, 75.6, 76.3, 77.7 (C16), 78.4 (C17), 83.1 (C18), 101.0 (C13), 105.8 (2C, C2', C6'), 107.1 (C5), 112.0 (C8), 127.3, 127.4, 127.6, 127.9, 128.1, 128.2, 128.2, 130.9, 136.8, 137.1, 137.6, 137.8, 137.9, 139.3, 145.6 (C7), 147.6 (C6), 153.1 (2C, C3', C5'), 174.3 (C12).

$^{19}$F NMR (CDCl₃, 282 MHz)

−117.9 (d, 1F, $^2$J$_{F-F}$ 256.4), −119.7 (d, 1F, $^2$J$_{F-F}$ 256.4).

Synthesis of the Compound 32a (FIG. 17)

In a flask, the compound 30a (11 mg; 0.011 mmol) is dissolved in methanol (5 mL) with palladium on charcoal and placed under a hydrogen atmosphere. The mixture is stirred overnight at room temperature. The reaction medium is filtered, concentrated and then purified on a silica gel column with a DCM/MeOH mixture with a ratio 80:20 so as to thereby leave the desired product 32a as a colorless oil.

Characterization of the Compound 32a

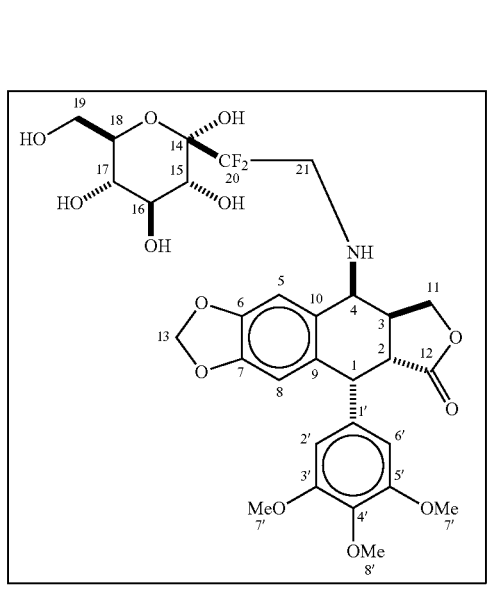

32a

Characterization of the Compound 33a

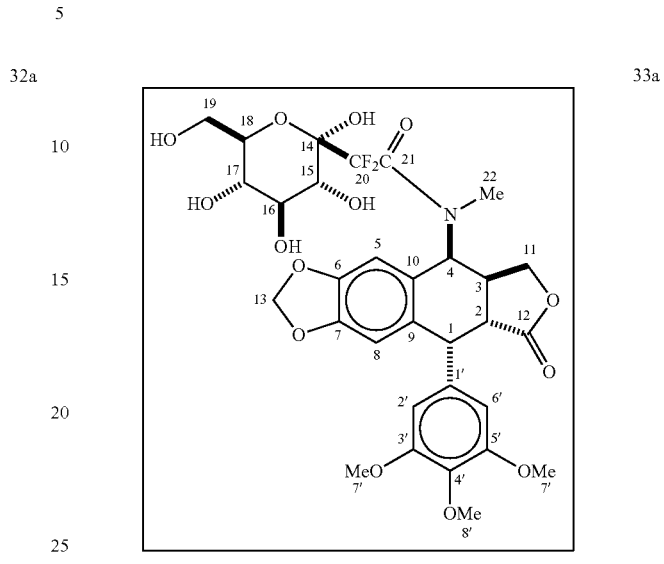

33a

Rf=0.90, eluent: DCM/MeOH (80:20).

$^1$H NMR (CDCl$_3$, 300 MHz)

2.72-2.99 (m, 1H, H3), 3.22-3.39 (m, 3H, H2, H19×2), 3.66 (s, 9H, H7'×6, H8'×3), 3.61-3.86 (m, 4H, H15, H16, H17, H18), 4.11 (d, 1H, $^3J_{H4-H3}$ 4.1, H4), 4.33-4.41 (m, 3H, H21, H11×2), 4.53 (d, 1H, $^3J_{H1-H2}$ 5.4, H1), 4.70-4.81 (m, 1H, H21), 5.92 (d, 2H, $^2J_{H13-H13}$ 1.3, H13×2), 6.29 (s, 2H, H2', H6'), 6.42 (s, 1H, H8), 7.02 (s, 1H, H5).

$^{13}$C NMR (CDCl$_3$, 75 MHz)

40.8 (C3), 42.6 (C2), 45.5 (C1), 56.9 (2C, C7'×2), 58.2 (C4), 61.4 (C8'), 63.0 (C19), 70.7 (C11), 71.7, 72.6, 75.0, 76.3, 90.0 (C14), 103.1 (C13), 109.8 (2C, C2', C6'), 110.7 (C5), 111.1 (C8), 133.1, 134.0, 136.9, 138.2, 149.1 (C7), 149.6 (C6), 154.1 (2C, C3', C5'), 178.2 (C12).

$^{19}$F NMR (CDCl$_3$, 282 MHz)

−117.4 (dt, 1F, $^2J_{F-F}$ 255.4, $^3J_{F-H21}$ 17.1), −118.6 (ddd, 1F, $^2J_{F-F}$ 255.4, $^3J_{F-H21}$ 15.0, 10.7).

Mass spectrometry: ESI−: 654 (M)−.

Synthesis of the Compound 33a (FIG. 18)

In a flask, the compound 31a (22 mg; 0.21 mmol) is dissolved in methanol (5 mL) with palladium on charcoal and placed under a hydrogen atmosphere. The mixture is stirred overnight at room temperature. The reaction medium is filtered, concentrated and then purified by chromatography on a silica column with a DCM/MeOH mixture (80:20) as an eluent. The product 33a is isolated as a white solid with a yield of 58% by weight.

Rf=0.83, eluent: DCM/methanol (80:20).

$^1$H NMR (MeOD, 300 MHz)

2.63 (ls, 1H, H2), 2.71 (s, 3H, H22×3), 2.95 (dd, 1H, $^3J_{H3-H4}$ 9.2, $^3J_{H3-H11}$ 5.8, H3), 3.20-3.32 (m, 1H), 3.52-3.73 (m, 5H), 3.74 (s, 9H, H7'×6, H8'×3), 4.14 (dd, 1H, $^3J_{H11-H3}$ 5.8, $^2J_{H11-H11}$ 11.2, H11), 4.26-4.38 (m, 3H, H1, H4, H11), 5.93 (dd, 2H, J 0.8, $^2J_{H13-H13}$ 9.7, H13×2), 6.40 (s, 2H, H2', H6'), 6.46 (s, 1H, H8), 6.86 (s, 1H, H5).

$^{13}$C NMR (MeOD, 75 MHz)

28.3 (C22), 41.6 (C3), 47.5 (C1), 52.7 (C2), 56.9 (2C, C7'×2), 61.3 (C8'), 62.5 (C11), 63.7 (C4), 66.9 (C6), 71.1, 72.2, 75.2, 76.2, 103.0 (C13), 107.5 (2C, C2', C6'), 109.0 (C5), 113.0 (C8), 130.0, 133.2, 138.3, 141.7, 147.7 (C7), 149.7 (C6), 154.8 (2C, C3', C5').

$^{19}$F NMR (MeOD, 282 MHz)

−120.4 (d, 1F, $^2J_{F-F}$ 254.9); −123.5 (d, 1F, $^2J_{F-F}$ 254.9).

Synthesis of the Compound 34a (FIG. 19)

In a flask under an inert atmosphere containing the difluoroester 22a (215 mg; 0.324 mmol; 1 eq.) in solution in anhydrous dichloromethane (5 mL) at −30° C., thionyl chloride SOCl$_2$ is added dropwise (37 μL; 0.49 mmol; 1.5 eq.). After 30 minutes of stirring at −30° C., pyridine (40 μL; 0.49 mmol; 1.5 eq.). is introduced and stirring is continued for a further 30 minutes. A 2M HCl solution is added and the phase is extracted three times with dichloromethane. The organic phases are collected, washed with a saturated solution of NaCl, dried on MgSO$_4$, filtered and concentrated under reduced pressure. The reaction raw product is purified on a silica column with a cyclohexane/ethyl acetate 9:1 eluting mixture in order to isolate the chlorinated product 34a (mixture of 2 anomers) as a colorless oil with a yield of 51%.

Characterization of the Compound 34a

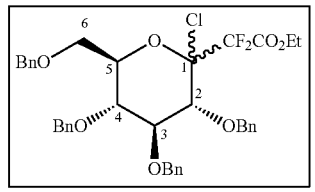

34a $C_{38}H_{39}ClF_2O_7$ M=681.16 g.mol$^{-1}$ $^{19}$F NMR (CDCl$_3$, 282 MHz)
−109.3 (d, 1F, $^2J_{F-F}$ 261 Hz), −111.2 (d, 1F, $^2J_{F-F}$ 261)→82% in majority −111.5 (d, 1F, $^2J_{F-F}$ 250 Hz), −113.6 (d, 1F, $^2J_{F-F}$ 250 Hz)→18% in minority $^1$H NMR (CDCl$_3$, 300 MHz)
1.07 (t, 7.2 Hz, 3H, CH$_3$); 3.74 (dd, 1.9 et 11.6 Hz, 1H, H6); 3.80 (dd, 3.3 and 11.6 Hz, 1H, H6); 3.91-3.97 (m, 3H, CH$_3$ and H3); 4.16 (m, 2H, H5 and H2); 4.31 (dd, 7.3 and 10.9 Hz, 1H, H4); 4.48-4.84 (m, 8H, 4OCH$_2$Ph); 7.19-7.40 (m, 20H, Har).

$^{13}$C NMR (CDCl$_3$, 75.5 MHz)
Majority
13.8 (CH$_3$); 63.1 (CH$_2$); 68.1 (C6); 73.1 (OCH$_2$Ph); 73.4 (OCH$_2$Ph); 73.7 (OCH$_2$Ph); 74.7 (OCH$_2$Ph); 76.0 (C4); 76.7 (C5 or C2); 82.0 (C5 or C2); 82.9 (C3); 99.8 (dd, 26 and 31 Hz, C1); 112.1 (dd, 259 and 263 Hz, CF$_2$); 127.6; 127.8; 128.0; 128.1; 128.2; 128.3; 128.4; 128.5 (2C); 128.6; 128.7 (Car.); 136.7; 137.8; 138.1; 138.4 (Car. quat.); 161.5 (t, 33 Hz, CO$_2$Et).

Minority
14.0 (CH$_3$); 63.6 (CH$_2$); 67.6 (C6); 73.5 (OCH$_2$Ph); 75.0 (OCH$_2$Ph); 75.4 (OCH$_2$Ph); 75.7 (C4); 76.2 (OCH$_2$Ph); 76.3 (C5 or C2); 79.2 (C5 or C2); 83.4 (C3).

Synthesis of the Compound 35a (FIG. 20)

In a flask under an inert atmosphere containing the chlorinated ester 34a (115 mg; 0.169 mmol; 1 eq.) in solution in ethanol (4 mL), an aqueous solution of lithine (2M; 2 eq.) is added and the mixture is stirred overnight at room temperature. The mixture is concentrated and dissolved in DCM (5 mL), it is then acidified with a 1M HCl solution (20 mL). The mixture is extracted with DCM (3×20 mL), and the organic phases are combined, washed with a saturated solution of NaCl and directly concentrated. The acid 35a is thereby isolated as a white oil which may be directly used for the next step without any further purifications with a gross yield of 84%.

Characterization of the Compound 35a

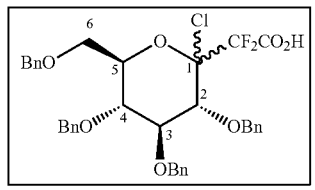

35a $^1$H NMR (CDCl$_3$, 300 MHz)
3.40-3.47 (m, 1H), 3.48 (dd, 1H, J 10.6, 6.6), 3.63 (d$_{app}$, 1H, J 9.2, H6), 3.93-3.95 (m, 2H, H2+H4), 4.03-4.10 (m, 1H, H5), 4.41-4.60 (m, 3H), 4.73-4.84 (m, 5H), 7.04-7.29 (m, 20H, H$_{Ar}$).

$^{13}$C NMR (CDCl$_3$, 75 MHz)
68.4 (C6), 71.9 (C5), 73.1, 75.2, 75.6, 76.2, 77.5, 78.2 (C4), 83.3 (C3), 96.1 (t, $^2J_{C-F}$ 26.8, C1), 127.9, 127.9, 128.1, 128.2, 128.3, 128.6, 128.6, 128.7, 136.7, 137.4, 137.6, 138.3, 163.2 (t, $^3J_{C-F}$ 32.0, C8).

$^{19}$F NMR (CDCl$_3$, 282 MHz)
−117.2 (d, $^2J_{F-F}$ 258.6), −118.9 (d, $^2J_{F-F}$ 258.6).

Synthesis of the Compound 36a (FIG. 21)

On a suspension of the acid 35a (90 mg; 0.138 mmol; 1 eq.), of the amine 16 (63 mg; 0.152 mmol; 1.1 eq.), of HOBT (20 mg; 0.145 mmol; 1.05 eq.), and of NMM (29 mg; 0.283 mmol; 2.05 eq.) in DCM (8 mL) under an argon atmosphere, EDCI (28 mg; 0.145 mmol; 1.05 eq.) is added. The reaction is stirred at room temperature for 3 days. Water (10 mL) is added, and the aqueous phase is extracted with DCM (3×15 mL). The organic phases are washed with a saturated solution of NaCl (15 mL), dried on MgSO$_4$ and concentrated in vacuo so as to leave a yellow oil. The residue is purified by chromatography on silica gel with a DCM/AcOEt (80:20) mixture as an eluent in order to obtain the pure desired product 36a as a yellow oil with a yield of 32%.

Characterization of the Compound 36a

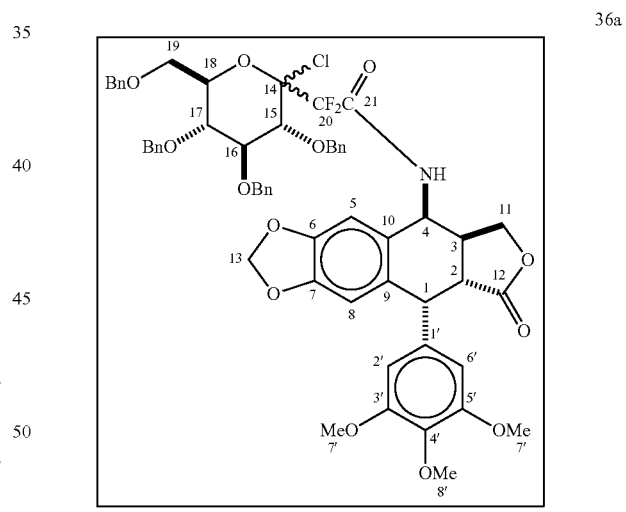

36a

Rf=0.87, eluent: DCM/AcOEt (80:20).

$^1$H NMR (CDCl$_3$, 300 MHz)
2.81-2.88 (m, 1H, H2), 2.89-2.98 (m, 1H, H3), 3.47-3.63 (m, 3H, H19×2), 3.71 (s, 6H, H7'×6), 3.76 (s, 3H, H8'×3), 3.91-3.97 (m, 4H, H11), 4.35-4.45 (m, 5H, H11, H1), 4.72-4.84 (m, 5H), 5.19 (dd, 1H, $^3J_{H4-H3}$ 4.7, $^3J_{H4-NH}$ 7.3, H4), 5.91 (dd, 2H, $^3J_{H13-H13}$ 9.1, J 0.9, H13×2), 6.22 (s, 2H, H2', H6'), 6.43 (s, 1H, H8), 6.72 (s, 1H, H5), 6.96 (d, 1H, $^3J_{NH-H4}$ 7.3, —NH), 7.08-7.32 (m, 20H).

$^{13}$C NMR (CDCl$_3$, 75 MHz)
37.4 (C3), 41.9 (C2), 43.9 (C1), 48.8 (C4), 56.5 (2C, C7'×2), 61.0 (C8'), 68.1 (C19), 68.8 (C11), 72.4, 73.2, 75.3, 75.8, 76.3, 77.5, 78.1, 83.4, 96.5 (t, $^2J_{C-F}$ 27.4, C14), 101.9 (C13), 108.4 (2C, C2', C6'), 109.3 (C5), 110.4 (C8), 127.6, 127.9, 128.0, 128.1, 128.1, 128.3, 128.6, 128.7, 128.7, 132.8, 134.8, 137.5, 137.6, 138.0, 138.1, 138.4, 148.0 (C7), 148.9 (C6), 152.9 (2C, C3', C5'), 163.8 (t, $^2J_{C-F}$ 30.0, C21), 174.2 (C12).
$^{19}$F NMR (CDCl$_3$, 282 MHz)
−116.6 (d, 1F, $^2J_{F-F}$ 258.6), −120.4 (d, 1F, $^2J_{F-F}$ 2586).

Synthesis of the Compound 37a (FIG. 22)

In a flask, the compound 36a (44 mg; 0.042 mmol) is dissolved in methanol (10 mL) with palladium on charcoal and placed under a hydrogen atmosphere. The mixture is stirred overnight at room temperature. The reaction mixture is filtered, concentrated in order to thereby leave the desired product 37a as a pale yellow solid with a yield of 68%.

Characterization of the Compound 37a

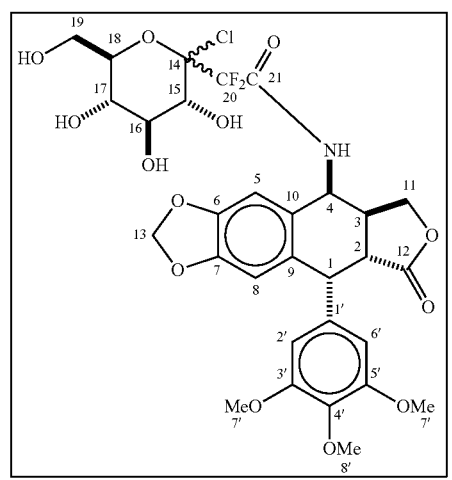

37a

Rf=0.33, eluent: DCM/methanol (90:10).
$^1$H NMR (MeOD, 300 MHz)
2.99-3.10 (m, 1H, H3), 3.22-3.34 (m, 2H, H2), 3.22-3.72 (m, 5H), 3.71 (s, 9H, H7'×6, H8'×3), 3.99 (dd, 1H, $^2J_{H11-H11}$ 8.9, $^3J_{H11-H3}$ 10.9, H11), 4.37 (dd, 1H, $^2J_{H11-H11}$ 8.9, $^3J_{H11-H3}$ 7.6, H11), 4.62 (d, 1H, $^3J_{H1-H2}$ 5.1, H1), 5.31 (d, 1H, $^3J_{H4-H3}$ 4.6, H4), 5.96 (d, 2H, $^3J_{H13-H13}$ 0.6, H13×2), 6.37 (s, 2H, H2', H6'), 6.50 (s, 1H, H8), 6.79 (s, 1H, H5).
$^{13}$C NMR (MeOD, 75 MHz)
38.8 (C3), 42.8 (C2), 45.3 (C1), 49.9 (C4), 56.7 (2C, C7'×2), 61.2 (C8'), 61.9 (C19), 70.4 (C11), 70.8, 72.1, 74.9, 75.9, 97.6 (C14), 103.2 (C13), 109.6 (2C, C2', C6'), 110.4 (C5), 111.1 (C8), 130.0, 134.1, 137.3, 138.4, 149.1 (C7), 150.0 (C6), 154.0 (2C, C3', C5'), 174.8 (C21), 177.1 (C12).
$^{19}$F NMR (MeOD, 282 MHz)
−119.4 (d, 1F, $^2J_{F-F}$ 257.5), −120.7 (d, 1F, $^2J_{F-F}$ 257.5).
Mass spectrometry: ESI+: 686 (M−H)−.

Synthesis of the Compound 38a (FIG. 23)

The halogenated product 35a is placed with tributyl tin (1.5 eq.) in dry toluene and the solution is refluxed for one hour. After returning to room temperature, the mixture is concentrated and purified by a silica gel chromatographic column with an eluent: cyclohexane/ethyl acetate (80:20).
The product 38a is isolated with a yield of 23%.

Characterization of the Compound 38a

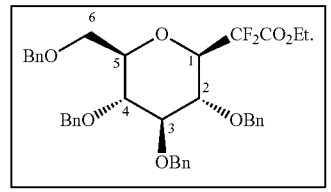

38a

Rf=0.51, eluent: cyclohexane/ethyl acetate (75:25).
$^1$H NMR (CDCl$_3$, 300 MHz)
1.10 (t, 3H, $^3J_{H10-H9}$ 7.2 Hz, H10), 3.56-3.68 (m, 5H), 3.91-4.01 (m, 2H), 4.22-4.86 (m, 10H, 4×CH$_2$Ph), 7.18-7.26 (m, 20H, H$_{Ar}$).
$^{19}$F NMR (CDCl$_3$, 282 MHz)
−115.9 (dd, $^3J_{F-H}$ 12.9, $^2J_{F-F}$ 259.7), −118.9 (dd, $^3J_{F-H}$ 10.7, $^2J_{F-F}$ 259.7).

Synthesis of the Compound 39a (FIG. 24)

In a flask under an inert atmosphere containing the ester 38a (78 mg; 0.12 mmol; 1 eq.) in solution in ethanol (5 mL), an aqueous solution of lithine (2M; 2 eq.) is added and the mixture is stirred overnight at room temperature. The mixture is concentrated and dissolved in DCM (5 mL), it is then acidified with a 1M HCl solution. The mixture is extracted with DCM (3×10 mL), and the organic phases are combined, washed with a saturated solution of NaCl and directly concentrated. The acid 39a is thereby isolated as a yellow oil which may be directly used for the next step without any further purifications, with a gross yield of 98%.

Characterization of the Compound 39a

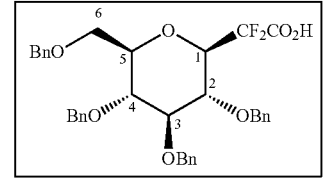

39a $^1$H NMR (CDCl$_3$, 30 MHz)
3.53-4.01 (m, 6H), 4.37-4.87 (m, 9H, 4×CH$_2$Ph), 7.08-7.22 (m, 20H, H$_{Ar}$).
$^{19}$F NMR (CDCl$_3$, 282 MHz)
−107.8 (dd, $^3J_{F-H}$ 8.6, $^2J_{F-F}$ 257.0), −110.5 (dd, $^3J_{F-H}$ 12.9, $^2J_{F-F}$ 257.0).
$^{13}$C NMR (CDCl$_3$, 75 MHz)
67.6, 68.8, 70.9, 72.5, 72.8, 73.6, 73.9, 74.2, 75.4, 75.5, 76.3, 77.6, 77.8, 79.7, 86.8, 128.0, 128.2, 128.2, 128.3, 128.3, 128.4, 128.5, 128.7, 128.8, 128.8, 128.9, 128.9, 136.7, 137.7, 137.8, 137.9, 138.0, 138.0, 138.1, 138.5.

Synthesis of the Compound 41a (FIG. 25)

In a flask under an inert atmosphere containing the ester 40a (175 mg; 0.315 mmol; 1 eq.) in solution in ethanol (15 mL), an aqueous solution of lithine (2M; 2 eq.) is added and the mixture is stirred overnight at room temperature. The medium is concentrated and dissolved in DCM (5 mL), it is then acidified with a 1M HCl solution (20 mL). The mixture is extracted with DCM (3×25 mL), and the organic phases are combined, washed with a saturated solution of NaCl and directly concentrated. The acid 41a is thereby isolated as a colorless oil which may be directly used for the next step without any further purifications with a gross yield of 87%.

Characterization of the Compound 41a

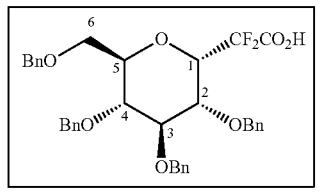

41a $^1$H NMR (CDCl$_3$, 30 MHz)
3.51-3.82 (m, 4H), 3.92-4.09 (m, 1H), 4.22-4.75 (m, 9H, 4×CH$_2$Ph), 7.08-7.22 (m, 15H, H$_{Ar}$).
$^{19}$F NMR (CDCl$_3$, 282 MHz)
−116.3 (d$_{app}$, $^2$J$_{F-F}$ 280.0), −128.1 (d, $^2$J$_{F-F}$ 284.0).

Synthesis of the Compound 42a (FIG. 26)

On a suspension of the acid 39a (74 mg; 0.120 mmol; 1.00 eq.), of the amine 16 (50 mg; 0.135 mmol; 1.10 eq.), of HOBT (18 mg; 0.130 mmol; 1.05 eq.), and of NMM (31 mg; 0.300 mmol; 2.05 eq.) in DCM (5 mL) under an argon atmosphere, EDCI (25 mg; 0.130 mmol; 1.05 eq.) is added. The reaction is stirred at room temperature for 2 days. Water (10 mL) is added, and the aqueous phase is extracted with DCM (3×10 mL). The organic phases are washed with a NaCl saturated solution (10 mL), dried on MgSO$_4$ and concentrated in vacuo so as to leave a pale brown oil. The residue is purified by chromatography on silica gel with a DCM/AcOEt mixture (90:10) as an eluent in order to obtain the pure product 42a as a colorless oil with a yield of 13%.

Characterization of the Compound 42a

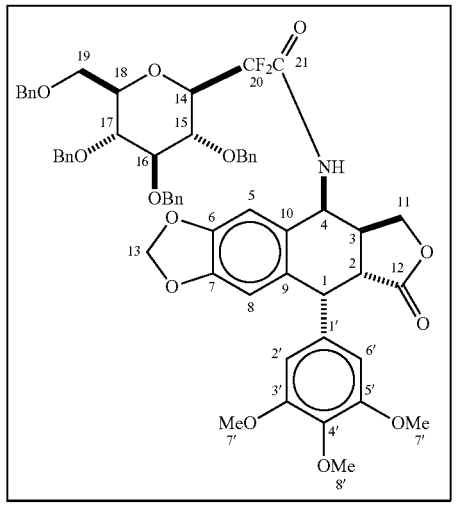

42a

Rf=0.75, eluent: DCM/AcOEt (80:20).
$^1$H NMR (CDCl$_3$, 300 MHz)
2.62-2.84 (m, 2H, H2, H3), 3.21-3.49 (m, 1H), 3.54 (s, 6H, H7'×6), 3.60 (s, 3H, H8'×3), 3.71-3.96 (m, 6H), 4.16-4.69 (m, 12H), 5.00-5.03 (m, 1H; H4), 5.71-5.79 (m, 2H, H13×2), 6.02-6.07 (m, 2H, H2', H6'), 6.28 (d, 1H, J 10.1, H8), 6.54 (s, 1H, J 3.1, H5), 7.00-7.28 (m, 20H).
$^{13}$C NMR (CDCl$_3$, 75 MHz)
37.4 (C3), 41.8 (C2), 43.8 (C1), 48.7 (C4), 56.4 (2C, C7'× 2), 60.9 (C8'), 68.0 (C19), 68.8 (C11), 72.3, 73.2, 75.2, 76.1, 77.4, 79.3, 86.4, 101.9 (C13), 108.3 (2C, C2', C6'), 109.1 (C5), 110.4 (C8), 127.6, 127.9, 127.9, 128.0, 128.2, 128.3, 128.5, 128.6, 128.7, 132.8, 134.7, 136.9, 137.5, 137.8, 137.9, 137.9, 138.4, 147.9 (C7), 148.9 (C6), 152.8 (2C, C3', C5'), 174.1 (C12).
$^{19}$F NMR (CDCl$_3$, 282 MHz)
−109.7 (dd, 1F, $^3$J$_{F-H}$ 3.7, $^2$J$_{F-F}$ 259.2), −122.0 (dd, 1F, $^3$J$_{F-H}$ 16.7 $^2$J$_{F-F}$ 259.2).

Synthesis of the Compound 43a (FIG. 27)

On a suspension of the acid 41a (9.0 mg; 0.0146 mmol; 1.00 eq.), of the amine 16 (6.0 mg; 0.0161 mmol; 1.10 eq.), of HOBT (2.1 mg; 0.0153 mmol; 1.05 eq.), and of NMM (3.2 mg; 0.0310 mmol; 2.05 eq.) in DCM (2 mL) under an argon atmosphere, EDCI (3 mg; 0.0153 mmol; 1.05 eq.) is added. The reaction is stirred at room temperature for 3 days. Water (5 mL) is added, and the aqueous phase is extracted with DCM (3×10 mL). The organic phases are washed with a saturated solution of NaCl (10 mL), dried on MgSO$_4$ and concentrated in vacuo so as to leave a beige solid. The compound 43a is used subsequently in the synthesis without any preliminary purifications.

Characterization of the Compound 43a

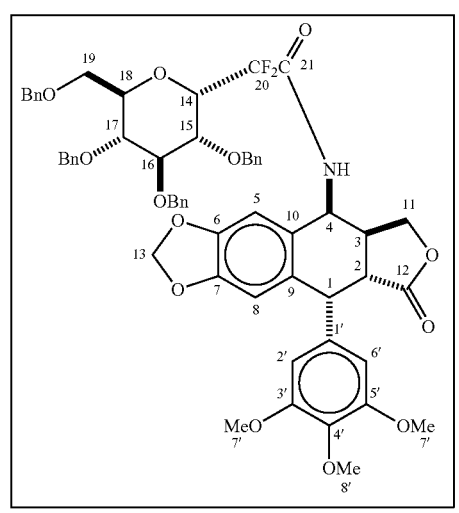

43a

Rf=0.92, eluent: DCM/AcOEt (80:20).
$^1$H NMR (CDCl$_3$, 300 MHz)
3.22-3.77 (m, 19H), 4.21-4.89 (m, 12H), 5.86-6.41 (m, 6H), 7.00-7.28 (m, 20H, H$_{Ar}$).
$^{19}$F NMR (CDCl$_3$, 282 MHz)
−105.2 (dd, 1F, $^3$J$_{F-H}$ 13.9, $^2$J$_{F-F}$ 271.5), −115.5 (d$_{app}$, 1F, $^2$J$_{F-F}$ 271.5).

Synthesis of the Compound 44a (FIG. 28)

In a flask, the compound 42a (12 mg; 0.0125 mmol) is dissolved in methanol (4 mL) with palladium on charcoal and placed under a hydrogen atmosphere. The mixture is stirred overnight at room temperature. The reaction mixture is filtered, concentrated and then purified by silica column chromatography with a DCM/MeOH mixture (90:10) as an eluent. The product 44a is isolated as a beige solid with a yield of 87%.

Characterization of the Compound 44a

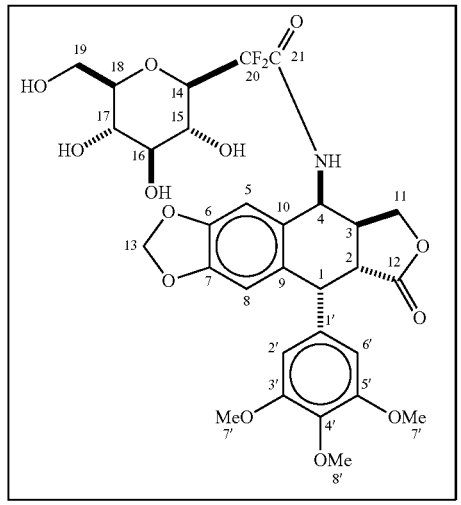

44a

Rf=0.29, eluent: DCM/methanol (90:10).

$^1$H NMR (MeOD, 300 MHz)

2.98-3.08 (m, 2H, H3, H2), 3.52-3.89 (m, 18H), 3.72 (s, 9H, H7'×6, H8'×3), 4.28 ($t_{app}$, 1H, $^2J_{H11\text{-}H11}$ 6.5, H11), 4.60 (s, 1H, H1), 5.22 (dd, 1H, $^3J_{H4\text{-}H3}$ 4.5, $^3J_{H4\text{-}NH}$ 10.7, H4), 5.94 (s, 2H, H13×2), 6.35 (s, 2H, H2', H6'), 6.50 (s, 1H, H8), 6.79 (s, 1H, H5).

$^{13}$C NMR (MeOD, 75 MHz)

38.7 (C3), 42.6 (C2), 45.1 (C1), 49.9 (C4), 56.5 (2C, C7'× 2), 61.0 (C8'), 61.9 (C19), 70.2 (C11), 70.6, 79.3, 82.1, 102.9 (C13), 109.5 (2C, C2', C6'), 110.3 (C5), 110.8 (C8), 129.8, 134.0, 137.2, 138.1, 148.9 (C7), 149.8 (C6), 153.8 (2C, C3', C5'), 176.9 (C12).

$^{19}$F NMR (MeOD, 282 MHz)

−114.4 (dd, 1F, $^2J_{F\text{-}F}$ 259.1, $^2J_{F\text{-}H}$ 6.8).

−121.9 (dd, 1F, $^2J_{F\text{-}F}$ 259.1, $^2J_{F\text{-}H}$ 16.1).

Mass spectrometry: ESI−: 652 (M−H)−.

Synthesis of the Compound 45a (FIG. 29)

In a flask, the compound 43a (39 mg; 0.04 mmol) is dissolved in methanol (5 mL) with palladium on charcoal and placed under a hydrogen atmosphere. The mixture is stirred overnight at room temperature. The reaction medium is filtered, concentrated and then purified by silica column chromatography with a DCM/MeOH mixture (80:20) as an eluent. The product 45a is isolated as a white solid with a yield of 70%.

Characterization of the Compound 45a

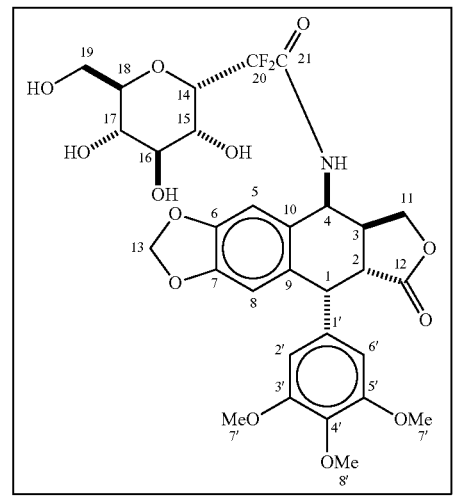

45a

Rf=0.83, eluent: DCM/methanol (80:20).

$^1$H NMR (MeOD, 300 MHz)

2.92-3.09 (m, 1H, H3), 3.22-3.38 (m, 2H, H2), 3.65-3.81 (m, 15H, H7'×6, H8'×3), 4.13 (dd, 1H, $^2J_{H11\text{-}H11}$ 9.0, $^3J_{H11\text{-}H3}$ 10.7, H11), 4.30 ($t_{app}$, 1H, $^2J_{H11\text{-}H11}$ 9.0, H11), 4.60 (d, 1H, $^3J_{H1\text{-}H2}$ 5.1, H1), 5.27 (d, 1H, $^3J_{H4\text{-}H3}$ 4.6, H4), 5.94 (d, 2H, $^2J_{H13\text{-}H13}$ 1.0, H13×2), 6.36 (s, 2H, H2', H6'), 6.48 (s, 1H, H8), 6.75 (s, 1H, H5).

$^{13}$C NMR (MeOD, 75 MHz)

38.8 (C3), 42.6 (C2), 45.1 (C1), 49.8 (C4), 57.5 (2C, C7'× 2), 61.0 (C8'), 62.3 (C19), 70.1 (C11), 70.8, 71.4, 75.1, 78.6, 102.9 (C13), 109.4 (2C, C2', C6'), 110.0 (C5), 110.8 (C8), 130.0, 133.9, 137.2, 138.1, 148.9 (C7), 149.7 (C6), 153.8 (2C, C3', C5'), 177.1 (C12).

$^{19}$F NMR (MeOD, 282 MHz)

(−110.9)-(−111.0) (m, 2F).

Mass spectrometry: ESI−: 652 (M−H)−.

Synthesis of the Compound 46a (FIG. 30)

In a flask, the compound 32a (40 mg; 0.061 mmol, 1.00 eq.) is dissolved in nitromethane (10 mL) with APTS (3 mg; 0.015 mmol; 0.25 eq.) and dimethoxyethane (166 mg; 1.840 mmol; 30.00 eq.) at room temperature under an inert atmosphere. The mixture is stirred for 4 hrs. Water (20 mL) is added, and the aqueous phase is extracted with CHCl$_3$ (2×30 mL). The organic phases are collected and washed with a saturated NaCl solution (30 mL), dried on Na$_2$SO$_4$ and concentrated in vacuo so as to leave a beige solid. The reaction raw product is purified by silica gel chromatographic column with a DCM/MeOH mixture (90:10) as an eluent. The product 46a is isolated as a beige solid with a yield of 81%.

Characterization of the Compound 46a

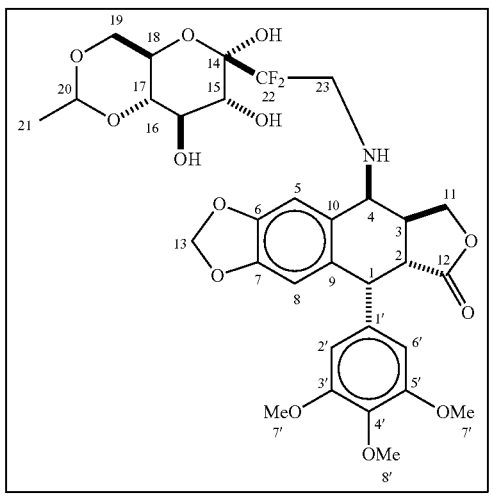

Rf=0.44, eluent: DCM/methanol (90:10).

$^1$H NMR (MeOD, 300 MHz)

1.30 (d, 3H, $^3J_{H21-H20}$ 5.0, H21×3), 2.82-2.85 (m, 1H, H3), 3.21-3.38 (m, 4H, H2, H23×2), 3.52 (t, 1H, $^2J_{H19-H19}$ 10.1, H19), 3.69 (s, 9H, H7'×6, H8'×3), 3.66-3.77 (m, 1H), 4.03 (dd, 1H, $^2J_{H19-H19}$ 10.1, $^3J_{H19-H18}$ 5.0, H19), 4.0.8 (d, 1H, J 4.1, H4), 4.31 (dd, 1H, $^2J_{H11-H11}$ 8.2, $^3J_{H11-H3}$ 10.9, H11), 4.39 (t, 1H, $^2J_{H11-H11}$ 8.2, H11), 4.53 (d, 1H, $^3J_{H1-H2}$ 5.4, H1), 4.75 (q, $^1$H, $^3J_{H20-H21}$ 5.0, H20), 5.93 (s, 2H, H13×2), 6.31 (s, 2H, H2', H6'), 6.43 (s, 1H, H8), 6.95 (s, 1H, H5).

$^{13}$C NMR (MeOD, 75 MHz)

20.6 (C21), 40.3 (C3), 42.2 (C2), 45.0 (C1), 51.3 (t, $^2J_{C23-F}$ 24.6, C23), 56.5 (2C, C7'×2), 57.6 (C4), 61.0 (C8'), 64.5, 69.3 (C19), 70.2 (C11), 72.8, 72.9, 81.5, 99.1 (t, $^2J_{C14-F}$ 26.3, C14), 100.7 (C20), 102.8 (C13), 109.4 (2C, C2', C6'), 110.1 (C5), 110.9 (C8), 132.8, 133.6, 137.7, 138.0, 148.7 (C7), 149.2 (C6), 153.7 (2C, C3', C5'), 177.8 (C12).

$^{19}$F NMR (CDCl$_3$, 282 MHz)

−117.9 (ddd, 1F, $^2J_{F-F}$ 255.4, $^3J_{F-H21}$ 17.2, 14.0), −119.4 (ddd, 1F, $^2J_{F-F}$ 255.4, $^3J_{F-H21}$ 17.2, 11.8).

Mass spectrometry: ESI+: 682 (M+H)+.

Results of Cytotoxicity

The first cytotoxicity tests were conducted on different cell lines such as KB, PC3, MCF7 and MCF7R, SF268, HL60, HT29, A549 cells at concentrations of 10$^{-5}$M in triplicate. Podophyllotoxin 1 and etoposide 2 were also tested under the same conditions as standards.

The results are expressed as an inhibition percentage of cellular growth.

It is observed that on this type of cells, the compound 27a has activity comparable with that of etoposide and of podophyllotoxin, and even better on certain cell lines. Also, the compound 32a tested on KB cells has cytotoxicity close to that of etoposide and podophyllotoxin, as well as 37a, 44a, 46a The IC$_{50}$ values are expressed in μM on KB cells in duplicate and were obtained for the 4 leading compounds, i.e. 27a, 32a, 44a, 37a and 46a in parallel with podophyllotoxin and etoposide.

|  | IC$_{50}$ (μM) |
|---|---|
| Podophyllotoxin 1 | 0.015/0.022 |
| 27a | 3.45/2.55 |
| 32a | 0.135/0.75 |
| 44a | 0.323/0.341 |
| 37a | 0.273/0.306 |
| 46a | 4.707/6.026 |
| Etoposide | 3.509/1.644 |

For both of these compounds, interesting values are therefore observed in terms of cytotoxicity and of IC$_{50}$ for the compounds 32a, 37a and 44a which makes these compounds good chemotherapy agents for treating cancer.

These compounds are presently subject to tests in vivo.

The invention claimed is:

1. A gem-difluorinated glycoconjugated compound of general formula I:

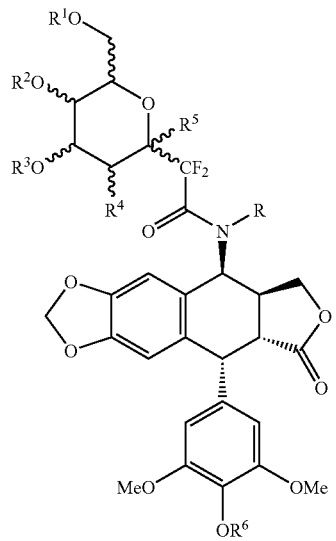

|  | 1 | 2 | 26a | 28a | 27a | 29a | 26b | 28b | 27b | 29b | 32a | 31a | 37a | 44a | 46a |
|---|---|---|---|---|---|---|---|---|---|---|---|---|---|---|---|
| KB | 90 | 84 | 43 | 54 | 91 | 66 | 12 | 15 | 12 | 0 | 94 | 22 | 91 | 90 | 86 |
| PC3 | 65 | 47 | 10 | 31 | 63 | 8 | 8 | 6 | 8 | 3 | — | — |  |  |  |
| MCF7 | 55 | 57 | 37 | 32 | 53 | 40 | 20 | 33 | 20 | 7 | — | — |  |  |  |
| MCF7R | 55 | 22 | 35 | 49 | 70 | 44 | 16 | 20 | 10 | 7 | — | — |  |  |  |
| SF268 | 74 | 82 | 7 | 28 | 65 | 11 | 7 | 17 | 7 | 6 | — | — |  |  |  |
| HL60 | 74 | 75 | 17 | 43 | 79 | 17 | 19 | 12 | 19 | 0 | — | — |  |  |  |
| HT29 | 84 | 79 | 10 | 14 | 87 | 17 | 13 | 17 | 8 | 6 | — | — |  |  |  |
| A549 | 83 | 65 | 23 | 21 | 78 | 6 | 7 | 10 | 6 | 1 | — | — |  |  |  | wherein
- R represents a hydrogen atom or a linear or branched alkyl, benzyl, acetyl, benzoyl group,
- $R^1$ and $R^2$, either identical or different, represent a hydrogen atom or a protective linear or branched alkyl, benzyl, benzoyl, acetyl, pivaloyl, trialkylsilyl, tertiobutyldiphenylsilyl group or an acetal group, of the CR'R" type, with R'and R", either identical or different, representing a hydrogen atom or a linear or branched alkyl, aryl, benzyl, thiophene group,
- $R^3$ represents a hydrogen atom or a protective linear or branched alkyl, benzyl, benzoyl, acetyl, pivaloyl, trialkylsilyl, tertiobutyldiphenylsilyl group,
- $R^4$ represents OR''', NGR'GR", $N_3$, or a phthalimide with R''' representing a hydrogen atom or a linear or branched alkyl, benzyl, benzoyl, acetyl, pivaloyl, trialkylsilyl, tertiobutyldiphenylsilyl protective group, and with GR' and GR", either identical or different representing a hydrogen atom or a linear or branched alkyl, benzyl, benzoyl, acetyl, alkyloxycarbonyl, allyloxycarbonyl, benzyloxycarbonyl group,
- $R^5$ represents a free or protective hydroxyl group or a halogen,
- $R^6$ represents a hydrogen atom or a linear or branched alkyl, acetyl, benzyl, $PO_3H$, $PO_3Na$ group, as well as its derivatives in the state of a mineral or organic acid addition salt.

2. The compound according to claim 1 of general formula II:

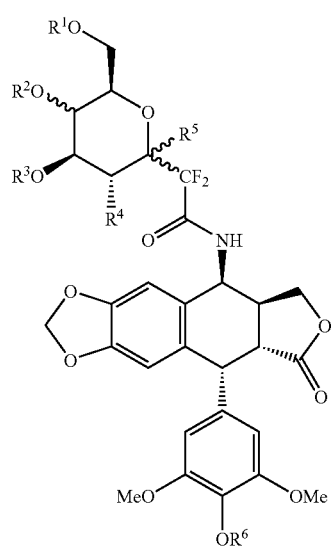

wherein R, $R^1$, $R^2$, $R^3$, $R^4$, $R^5$ and $R^6$ are as defined in formula I, as well as its derivatives in the state of a mineral or organic acid addition salt.

3. The compound of general formula III obtained by reaction of a compound according to claim 1:

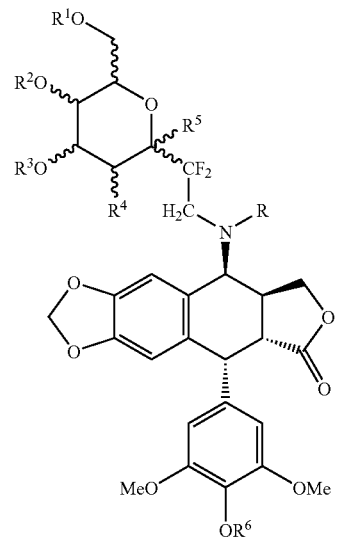

wherein
- R represents a hydrogen atom or a linear or branched alkyl, benzyl, acetyl, benzoyl group,
- $R^1$ and $R^2$, either identical or different, represent a hydrogen atom or a protective linear or branched alkyl, benzyl, benzoyl, acetyl, pivaloyl, trialkylsilyl, tertiobutyldiphenylsilyl group or an acetal group of the CR'R" type, with R'and R", either identical or different, representing a hydrogen atom or a linear or branched alkyl, aryl, benzyl, thiophene group,
- $R^3$ represents a hydrogen atom or a protective linear or branched alkyl, benzyl, benzoyl, acetyl, pivaloyl, trialkylsilyl, tertiobutyldiphenylsilyl group,
- $R^4$ represents OR''', NGR'GR", $N_3$, or a phthalimide with R''' representing a hydrogen atom or a protective linear or branched alkyl, benzyl, benzoyl, acetyl pivaloyl, trialkylsilyl, tertiobutyldiphenylsilyl group, and with GR'and GR", either identical or different, representing a hydrogen atom or a linear or branched alkyl, benzyl, benzoyl, acetyl, alkyloxycarbonyl, allyloxycarbonyl, benzyloxycarbonyl group,
- $R^5$ represents a free or protective hydroxyl group or a halogen,
- $R^6$ represents a hydrogen atom or a linear or branched alkyl, acetyl, benzyl, $PO_3H$, $PO_3Na$ group, as well as its derivatives in the state of a mineral or organic acid addition salt.

4. A method for the synthesis of a compound of general formula III:

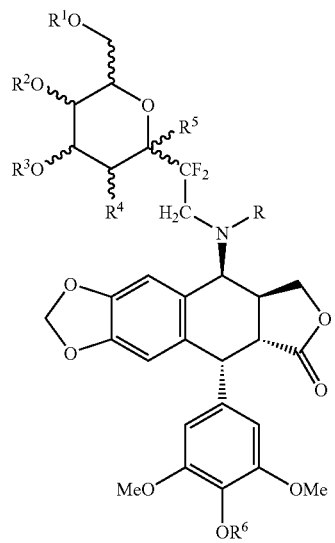

wherein
represents a hydrogen atom or a linear or branched alkyl, benzyl, acetyl, benzoyl group,
$R^1$ and $R^2$, either identical or different, represent a hydrogen atom or a protective linear or branched alkyl, benzyl, benzoyl, acetyl, pivaloyl, trialkylsilyl, tertiobutyldiphenylsilyl group or an acetal group of the CR'R" type, with R'and R", either identical or different, representing a hydrogen atom or a linear or branched alkyl, aryl, benzyl, thiophene group,
$R^3$ represents a hydrogen atom or a linear or branched alkyl, benzyl, benzoyl, acetyl, pivaloyl, trialkylsilyl, tertiobutyldiphenylsilyl protective group,
$R^4$ represents OR''', NGR'GR", $N_3$, or a phthalimide with R''' representing a hydrogen atom or a linear or branched alkyl, benzyl, benzoyl, acetyl, pivaloyl, trialkylsilyl, tertiobutyldiphenylsilyl protective group, and with GR'and GR", either identical or different, represent a hydrogen atom or a linear or branched alkyl, benzyl, benzoyl, acetyl, alkyloxycarbonyl, allyloxycarbonyl, benzyloxycarbonyl group,
$R^5$ represents a free or protective hydroxyl group or a halogen,
$R^6$ represents a hydrogen atom or a linear or branched alkyl, acetyl, benzyl, $PO_sH$, $PO_3Na$ group,
as well as its derivatives in the state of a mineral organic acid addition salt, the method comprising subjecting the compound of claim 1 to a reaction to synthesize the compound of general formula III.

5. A method for preparing the gem-difluorinated glycoconjugated compound of claim 1, comprising coupling a compound of formula IV:

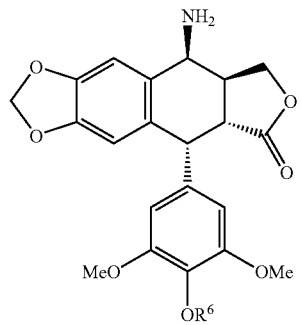

wherein $R^6$ is as defined in formula I, to a compound of formula V:

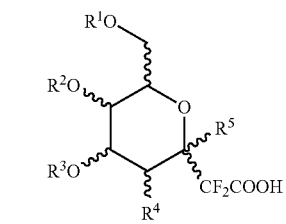

wherein $R^1$, $R^2$, $R^3$, $R^4$, $R^5$ are as defined in formula I.

6. A composition, comprising a compound according to claim 1.

7. A drug, comprising as active ingredient a compound according to claim 1.

8. A method for inhibiting cancer cell growth, comprising administering to a patient in need thereof a compound according to claim 1.

9. A method for the synthesis of a compound of general formula III:

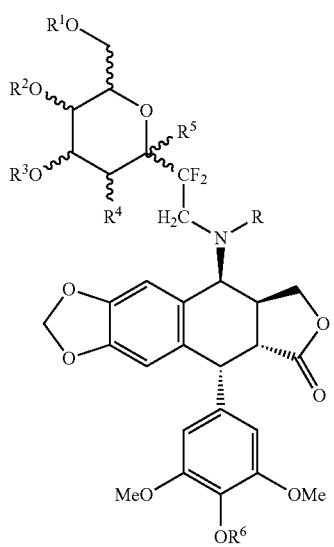

wherein
R represents a hydrogen atom or a linear or branched alkyl, benzyl, acetyl, benzoyl group,
$R^1$ and $R^2$, either identical or different, represent a hydrogen atom or a protective linear or branched alkyl, benzyl, benzoyl, acetyl, pivaloyl, trialkylsilyl, tertiobutyldiphenylsilyl group or an acetal group of the CR'R" type, with R'and R", either identical or different, representing a hydrogen atom or a linear or branched alkyl, aryl, benzyl, thiophene group, $R^3$ represents a hydrogen atom or a linear or branched alkyl, benzyl, benzoyl, acetyl, pivaloyl, trialkylsilyl, tertiobutyldiphenylsilyl protective group, $R^4$ represents OR''', NGR'GR", $N_3$, or a phthalimide with R''' representing a hydrogen atom or a linear or branched alkyl, benzyl, benzoyl, acetyl, pivaloyl, trialkylsilyl, tertiobutyldiphenylsilyl protective group, and with GR'and GR", either identical or different, represent a hydrogen atom or a linear or branched alkyl, benzyl, benzoyl, acetyl, alkyloxycarbonyl, allyloxycarbonyl, benzyloxycarbonyl group, $R^5$ represents a free or protective hydroxyl group or a halogen, $R^6$ represents a hydrogen atom or a linear or branched alkyl, acetyl, benzyl, $PO_3H$, $PO_3Na$ group, as well as its derivatives in the state of a mineral organic acid addition salt, the method comprising subjecting the compound of claim 2 to a reaction to synthesize the compound of general formula III.

10. The method of claim 9, wherein the reaction is a reaction for reducing the amide function.

11. The method of claim 4, wherein the reaction is a reaction for reducing the amide function.

12. A composition, comprising a compound according to claim 2.

13. A composition, comprising a compound according to claim 3.

14. A drug, comprising as active ingredient a compound according to claim 2.

15. A drug, comprising as active ingredient a compound according to claim 3.

16. A method for inhibiting cancer cell growth, comprising administering to a patient in need thereof a compound according to claim 2.

17. A method for inhibiting cancer cell growth, comprising administering to a patient in need thereof a compound according to claim 3.

* * * * *